US011845938B2

(12) United States Patent
Rossi et al.

(10) Patent No.: US 11,845,938 B2
(45) Date of Patent: *Dec. 19, 2023

(54) APTAMER COMPOSITIONS AND THE USE THEREOF

(71) Applicants: City of Hope, Duarte, CA (US); Apterna Limited, London (GB)

(72) Inventors: John J. Rossi, Azusa, CA (US); Sorah Yoon, Pasadena, CA (US); Nagy Habib, London (GB)

(73) Assignees: CITY OF HOPE, Duarte, CA (US); APTERNA LIMITED, London (GB)

(*) Notice: Subject to any disclaimer, the term of this patent is extended or adjusted under 35 U.S.C. 154(b) by 737 days.

This patent is subject to a terminal disclaimer.

(21) Appl. No.: 16/088,668

(22) PCT Filed: Mar. 31, 2017

(86) PCT No.: PCT/US2017/025334
§ 371 (c)(1),
(2) Date: Sep. 26, 2018

(87) PCT Pub. No.: WO2017/173247
PCT Pub. Date: Oct. 5, 2017

(65) Prior Publication Data
US 2020/0299696 A1  Sep. 24, 2020

Related U.S. Application Data

(60) Provisional application No. 62/316,051, filed on Mar. 31, 2016.

(51) Int. Cl.
| *C12N 15/11* | (2006.01) |
| *C12N 15/115* | (2010.01) |
| *A61K 31/4745* | (2006.01) |
| *A61K 31/513* | (2006.01) |
| *A61K 31/5365* | (2006.01) |
| *A61K 31/5517* | (2006.01) |
| *A61K 31/555* | (2006.01) |
| *A61K 31/704* | (2006.01) |
| *A61K 31/7068* | (2006.01) |

(52) U.S. Cl.
CPC ........ *C12N 15/115* (2013.01); *A61K 31/4745* (2013.01); *A61K 31/513* (2013.01); *A61K 31/5365* (2013.01); *A61K 31/555* (2013.01); *A61K 31/5517* (2013.01); *A61K 31/704* (2013.01); *A61K 31/7068* (2013.01); *C12N 2310/16* (2013.01); *C12N 2310/351* (2013.01); *C12N 2320/31* (2013.01)

(58) Field of Classification Search
CPC .............. C12N 15/115; C12N 2310/16; C12N 2310/351; C12N 2320/31; A61K 31/513; A61K 31/7068
See application file for complete search history.

(56) References Cited

U.S. PATENT DOCUMENTS

| 5,034,506 | A | 7/1991 | Summerton et al. |
| 5,143,854 | A | 9/1992 | Pirrung et al. |
| 5,235,033 | A | 8/1993 | Summerton et al. |
| 2007/0292389 | A1 | 12/2007 | Stassi et al. |
| 2011/0028403 | A1 | 2/2011 | Le Poole et al. |
| 2012/0149647 | A1 | 6/2012 | Brody et al. |
| 2014/0088300 | A1 | 3/2014 | Schmitz, Sr. et al. |
| 2015/0197752 | A1 | 7/2015 | Rossi et al. |

FOREIGN PATENT DOCUMENTS

| WO | WO-96/17958 A1 | 6/1996 |
| WO | WO-2013/134116 A1 | 9/2013 |
| WO | WO-2013/154735 A1 | 10/2013 |
| WO | WO-2014/138183 A1 | 9/2014 |
| WO | WO-2015/117201 A1 | 8/2015 |
| WO | WO-2015/134334 A1 | 9/2015 |
| WO | WO-2016/161165 A1 | 10/2016 |

OTHER PUBLICATIONS

Ray et al, Aptamer-Mediated Delivery of Chemotherapy to Pancreatic Cancer Cells, Nucleic Acid Therapeutics, 2012, vol. 22, No. 5: 295-305 (Year: 2012).*
Kruspe et al, An Aptamer Intrinsically Comprising 5-Fluoro-2'-deoxyuridine for Targeted Chemotherapy, Angew. Chem. Int. Ed., 2014, 53: 10541-10544 (Year: 2014).*
Altschul, S.F. et al. (Oct. 5, 1990). "Basic local alignment search tool," J Mol Biol 215(3):403-410.
Altschul, S.F. et al. (Sep. 1, 1997). "Gapped BLAST and PSI-BLAST: a new generation of protein database search programs," Nucleic Acids Research 25(17):3389-3402.
Bagatell, R. et al. (Aug. 2004). "Altered Hsp90 function in cancer: A unique therapeutic opportunity," Mol Cancer Ther 3:1021-1030.
Beaucage, S.L. et al. (Mar. 20, 1992). "Advances in the Synthesis of Oligonucleotides by the Phosphoramidite Approach," Tetrahedron 48(12):2223-2311.
Burris,H.A.3rd, et al. (Jun. 1997). "Improvements in survival and clinical benefit with gemcitabine as first-line therapy for patients with advanced pancreas cancer: a randomized trial," J Clin Oncol 15(6):2403-2413.
Eaton, B.E. et al. (Jun. 1997). "Post-SELEX combinatorial optimization of aptamers," Biorg Med Chem 5(6):1087-1986.
Ellington, A.D. et al. (Aug. 30, 1990). "In vitro selection of RNA molecules that bind specific ligands," Nature 346(6287):818-822.
Farrell, J.J. et al. (Jan. 2009, e-published Oct. 7, 2008). "Human equilibrative nucleoside transporter 1 levels predict response to gemcitabine in patients with pancreatic cancer," Gastroenterology 136(1):187-195.
Fodor, S.P. et al. (Feb. 15, 1991). "Light-directed, spatially addressable parallel chemical synthesis," Science (251):4995:767-773.

(Continued)

*Primary Examiner* — Ekaterina Poliakova-Georgantas
(74) *Attorney, Agent, or Firm* — Mintz, Levin, Cohn, Ferris, Glovsky and Popeo, P.C.

(57) ABSTRACT

Provided are aptamer compositions and their use for treating cancer.

12 Claims, 19 Drawing Sheets
Specification includes a Sequence Listing.

(56) References Cited

OTHER PUBLICATIONS

Giovannetti, E. et al. (Apr. 1, 2006). "Transcription analysis of human equilibrative nucleoside transporter-1 predicts survival in pancreas cancer patients treated with gemcitabine," *Cancer Res* 66(7):3928-3935.

Gold L. et al. (2010) "Aptamer-based multiplexed proteomic technology for biomarker discovery," *PLoS One* 5(12):e15004.

Huang, P. et al. (Nov. 15, 1991) "Action of 2',2'-difluorodeoxycytidine on DNA synthesis," *Cancer Res* 51(22):6110-6117.

Hyun, J.J. et al. (Nov. 2013, e-published Aug. 14, 2013). "Expression of heat shock protein 70 modulates the chemoresponsiveness of pancreatic cancer," *Gut Liver* 7(6):739-746.

International Search Report dated Aug. 29, 2017, for PCT Application No. PCT/US2017/025334, filed Mar. 31, 2017, 6 pages.

Johnston, M. (Feb. 26, 1998). "Gene chips: Array of hope for understanding gene regulation," *Curr. Biol.* 8(5): R171-R174.

Kern, S. et al. (Jul. 1997). Direct Hybridization of Large-Insert Genomic Clones on High-Density Gridded cDNA Filter Arrays, *Biotechniques* 23(1):120-124.

Marcus-Sakura, C.J. (Aug. 1, 1988). "Techniques for using antisense oligodeoxyribonucleotides to study gene expression," Anal. Biochem. 172(2):289-295.

Matuo, R. et al. (May 2009). "5-Fluorouracil and its active metabolite FdUMP cause DNA damage in human SW620 colon adenocarcinoma cell line," *J Appl Toxicol* 29(4):308-316.

Needleman, S.B. et al. (Mar. 1970). "A general method applicable to the search for similarities in the amino acid sequence of two proteins," J Mol Biol 48(3):443-453.

Ohhashi, S. et al. (Jul.-Aug. 2008. "Down-regulation of deoxycytidine kinase enhances acquired resistance to gemcitabine in pancreatic cancer," *Anticancer Res* 28(4B):2205-2212.

Pearson, W.R. et al. (Apr. 1988). "Improved tools for biological sequence comparison," *Proc. Nat'l. Acad. Sci. USA* 85(8):2444-2448.

Pourquier, P. et al. (Aug. 2002). "Gemcitabine (2',2'-difluoro-2'-deoxycytidine), an antimetabolite that poisons topoisomerase I," *Clin Cancer Res* 8(8):2499-2504.

Ruiz Van Haperen, V.W. et al. (Aug. 17, 1993). "2',2'-Difluoro-deoxycytidine (gemcitabine) incorporation into RNA and DNA of tumour cell lines," Biochem Pharmacol 46(4):762-766.

Satelli, A. et al. (Sep. 2011, e-published Jun. 3, 2011). "Vimentin in cancer and its potential as a molecular target for cancer therapy," *Cell Mol Life Sci* 68(18):3033-3046.

Schummer, M. et al. (Dec. 1997). "Inexpensive Handheld Device for the Construction of High-Density Nucleic Acid Arrays," *Biotechniques* 23(6):1087-1092.

Sinha, N.D. et al. (Jun. 11, 1984). "Polymer support oligonucleotide synthesis XVIII: use of beta-cyanoethyl-N,N-dialkylamino-/N-morpholino phosphoramidite of deoxynucleosides for the synthesis of DNA fragments simplifying deprotection and isolation of the final product.," *Nucl Acids Res* 12(11):4539-4557.

Smith, T.F. et al. (1981). "Comparison of Bioseguences," *Adv. Appl. Math* 2:482-489.

Soares, D.G. et al. (Aug. 7, 2007). "Replication and homologous recombination repair regulate DNA double-strand break formation by the antitumor alkylator ecteinascidin 743," *Proc Natl Acad Sci U S A* 104(32):13062-13067.

Tuerk, C. et al. (Aug. 3, 1990). "Systematic evolution of ligands by exponential enrichment: RNA ligands to bacteriophage T4 DNA polymerase," *Science* 249(4968): 505-510.

Weintraub, H.M. et al. (Jan. 1990). "Antisense RNA and DNA," *Sci Am* 262(1):40-46.

Written Opinion dated Aug. 29, 2017, for PCT Application No. PCT/US2017/025334, filed Mar. 31, 2017, 9 pages.

Wu, W. et al. (2007). "Synthesis and biological activity of a gemcitabine phosphoramidate prodrug," *J Med Chem* 50(15):3743-3746.

Zhou, J. et al. (May 2009, e-published Mar. 21, 2009). "Selection, characterization and application of new RNA HIV gp 120 aptamers for facile delivery of Dicer substrate siRNAs into HIV infected cells," Nucleic Acids Res. 37(9):3094-3109.

\* cited by examiner

FIG. 1B

GGG AGA C̲AA GAA UAA AC̲G C̲UC̲ AAU GGC̲ GAA UGC̲ C̲C̲G C̲C̲U AAU AGG GC̲G UUA UGA C̲UU GUU GAG UUC̲ GAC̲ AGG AGG C̲UC̲ AC̲A AC̲A GGC̲ (SEQ ID NO: 18): underlined C is dFdCMP (19 molecules/aptamer, 21.8%)

GGG AGA CAA GAA U̲AA ACG CU̲C AAU̲ GGC GAA U̲GC CCG CCU̲ AAU̲ AGG GCG U̲U̲A U̲GA CU̲U̲ GU̲U̲ GAG U̲U̲C GAC AGG AGG CU̲C ACA ACA GGC (SEQ ID NO: 19): underlined U is 5FdUMP (16 molecules/aptamer, 18.4%)

Incorporation of dFdCMP and 5FdUMP into P19, instead of 2'F-CTP or 2'F-UTP

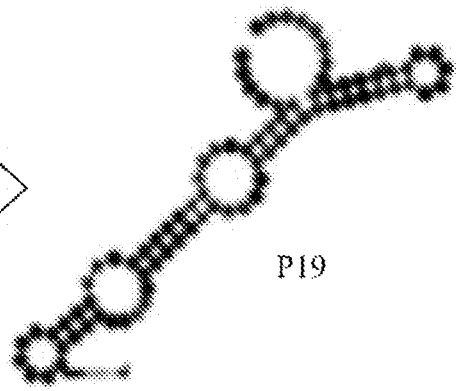

P19 tP19-MMAE tP19-DM1

Aptamers can be combined with multiple cytotoxic agents simultaneously for targeted delivery of chemotherapeutics

APTAMER COMPOSITIONS AND THE USE THEREOF

CROSS-REFERENCES TO RELATED APPLICATIONS

This application claims the benefit of U.S. Provisional Application No. 62/316,051, filed Mar. 31, 2016, the content of which is incorporated herein by reference in its entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48440-607001WO_ST25.TXT, created Mar. 29, 2017, 27,464 bytes in size, machine format IBM-PC, MS-Windows operating system, is hereby incorporated by reference.

BACKGROUND

In the last decades, an overwhelming number of studies remarkably contributed to the comprehension of the molecular mechanisms leading to cancer. However, this scientific progress in the molecular oncology field has not been paralleled by a comparable progress in cancer therapy. Surgery and/or radiotherapy are the still the main modality of local treatment of cancer in the majority of patients. However, these treatments are effective only at initial phases of the disease and in particular for certain solid tumors, while they are not effective for distant recurrence of the disease. In some tumor classes, chemotherapeutic treatments have been developed, which generally relies on drugs, hormones and antibodies, targeting specific biological processes used by cancers to grow and spread. However, so far many cancer therapies had limited efficacy due to severity of side effects and overall toxicity. Therefore, there is a great demand for new therapeutics to advance the treatment of cancer. Provided herein are solutions to these and other problems in the art.

SUMMARY

In a first aspect, there is provided a composition including an aptamer and an anticancer agent, where the aptamer is bound to the anticancer agent.

In another aspect, there is provided a pharmaceutical formulation including a composition including an aptamer and an anticancer agent as disclosed herein and a pharmaceutically acceptable excipient.

In another aspect, there is provided a method of treating cancer. The method includes administering to a subject in need thereof an effective amount of a composition as disclosed and embodiments thereof.

In another aspect, there is provided a composition including an aptamer and an anticancer agent as disclosed herein for use in a method of treating cancer.

In another aspect, there is provided the use of a composition including an aptamer and an anticancer agent as disclosed herein in the manufacture of a medicament or pharmaceutical composition for use in a method of treating cancer.

BRIEF DESCRIPTION OF THE DRAWINGS

FIGS. 1A-1D. ApDCs of gemcitabine and 5-FU. (FIG. 1A) Chemical structure of gemcitabine and 5-FU prodrug (5F-dUTP). (FIG. 1B) The sequence of P19 incorporated with dFdCMP (dFdCTP) (SEQ ID NO: 18) and 5FdUMP (5FdUTP) (SEQ ID NO: 19) into P19, instead of 2'F-CTP and 2'F-UTP. (FIG. 1C) Intrinsic incorporation of active metabolites of gemcitabine (dFdCMP) and 5FdUMP in P19. M: Marker. 1:P19, 2: P19-dFdCMP, 3:P19-5FdUMP. (FIG. 1D) The dissociation constant ($K_D$) was measured by flow cytometry using increasing concentrations of Cy3-labeled aptamers (from 15.6 to 1000 nM). Mean fluorescence intensity (MFI) was measured and calculated using a one-site binding model for non-linear regression. The upper panel of FIG. 1D shows the $K_D$ of P19-5FdUMP and the lower panel of FIG. 1D shows $K_D$ of P19-dFdCMP.

(FIGS. 2A-2B) The pancreatic cell lines PANC-1 were treated with 200 nM of the Cy3-labeled dFdCMP-P19-ApDC (FIG. 2A) or 5FdUMP-P19-ApDC (FIG. 2B) and analyzed by confocal microscopy. All of the pancreatic lines showed punctuate regions of Cy3 labeling. Dyes: Cy3 labeled RNAs, Hoechst 33342. Scale bar: 10 m. (FIG. 2C) After treatment dFdCMP-P19-ApDC or 5FdUMP-P19-ApDC in PANC-1 cells for 72 hrs, cell viability was measured by MTT assay. One-way ANOVA test: **≤0.0001, *≤0.001. (FIG. 2D) After treatment dFdCMP-P19-ApDC or 5FdUMP-P19-ApDC in chemo-resistance AsPC-1 cells for 72 hrs, cell viability was measured by MTT assay. One-way ANOVA test: **≤0.0001, *≤0.001

(FIG. 3A) PANC-1 cells treated with dFdCMP-P19-ApDC or 5FdUMP-P19-ApDC at 500 nM were stained with antibodies to rH2AX. Fluorescence images were obtained via confocal microscopy. Dyes: rH2AX, Hoechst 3334. Scale bar: 10 m. (FIG. 3B) Figure is histogram depicting quantification of rH2AX incidents in images as measured by Image Pro 9.1.

(FIG. 4A) The dissociation constant ($K_D$) was measured by flow cytometry using increasing concentrations of Cy3-labeled aptamers (from 15.6 to 500 nM). Mean fluorescence intensity (MFI) was measured and calculated using a one-site binding model for non-linear regression. The left panel of FIG. 4A shows the binding affinity of P19 to cancer cells and the right panel of FIG. 4A shows the binding affinity of tP19 to cancer cells. (FIG. 4B) The pancreatic cell lines PANC-1 and AsPC-1 were treated with 200 nM of the Cy3-labeled tP19 aptamer and analyzed by confocal microscopy. All of the pancreatic lines showed punctate regions of Cy3 labeling. (FIG. 4C) Non pancreatic lines including Huh7, HepG2, MCF7 and PC3 cells were also treated with 200 nM of Cy3-labeled tP19 and P1 aptamers. No Cy3 signal was observed. Dye Hoechst 33342. Scale bar: 10 μm.

(FIG. 5A) The figure depicts the chemical conjugation of MMAE at 5' end of sticky sequence (hybridization sequence). (FIG. 5B) The figure depicts the chemical conjugation of DM1 at 5' end of sticky sequence (hybridization sequence). (FIG. 5C) The figure depicts sizes of conjugates of MMAE and DM1 with tP19 via sticky sequence (hybridization sequence). After annealing in the folding buffer, MMAE-tP19-ApDC and DM1-tP19-ApDC were loaded in 12% native gel. (FIG. 5D) The figure depicts cell internalization of ApDCs. Cy3 labeled MMAE-tP19-ApDC and DM1-tP19-ApDC which were treated in PANC-1 cell at 500 nM for 2 hours.

(FIG. 7A) After treatment of MMAE-tP19-ApDC in cells for 72 hrs, cell viability was measured by MTT assay. (FIG. 7B) After treatment of DM1-tP19-ApDC, in cells for 72 hrs, cell viability was measured by MTT assay.

DETAILED DESCRIPTION

Definitions

Figure 1A:
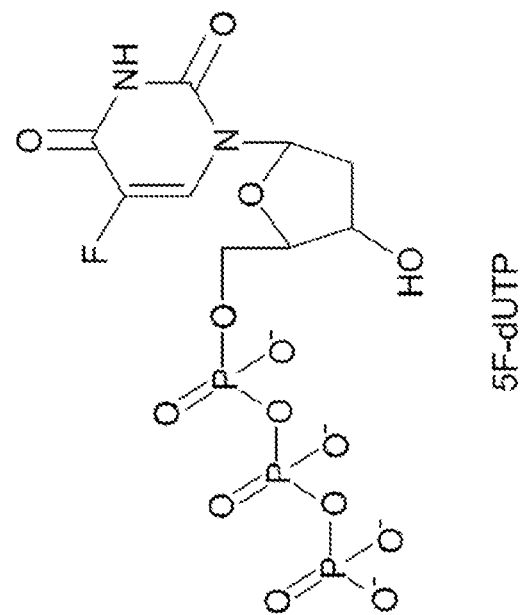
Figure 1A:
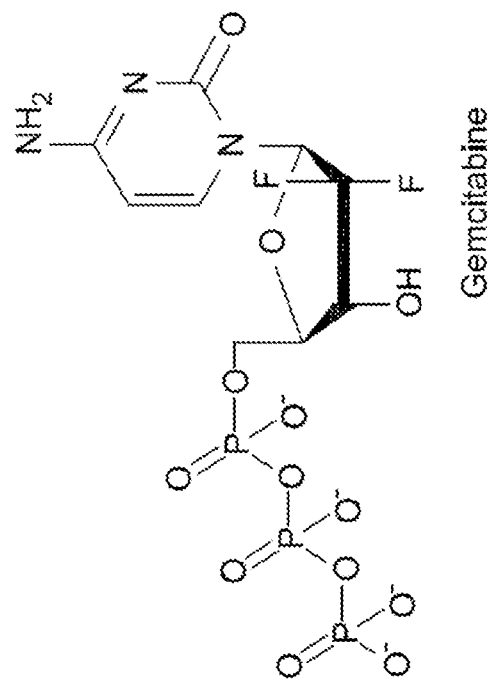

While various embodiments and aspects are shown and described herein, it will be obvious to those skilled in the art that such embodiments and aspects are provided by way of example only. Numerous variations, changes, and substitutions will now occur to those skilled in the art without departing from the compositions and methods provided herein. It should be understood that various alternatives to the embodiments described herein may be employed in practicing the compositions and methods provided herein.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of the compositions and methods provided herein. The following definitions are provided to facilitate understanding of certain terms used frequently herein and are not meant to limit the scope of the present disclosure.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) 0, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2$R'— represents both —$C(O)_2$R'— and —R'$C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic non-aromatic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently (e.g., biphenyl). A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —NR'NR"R''', —ONR'R", —NR'C=(O)NR"NR'''R'''', —CN, —NO$_2$, in a number ranging from zero to (2m'+1), where m' is the total number of carbon atoms in such radical. R, R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC (O)NR'R", —NR"C(O)R', —NR'—C(O)NR"R''', —NR"C(O)$_2$R', —NR—C(NR'R"R''')=NR'''', —NR—C(NR' R")=NR''', —S(O)R', —S(O)$_2$R', —S(O)$_2$NR'R", —NRSO$_2$R', —NR'NR"R''', —ONR'R", —NR'C=(O)NR''NR'''R'''', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$-U-, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$-B-, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
 (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and
 (ii) alkyl, heteroalkyl, cycloalkyl, heterocycloalkyl, aryl, heteroaryl, substituted with at least one substituent selected from:
  (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, and
  (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section below.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogues or modified backbone residues or linkages, which are synthetic, naturally occurring, and non-naturally occurring, which have similar binding properties as the reference nucleic acid, and which are metabolized in a manner similar to the reference nucleotides. Examples of such analogues include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analogue nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogues can be made; alternatively, mixtures of different nucleic acid analogues, and mixtures of naturally occurring nucleic acids and analogues may be made. In embodiments, the internucleotide linkages in DNA are phosphodiester, phosphodiester derivatives, or a combination of both.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual*, 18.1-18.88.

The term "aptamer" as provided herein refers to oligonucleotides (e.g. short oligonucleotides or deoxyribonucleotides), that bind (e.g. with high affinity and specificity) to proteins, peptides, and small molecules. Aptamers may be RNA. Aptamers may have secondary or tertiary structure and, thus, may be able to fold into diverse and intricate molecular structures. Aptamers can be selected in vitro from very large libraries of randomized sequences by the process of systemic evolution of ligands by exponential enrichment (SELEX as described in Ellington A D, Szostak J W (1990) In vitro selection of RNA molecules that bind specific ligands. Nature 346:818-822; Tuerk C, Gold L (1990) Systematic evolution of ligands by exponential enrichment: RNA ligands to bacteriophage T4 DNA polymerase. Science 249:505-510) or by developing SOMAmers (slow off-rate modified aptamers) (Gold L et al. (2010) Aptamer-based multiplexed proteomic technology for biomarker discovery. PLoS ONE 5(12):e15004). Applying the SELEX and the SOMAmer technology includes for instance adding functional groups that mimic amino acid side chains to expand the aptamer's chemical diversity. As a result high affinity aptamers for a protein may be enriched and identified. Aptamers may exhibit many desirable properties for targeted drug delivery, such as ease of selection and synthesis, high binding affinity and specificity, low immunogenicity, and versatile synthetic accessibility. Anti-cancer agents (e.g. chemotherapy drugs, toxins, and siRNAs) may be successfully delivered to cancer cells in vitro using aptamers.

Aptamers are nucleic acid molecules characterised by the ability to bind to a target molecule with high specificity and high affinity. Almost every aptamer identified to date is a non-naturally occurring molecule.

Aptamers may be DNA or RNA molecules and may be single stranded or double stranded. The aptamer may comprise chemically modified nucleotides or nucleosides, for example in which the sugar and/or phosphate and/or base is chemically modified. Such modifications may improve the stability of the aptamer or make the aptamer more resistant to degradation. The aptamers provided herein may include chemical modifications as described herein such as a chemical substitution at a sugar position, a phosphate position, and/or a base position of the nucleic acid including, for example, incorporation of a modified nucleotide, incorporation of a capping moiety (e.g. 3' capping), conjugation to a high molecular weight, non-immunogenic compound (e.g. polyethylene glycol (PEG)), conjugation to a lipophilic compound, substitutions in the phosphate backbone. Base modifications may include 5-position pyrimidine modifications, modifications at exocyclic amines, substitution of 4-thiouridine, substitution of 5-bromo- or 5-iodo-uracil, backbone modifications. Sugar modifications may include 2'-amine nucleotides (2'-$NH_2$), 2'-fluoro nucleotides (2'-F), and 2'-O-methyl (2'-OMe) nucleotides. A wide range of nucleotide, nucleoside, base and phosphate modifications are known to those or ordinary skill in the art, e.g. as described in Eaton et al., Bioorganic & Medicinal Chemistry, Vol. 5, No. 6, pp 1087-1096, 1997.

Aptamers may be synthesised by methods which are well known to the skilled person. For example, aptamers may be chemically synthesised, e.g. on a solid support. Solid phase synthesis may use phosphoramidite chemistry. Briefly, a solid supported nucleotide is detritylated, then coupled with a suitably activated nucleoside phosphoramidite to form a phosphite triester linkage. Capping may then occur, followed by oxidation of the phosphite triester with an oxidant, typically iodine. The cycle may then be repeated to assemble the aptamer (e.g., see Sinha, N. D.; Biernat, J.; McManus, J.;

Köster, H. Nucleic Acids Res. 1984, 12, 4539; and Beaucage, S. L.; Lyer, R. P. (1992). *Tetrahedron* 48 (12): 2223).

Aptamers can be thought of as the nucleic acid equivalent of monoclonal antibodies and often have $K_d$'s in the nM or pM range, e.g. less than one of 500 nM, 100 nM, 50 nM, 10 nM, 1 nM, 500 pM, 100 pM. As with monoclonal antibodies, they may be useful in virtually any situation in which target binding is required, including use in therapeutic and diagnostic applications, in vitro or in vivo. In vitro diagnostic applications may include use in detecting the presence or absence of a target molecule.

Aptamers described herein may be provided in purified or isolated form. Aptamers described herein may be formulated as a pharmaceutical composition or medicament.

In embodiments, the nucleic acid sequence of an aptamer may optionally have a minimum length of one of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In embodiments, the nucleic acid sequence of an aptamer, may optionally have a maximum length of one of 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In embodiments, the nucleic acid sequence of an aptamer, may optionally have a length of one of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In embodiments, the nucleic acid sequence of an aptamer, may have a degree of primary sequence identity with one of SEQ ID NOs 1 to 7, that is at least one of 80%, 81%, 82%, 83%, 84%, 85%, 86%, 87%, 88%, 89%, 90%, 91%, 92%, 93%, 94%, 95%, 96%, 97%, 98%, 99%, or 100%.

An "antisense nucleic acid" as referred to herein is a nucleic acid (e.g. DNA or RNA molecule) that is complementary to at least a portion of a specific target nucleic acid (e.g. an mRNA translatable into a protein) and is typically capable of reducing transcription of the target nucleic acid (e.g. mRNA from DNA) or reducing the translation of the target nucleic acid (e.g. mRNA) or altering transcript splicing (e.g. single stranded morpholino oligo). See, e.g., Weintraub, *Scientific American*, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid (e.g. target mRNA). In embodiments, the antisense nucleic acid hybridizes to the target nucleic acid sequence (e.g. mRNA) under stringent hybridization conditions. In embodiments, the antisense nucleic acid hybridizes to the target nucleic acid (e.g. mRNA) under moderately stringent hybridization conditions. Antisense nucleic acids may comprise naturally occurring nucleotides or modified nucleotides such as, e.g., phosphorothioate, methylphosphonate, and -anomeric sugar-phosphate, backbonemodified nucleotides.

In the cell, the antisense nucleic acids may hybridize to the corresponding mRNA, forming a double-stranded molecule. The antisense nucleic acids interfere with the translation of the mRNA, since the cell will not translate an mRNA that is double-stranded. The use of antisense methods to inhibit the in vitro translation of genes is well known in the art (Marcus-Sakura, Anal. Biochem., 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogues), short hairpin RNAs (shRNA), micro RNAs (miRNA), saRNAs (small activating RNAs) and small nucleolar RNAs (snoRNA) or certain of their derivatives or pre-cursors.

A "siRNA," "small interfering RNA," "small RNA," or "RNAi" as provided herein, refers to a nucleic acid that forms a double stranded RNA, which double stranded RNA has the ability to reduce or inhibit expression of a gene or target gene when present in the same cell as the gene or target gene. The complementary portions of the nucleic acid that hybridize to form the double stranded molecule typically have substantial or complete identity. In one embodiment, a siRNA or RNAi is a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

A "saRNA," or "small activating RNA" as provided herein refers to a nucleic acid that forms a double stranded RNA, which double stranded RNA has the ability to increase or activate expression of a gene or target gene when present in the same cell as the gene or target gene. The complementary portions of the nucleic acid that hybridize to form the double stranded molecule typically have substantial or complete identity. In one embodiment, a saRNA is a nucleic acid that has substantial or complete identity to a target gene and forms a double stranded saRNA. Typically, the nucleic acid is at least about 15-50 nucleotides in length (e.g., each complementary sequence of the double stranded saRNA is 15-50 nucleotides in length, and the double stranded saRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

As used herein, the term "conjugate" refers to the association between atoms or molecules. The association can be direct or indirect. For example, a conjugate between a nucleic acid (e.g., aptamer) and a compound moiety (e.g. an anticancer agent) as provided herein can be direct, e.g., by covalent bond, or indirect, e.g., by non-covalent bond. Optionally, conjugates are formed using conjugate chemistry including, but not limited to, nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. Thus, the nucleic acid (e.g., aptamer) can be attached to a compound moiety (e.g., an anticancer agent) through its backbone. Optionally, the nucleic acid (e.g., aptamer) includes one or more reactive moieties, e.g., an amino acid reactive moiety, that facilitates the interaction of the nucleic acid (e.g., aptamer) with the compound moiety (e.g., an anticancer agent).

Useful reactive moieties or functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogues and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogues refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogues have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogues, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles described herein.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J Mol. Biol.* 48:443 (1970), by the search for similarity method of Pearson & Lipman, *Proc. Nat'l. Acad. Sci.* USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively.

For specific proteins described herein (e.g., mHSP70), the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

The term "HSP70" refers to the family of approximately 70 kilodalton heat shock proteins as well-known in the art. In embodiment, the HSP70 is mHSP70. The term "mHSP70" as provided herein includes any of the mitochondrial HSP70 (mHSP70) protein naturally occurring forms, homologs or variants that maintain the activity of mHSP70 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the mHSP70 protein is the protein as identified by the NCBI sequence reference GI:24234688. In embodiments, the mHSP70 protein is the protein as identified by the NCBI sequence reference GI:24234688, homolog or functional fragment thereof mHSP70 may also be referred to herein as mortalin, CSA, GRP-75, GRP75, HEL-S-124m, HSPA9B, MOT, MOT2, MTHSP75 or PBP74.

The term "HSP90" refers to the family of approximately 90 kilodalton heat shock proteins as well-known in the art. The term "HSP90" as provided herein includes any of the protein naturally occurring forms, homologs or variants that maintain the activity of HSP90 (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the HSP90 protein is the protein as identified by Genbank accession no. NP_001017963.2 GI:153792590 or NP_005339.3 GI:154146191. Overexpression of HSP90 in cancer is linked to poor prognosis, e.g. see Bagatell and Whitesell., Mol Cancer Ther August 2004 3; 1021.

The term "vimentin" refers to the family of class III intermediate filaments found in a number of health non-epithelial cells, including mesenchymal stem cells. The term "vimentin" as provided herein includes any of the protein naturally occurring forms, homologs or variants that maintain the activity of vimentin (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In embodiments, the vimentin protein is the protein as identified by the UniProt accession no. P08670 NCBI sequence reference or by Genbank accession no. NP_003371.2 GI:62414289. Vimentin is overexpressed in various epithelial cancers, including prostate cancer, gastrointestinal tumors, tumors of the central nervous system, breast cancer, malignant melanoma, and lung cancer (Satelli et al., Cell mol Life Sci 2011 September; 68(18):3033-46.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells.

A "cancer cell" refers to any cell that is derived from a cancer sample. "Cancer stem cells (CSCs)" refer to cancer cells that possess characteristics associated with normal stem cells, specifically the ability to give rise to all cell types found in a particular cancer sample. CSCs are therefore tumorigenic (tumor-forming), perhaps in contrast to other non-tumorigenic cancer cells. CSCs may generate tumors through the stem cell processes of self-renewal and differentiation into multiple cell types. Such cells are hypothesized to persist in tumors as a distinct population and cause relapse and metastasis by giving rise to new tumors.

"Undifferentiated cancer cells," "undifferentiated cancer," and the like refer to cancer cells, or cancer including cancer cells, that are immature and primitive, and do not look like cells in the tissue from it arose. Undifferentiated cancer cells do not have specialized (i.e. "mature") structures or functions. Such cancer cells often grow and spread quickly. As such, it can be difficult to categorize such cancers as a particular type of cancer, such as carcinoma, lymphoma or melanoma. The compositions described herein target CSCs and undifferentiated cancer cells, thus providing improvement of survival of cancer patients especially patients with metastatic disease.

Grading systems differ, depending on the type of cancer. In general, tumors are graded as 1, 2, 3 or 4, depending on the amount of abnormality. In Grade 1 tumors, the tumor cells and the organisation of the tumor tissue appear close to normal. These tumors tend to grow and spread slowly. In contrast, the cells and tissue of Grade 3 and Grade 4 tumors do not look like normal cells and tissue. Grade 3 and Grade 4 tumors tend to grow rapidly and spread faster than tumors with a lower grade.

The following grading system may be applied:
GX: Grade cannot be assessed
G1: Well differentiated (low grade)
G2: Moderately differentiated (intermediate grade)
G3: Poorly differentiated (high grade)
G4: Undifferentiated (high grade).

In embodiments, the cancer is a high grade cancer, such as a poorly differentiated or undifferentiated cancer, or G3 or G4 cancer. In embodiments, the cancer is an undifferentiated cancer, or G4 cancer. In embodiments, the cancer is a malignant cancer.

In embodiments, the cancer is high grade non-pancreatic cancer. That is, a cancer of non-pancreatic origin which is poorly differentiated or undifferentiated. The cancer may be a malignant non-pancreatic cancer.

In embodiments, the cancer is selected from prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma.

"Disease" or "condition" refer to a state of being or health status of a patient or subject capable of being treated with a compound, pharmaceutical composition, or method provided herein. In embodiments, the disease is cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma), an infectious disease (e.g., HIV infection), an inflammatory disease (e.g., rheumatoid arthritis) or a metabolic disease (e.g., diabetes). In embodiments, the disease is a disease related to (e.g. caused by) an aberrant activity of HSP70 (e.g. mHSP70), HSP70 (e.g. mHSP70) phosphorylation, or HSP70 (e.g. mHSP70) pathway activity, or pathway activated by HSP70. In embodiments, the disease is a disease related to (e.g. caused by) an aberrant activity of HSP90, HSP90 phosphorylation, or HSP90 pathway activity, or pathway activated by HSP90. In embodiments, the disease is a disease related to (e.g. caused by) an aberrant activity of vimentin, vimentin phosphorylation, or vimentin pathway activity, or pathway activated by vimentin. In some embodiments, the disease is cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma).

As used herein, the term "cancer" refers to all types of cancer, neoplasm or malignant tumors found in mammals, including leukemia, lymphoma, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifomi carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) or viral disease (e.g., HIV infection associated disease)) means that the disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) or viral disease (e.g., HIV infection associated disease)) is caused by (in whole or in part), or a symptom of the disease is caused by (in whole or in part) the substance or substance activity or function.

The term "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

In some embodiments, the cancer is one in which at least one of HSP70, vimentin or HSP90 expression is upregulated (overexpressed). For example HSP70 is constitutively overexpressed in pancreatic cancer cells (Hyun et al., Gut Liver. 2013 November; 7(6):739-46).

Upregulation of expression comprises expression of at least one of (optionally only one of) HSP70 (e.g., mHSP70), vimentin or HSP90 at a level that is greater than would normally be expected for a cell or tissue of a given type. Upregulation may be determined by determining the level of expression at least one of HSP70, vimentin or HSP90 in a cell or tissue. A comparison may be made between the level of expression in a cell or tissue sample from a subject and a reference level of, e.g. a value or range of values representing a normal level of expression for the same or corresponding cell or tissue type. In some embodiments reference levels may be determined by detecting expression in a control sample, e.g. in corresponding cells or tissue from a healthy subject or from healthy tissue of the same subject. In some embodiments reference levels may be obtained from a standard curve or data set.

Levels of expression may be quantitated for absolute comparison, or relative comparisons may be made.

In some embodiments upregulation of expression may be considered to be present when the level of expression in the test sample is at least 1.1 times that of a reference level. More preferably, the level of expression may be selected from one of at least 1.2, at least 1.3, at least 1.4, at least 1.5, at least 1.6, at least 1.7, at least 1.8, at least 1.9, at least 2.0, at least 2.1, at least 2.2, at least 2.3, at least 2.4 at least 2.5, at least 2.6, at least 2.7, at least 2.8, at least 2.9, at least 3.0, at least 3.5, at least 4.0, at least 5.0, at least 6.0, at least 7.0, at least 8.0, at least 9.0, or at least 10.0 times that of the reference level.

Expression levels may be determined by one of a number of known in vitro assay techniques, such as PCR based assays, in situ hybridisation assays, flow cytometry assays, immunological or immunohistochemical assays.

By way of example suitable techniques involve a method of detecting the level of at least one of (optionally only one of) HSP70, vimentin or HSP90 in a sample by contacting the sample with an agent capable of binding at least one of HSP70, vimentin or HSP90 and detecting the formation of a complex of the agent and at least one of HSP70, vimentin or HSP90. The agent may be any suitable binding molecule, e.g. an antibody, polypeptide, peptide, oligonucleotide, aptamer or small molecule, and may optionally be labelled to permit detection, e.g. visualisation, of the complexes formed. Suitable labels and means for their detection are well known to those in the art and include fluorescent labels (e.g. fluorescein, rhodamine, eosine and NDB, green fluorescent protein (GFP), chelates of rare earths such as europium (Eu), terbium (Tb) and samarium (Sm), tetramethyl rhodamine, Texas Red, 4-methyl umbelliferone, 7-amino-4-methyl coumarin, Cy3, Cy5), isotope markers, radioisotopes (e.g. $^{32}$P, $^{33}$P, $^{35}$S), chemiluminescence labels (e.g. acridinium ester, luminol, isoluminol), enzymes (e.g. peroxidase, alkaline phosphatase, glucose oxidase, beta-galactosidase, luciferase), antibodies, ligands and receptors. Detection techniques are well known to those of skill in the art and can be selected to correspond with the labelling agent. Suitable techniques include PCR amplification of oligonucleotide tags, mass spectrometry, detection of fluorescence or colour, e.g. upon enzymatic conversion of a substrate by a reporter protein, or detection of radioactivity.

Assays may be configured to quantify the amount of at least one of HSP70, vimentin or HSP90 in a sample. Quantified amounts from a test sample may be compared with reference values, and the comparison used to determine whether the test sample contains an amount of at least one of HSP70, vimentin or HSP90 that is higher or lower than that of the reference value to a selected degree of statistical significance.

Quantification of detected HSP70, vimentin or HSP90 may be used to determine up- or down-regulation or amplification of genes encoding HSP70, vimentin or HSP90.

"Anticancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anticancer agent is an agent identified herein having utility in methods of treating cancer. In embodiments, an anticancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analogue (e.g., methotrexate), or pyrimidine analogues (e.g., fluorouracil, floxouridine, Cytarabine, 6-azauracil), purine analogues (e.g., mercaptopurine, thioguanine, pentostatin), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), or adrenocortical suppressant (e.g., mitotane, aminoglutethimide), epipodophyllotoxins (e.g., etoposide).

Further examples of anticancer agents include, but are not limited to, antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®), geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein kinase C inhibitors, protein tyrosine phosphatase inhibitors; purine nucleoside phosphorylase inhibitors; ras famesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Gudrin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST- 1306, ARRY334543, ARRY-380, AG-1478, dacomitinib/ PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

Anticancer agents or chemotherapeutic agents may be nucleotide analogues, nucleoside analogues, pyrimidine analogues or purine analogues. A pyrimidine or purine analogue may be combined with a sugar to form a nucleoside analogue which may be combined with one or more phosphate groups to form a nucleotide analogue. An aptamer described herein may incorporate one or more anticancer or chemotherapeutic nucleotide analogues in the oligonucleotide sequence of the aptamer. The anticancer or chemotherapeutic nucleotide analogues may be incorporated by substitution of corresponding non-modified or non-anticancer nucleotides.

The term "nucleotide" typically refers to a compound containing a nucleoside or a nucleoside analogue and at least one phosphate group or a modified phosphate group linked to it by a covalent bond. Exemplary covalent bonds include, without limitation, an ester bond between the 3', 2' or 5' hydroxyl group of a nucleoside and a phosphate group.

The term "nucleoside" refers to a compound containing a sugar part and a nucleobase, e.g. pyrimidine or purine base. Exemplary sugars include, without limitation, ribose, 2-deoxyribose, arabinose and the like. Exemplary nucleobases include, without limitation, thymine, uracil, cytosine, adenine, guanine.

The term "nucleoside analogue" may refer to a nucleoside any part of which is replaced by a chemical group of any nature. Exemplary nucleoside analogues include, without limitation, 2'-substituted nucleosides such as 2'-fluoro, 2-deoxy, 2'-O-methyl, 2'-O-(3-methoxyethyl, 2'-O-allylriboribonucleosides, 2'-amino, locked nucleic acid (LNA) monomers and the like.

The term "nucleoside analogue" may also refer to a nucleoside in which the sugar or base part is modified, e.g. with a non-naturally occurring modification. Exemplary nucleoside analogues in which the sugar part is replaced with another cyclic structure include, without limitation, monomeric units of morpholinos (PMO) and tricyclo-DNA. Exemplary nucleoside analogues in which the sugar part is replaced with an acyclic structure include, without limitation, monomeric units of peptide nucleic acids (PNA) and glycerol nucleic acids (GNA).

Suitably, nucleoside analogues may include nucleoside analogues in which the sugar part is replaced by a morpholine ring as depicted below.

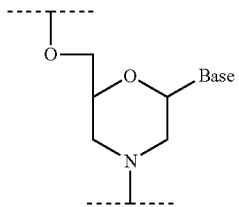

In structures of this type, it will be appreciated that the labels 3' and 5', as applied to conventional sugar chemistry, apply by analogy. That is, in the structure depicted, the hydroxylmethyl substituent on the ring is considered the 5' end, while the third nitrogen valency is considered the 3' end.

Nucleoside analogues may be deoxyadenosine analogues, adenosine analogues, deoxycytidine analogues, cytidine analogues, deoxyguanosine analogues, guanosine analogues, thymidine analogues, 5-methyluridine analogues, deoxyuridine analogues, or uridine analogues. Examples of deoxyadenosine analogues include didanosine (2', 3'-dideoxyinosine) and vidarabine (9-O-D-arabinofuranosyladenine), fludarabine, pentostatin, cladribine. Examples of adenosine analogues include DCX4430 (Immucillin-A). Examples of cytidine analogues include gemcitabine, 5-aza-2'-deoxycytidine, cytarabine. Examples of deoxycytidine analogues include cytarabine, emtricitabine, lamivudine, zalcitabine. Examples of guanosine and deoxyguanosine analogues include abacavir, acyclovir, entecavir. Examples of thymidine and 5-methyluridine analogues include stavudine, telbivudine, zidovudine. Examples of deoxyuridine analogues include idoxuridine, trifluridine.

The terms "purine analogue" or "pyrimdine analogue" refers to modifications, optionally non-naturally occurring modifications, in the nucleobase, for example hypoxanthine, xanthine, 2-aminopurine, 2,6-diaminopurine, 6-azauracil, 5-methylcytosine, 4-fluorouracil, 5-fluoruracil, 5-chlorouracil, 5-bromouracil, 5-iodouracil, 5-trifluoromethyluracil, 5-fluorocytosine, 5-chlorocytosine, 5-bromocytosine, 5-iodocytosine, 5-propynyluracil, 5-propynylcytosine, 7-deazaadenine, 7-deazaguanine, 7-deaza-8-azaadenine, 7-deaza-8-azaguanine, isocytosine, isoguanine, mercaptopurine, thioguanine. Exemplary pyrimidine analogues include, without limitation, 5-position substituted pyrimidines, e.g. substitution with 5-halo, 5'-fluoro. Examples of purine analogues include, without limitation, 6- or 8-position substituted purines, e.g. substitution with 5-halo, 5'-fluoro.

The term "phosphate group" as used herein refers to phosphoric acid $H_3PO_4$ wherein any hydrogen atoms are replaced by one, two or three organic radicals to give a phosphoester, phosphodiester, or phosphotriester, respectively. Oligonucleotides may be linked by phosphodiester, phosphorothioate or phosphorodithioate linkages.

In aptamers described herein, one or more or each adenine, adenosine or deoxyadenosine in the aptamer oligonucleotide sequence may be replaced, e.g. substituted, with an adenine, adenosine or deoxyadenosine analogue, preferably an anticancer analogue.

In aptamers described herein, one or more or each cytosine, cytidine or deoxycytidine in the aptamer oligonucleotide sequence may be replaced, e.g. substituted, with a cytosine analogue, cytidine analogue or deoxycytidine analogue, preferably an anticancer analogue.

In aptamers described herein, one or more or each guanine, guanosine or deoxyguanosine in the aptamer oligonucleotide sequence may be replaced, e.g. substituted, with a guanine, guanosine or deoxyguanosine analogue, preferably an anticancer analogue.

In aptamers described herein, one or more or each thymine, 5-methyluridine or thymidine in the aptamer oligonucleotide sequence may be replaced, e.g. substituted, with a thymine, 5-methyluridine or thymidine analogue, preferably an anticancer analogue.

In aptamers described herein, one or more or each uracil, uridine or deoxyuridine in the aptamer oligonucleotide sequence may be replaced, e.g. substituted, with a uracil, uridine or deoxyuridine analogue, preferably an anticancer analogue.

"Chemotherapeutic" or "chemotherapeutic agent" is used in accordance with its plain ordinary meaning and refers to a chemical composition or compound having antineoplastic properties or the ability to inhibit the growth or proliferation of cells.

Additionally, the compositions described herein can be co-administered with or covalently attached to conventional immunotherapeutic agents including, but not limited to, immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, anti-PD-1 and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compositions described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The term "sample" includes sections of tissues such as biopsy and autopsy samples, and frozen sections taken for histological purposes. Such samples include blood and blood fractions or products (e.g., bone marrow, serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. Contacting may include allowing two species to react, interact, or physically touch, wherein the two species may be a nucleic acid compound as described herein and a cell (e.g., cancer cell).

Compositions

In embodiments, the compositions described herein, including embodiments thereof, are useful in treating various types of cancers, including particularly aggressive cancers that are undifferentiated and/or metastatic. Many existing anticancer agents, such as gemcitabine, are not effective in cancer patients due to, for example: high toxicity of the agents, poor uptake of the agents into cancer cells, lack of specificity of uptake of the agents into cancer cells (alternatively, non-specific uptake of the agents into non-cancer cells), lower metabolic rate (or poor metabolism) of the agents into active forms in cancer cells. These problems and others are addressed herein.

In a first aspect, there is provided a composition including an aptamer and an anticancer agent, where the aptamer is bound to the anticancer agent.

In embodiments, the anticancer agent is a small molecule, a nucleotide analogue, a nucleic acid, or a peptide. In embodiments, the anticancer agent is a small molecule. In embodiments, the anticancer agent is a nucleotide analogue, a nucleoside analogue, a pyrimidine analogue or a purine analogue. In embodiments, the anticancer agent is a nucleic acid. In embodiments, the anticancer agent is a peptide.

In embodiments, the small molecule is pyrrolobenzodiazepine (PBD), monomethyl auristatin E (MMAE), drug maytansinoids 1 (DM1), oxaliplatin, irinotecan or doxorubicin, as known in the art.

In embodiments, the small molecule is bound to the aptamer via a linker. In embodiments, the linker is a first nucleic acid hybridized to a second nucleic acid (also called "sticky bridge" or "hybridized linker"), where the first nucleic acid is covalently bound to the anticancer agent and the second nucleic acid is covalently bound to the aptamer. In embodiments, the small molecule is covalently bound to the aptamer using conjugate chemistry as described above, including, but not limited to, nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition).

A sticky bridge (hybridized linker) comprises an oligonucleotide ("sticky sequence," "hybridization sequence" or "sticky end") positioned at the 3'- or 5'-end of a first aptamer oligonucleotide sequence. A complementary oligonucleotide ("sticky sequence," "hybridization sequence" or "sticky end") is positioned at the end of the anticancer agent. The complementary hybridization sequences are allowed to hybridize and form a non-covalent complex comprising the aptamer and the anticancer agent. The hybridization sequence may be GC or AU rich. Each hybridization sequence may comprise about 16 nucleotides, e.g. 14 to 20 nucleotides or one of 14, 15, 16, 17, 18, 19 or 20 nucleotides. Examples of complementary pairs of hybridization sequences are shown in sequences of SEQ ID Nos: 9-15.

A polycarbon linker may be incorporated between the hybridization sequence (also referred to herein as the first hybridization sequence) and aptamer oligonucleotide sequence and between the hybridization sequence (also referred to herein as the second hybridization sequence) and the anticancer agent. The polycarbon linker provides rigidity to the aptamer, decreasing the likelihood that the inclusion of the additional hybridization sequences will interfere with proper aptamer folding (e.g. see Zhou J, Swiderski P, Li H, et al. Selection, characterization and application of new RNA HIV gp 120 aptamers for facile delivery of Dicer substrate siRNAs into HIV infected cells. *Nucleic Acids Res.* 2009; 37(9):3094-3109).

The polycarbon linker may comprise one or more of an oligonucleotide sequence, hydrocarbon spacer elements such as optionally substituted $C_{1-30}$ alkyl or optionally substituted $C_{2-30}$ alkenyl; or polyethylene glycol molecule(s). In some embodiments the polycarbon linker may be a polycarbon linker, consistent with formation of a "hybridized linker". The polycarbon linker may be an optionally substituted $C_{10-30}$ alkyl, optionally substituted $C_{10-15}$ alkyl, optionally substituted $C_{15-20}$ alkyl, optionally substituted $C_{20-25}$ alkyl, optionally substituted $C_{25-30}$ alkyl, optionally substituted $C_{10-30}$ alkenyl, optionally substituted $C_{10-15}$ alkenyl, optionally substituted $C_{15-20}$ alkenyl, optionally substituted $C_{20-25}$ alkenyl, optionally substituted $C_{25-30}$ alkenyl.

In embodiments, the linker may include or have the structure below. In embodiments, the linker connects with the 3' phosphate of the guanine on one end and the 5' phosphate of the thymidine on the other end, and the nucleobases may be modified.
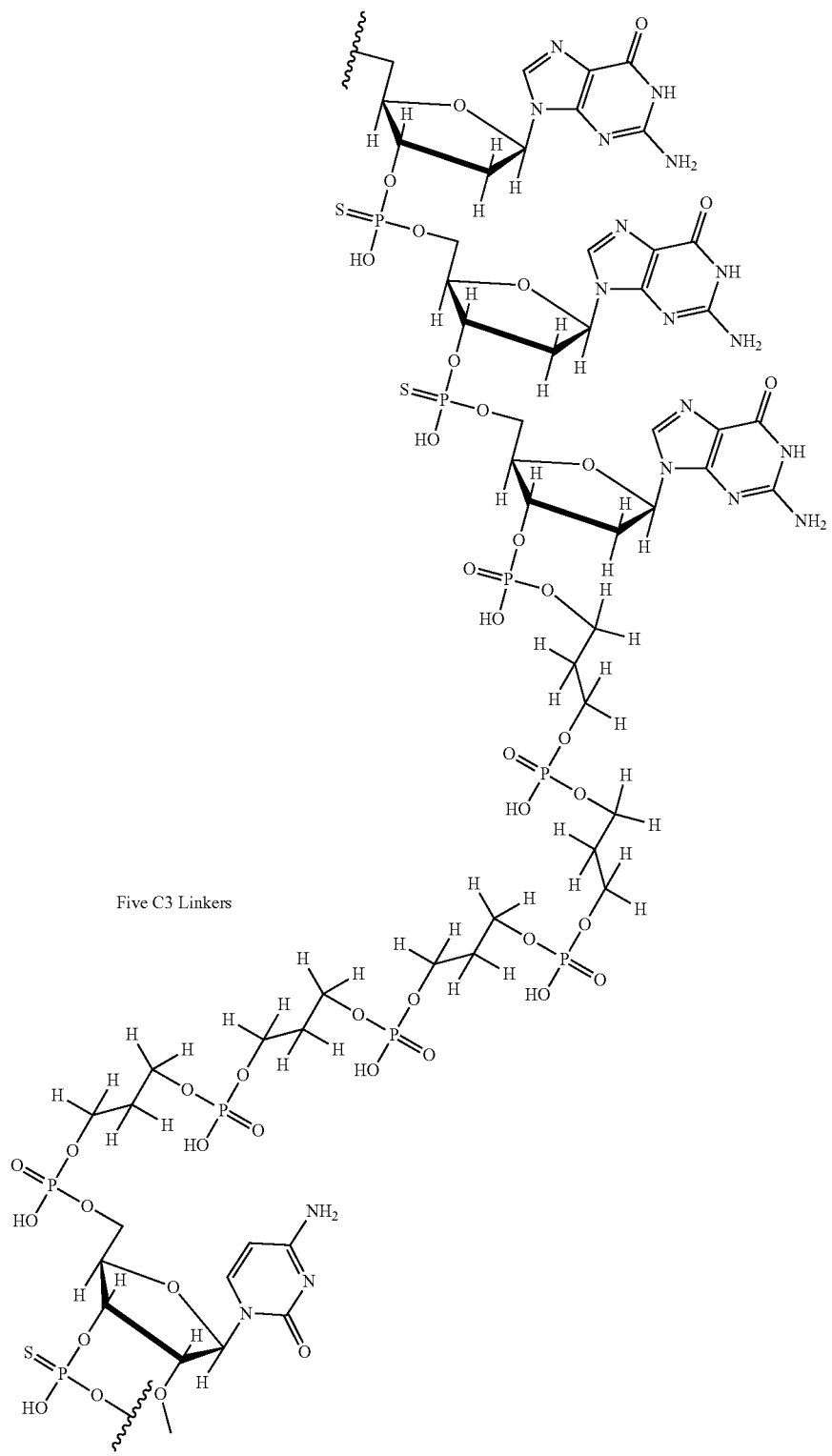
Five C3 Linkers In embodiments, the above formula represents a portion of an aptamer linked at the 3'-OH end with a (CH$_2$)$_3$ linker, which links to the 5'-phosphate of the hybridization sequence (i.e. sticky bridge, sticky sequence).

The linker may be a bond, substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, substituted (e.g. substituted with a substituent group, size-limited substituent group or lower substituent group) or unsubstituted heteroarylene, substituted (e.g. substituted with a substituent group, size-limited substituent group or lower substituent group) or unsubstituted cyclo-heteroalkylene or —(CH$_2$)$_n$—PO$_4$—[(CH$_2$)$_n$—PO$_4$]$_z$—(CH$_2$), in which the symbol n is an integer from 1 to 5 (e.g., 3) and the symbol z is an integer from 0 to 50 (e.g. from 0 to 25, 0 to 10, or 0 to 5). In embodiments, n is 3 and z is 0 to 5 or 1 to 5. In embodiments, n is 3 and z is 0 to 4 or 1 to 4. In embodiments, n is 3 and z is 0 to 3 or 1 to 3. In embodiments, n is 3 and z is 3. Linkers may be added during the synthesis in sequence.

In embodiments, the linker is a covalent linker (i.e. a linker that covalently attaches at least two (e.g. 2) portions of a compound). In embodiments, the linker is or includes a substituted (e.g. substituted with a substituent group, size-limited substituent group or lower substituent group) or unsubstituted alkylene or heteroalkylene linker. In embodiments, heteroalkylene linkers are connected to each other with an intervening phosphate bond. In embodiments, the covalent linker is a substituted (e.g. substituted with a substituent group, size-limited substituent group or lower substituent group) or unsubstituted heteroalkylene linker.

In embodiments, the linker is a substituted (e.g. substituted with a substituent group, size-limited substituent group or lower substituent group) or unsubstituted heteroalkylene or substituted (e.g. substituted with a substituent group, size-limited substituent group or lower substituent group) or unsubstituted cyclo-heteroalkylene. A "cyclo-heteroalkylene," as used herein is a heteroalkylene having a one or more divalent cyclic moieties within the heteroalkylene chain. The cyclic moiety may be a substituted (e.g. substituted with a substituent group, size-limited substituent group or lower substituent group) or unsubstituted cycloalklylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene or substituted (e.g. substituted with a substituent group, size-limited substituent group or lower substituent group) or unsubstituted heteroarylene. In embodiments, the cyclic moiety is a substituted (e.g. substituted with a substituent group, size-limited substituent group or lower substituent group) or unsubstituted ribose (e.g., a nucleoside). In embodiments, the cyclic moiety serves as a branch point of the linker thereby forming a branched linker. The cyclic moiety branch point may be used to attach additional functional moieties to the conjugates provided herein, such as detectable moieties, drug moieties or biomolecule.

In embodiments, the linker includes one or more C3 linkers as set forth in the above structure. In embodiment, a C3 linker is or contains a —(CH$_2$)$_n$—PO$_4$— moiety. In embodiments, the linker is or contains a moiety having the formula:

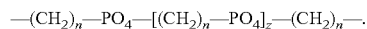

—(CH$_2$)$_n$—PO$_4$—[(CH$_2$)$_n$—PO$_4$]$_z$—(CH$_2$)$_n$—.

In the formula above, the symbol n is an integer from 1 to 5 (e.g., 3) and the symbol z is an integer from 0 to 50 (e.g. from 0 to 25, 0 to 10, or 0 to 5). In embodiments, n is 3 and z is 0 to 5 or 1 to 5. In embodiments, n is 3 and z is 0 to 4 or 1 to 4. In embodiments, n is 3 and z is 0 to 3 or 1 to 3. In embodiments, n is 3 and z is 3.

For example, the linker may have the structure below, where the linker connects with the 3' phosphate of the guanine on one end and the 5' phosphate of the thymidine on the other end:

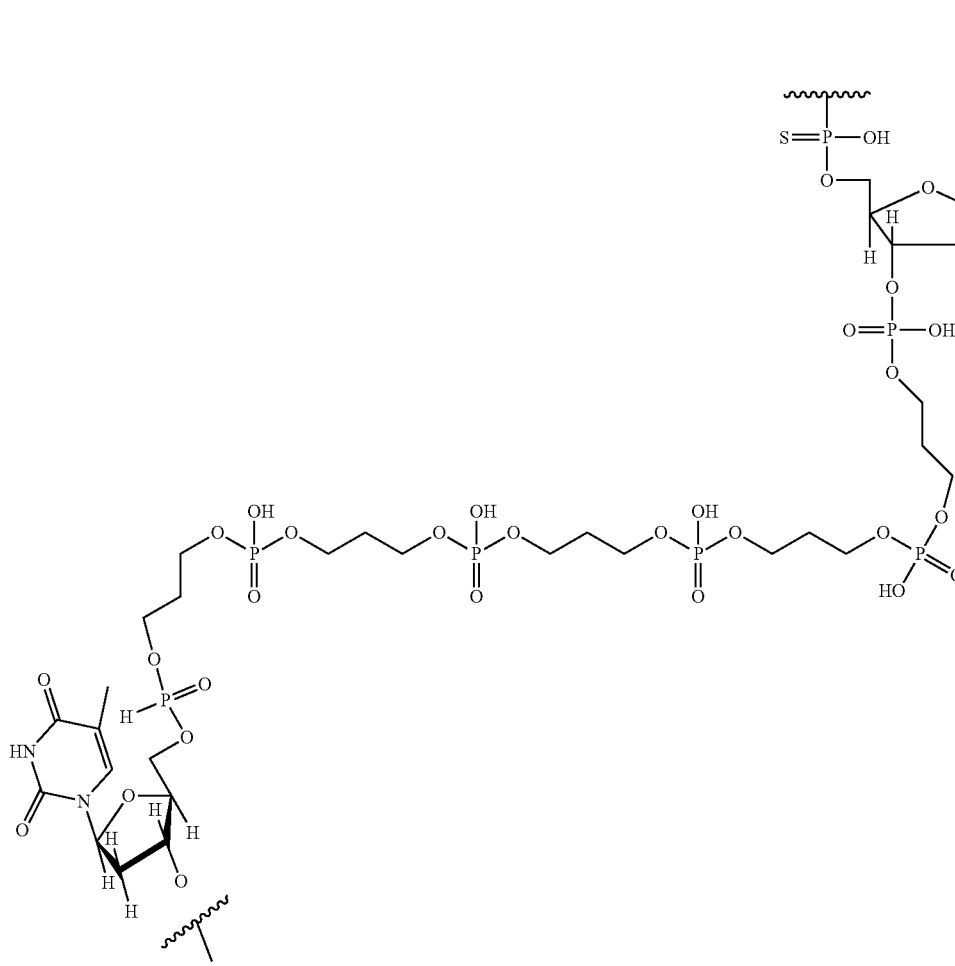

In embodiments, linker may include an unsubstituted $C_3$ heteroalkylene.

In embodiments, linker may include an unsubstituted $C_6$ to $C_{12}$ heteroalkylene.

In embodiments, the linker includes an unsubstituted $C_3$ alkylene (e.g. as described above). In embodiments, the linker may be unsubstituted $C_{15}$ alkylene. In embodiments, the linker includes an unsubstituted $C_6$ to $C_{16}$ alkylene. In embodiments, the linker may be a substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, or substituted (e.g. substituted with a substituent group, size-limited substituent group or lower substituent group) or unsubstituted heteroarylene. In embodiments, the linker may be a substituted (e.g. substituted with a substituent group, size-limited substituent group or lower substituent group) or unsubstituted $C_1$-$C_{40}$ alkylene, substituted (e.g. substituted with a substituent group, size-limited substituent group or lower substituent group) or unsubstituted 2 to 40 membered heteroalkylene, substituted (e.g. substituted with a substituent group, size-limited substituent group or lower substituent group) or unsubstituted $C_3$-$C_8$ cycloalkylene, substituted (e.g. substituted with a substituent group, size-limited substituent group or lower substituent group) or unsubstituted 3 to 8 membered heterocycloalkylene, substituted (e.g. substituted with a substituent group, size-limited substituent group or lower substituent group) or unsubstituted $C_6$-$C_{10}$ arylene, or substituted (e.g. substituted with a substituent group, size-limited substituent group or lower substituent group) or unsubstituted 5 to 10 membered heteroarylene. In embodiments, the linker may be an unsubstituted $C_1$-$C_{40}$ alkylene, unsubstituted 2 to 40 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In embodiments, the linker may be a substituted (e.g. substituted with a substituent group, size-limited substituent group or lower substituent group) 2 to 40 membered heteroalkylene.

A linker may be a bond, nucleic acid sequence, two nucleic acid sequences, DNA sequence, two DNA sequences, nucleic acid analog sequence, substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, or substituted (e.g. substituted with a substituent group, size-limited substituent group or lower substituent group) or unsubstituted heteroarylene.

In embodiments, the linker is or contains a substituted (e.g. substituted with a substituent group, size-limited substituent group or lower substituent group) or unsubstituted alkylene, substituted (e.g. substituted with a substituent group, size-limited substituent group or lower substituent group) or unsubstituted heteroalkylene, substituted (e.g. substituted with a substituent group, size-limited substituent group or lower substituent group) or unsubstituted cycloalkylene, substituted (e.g. substituted with a substituent group, size-limited substituent group or lower substituent group) or unsubstituted heterocycloalkylene, substituted (e.g. substituted with a substituent group, size-limited substituent group or lower substituent group) or unsubstituted arylene, or substituted (e.g. substituted with a substituent group, size-limited substituent group or lower substituent group) or unsubstituted heteroarylene. In embodiments, the linker is a substituted (e.g. substituted with a substituent group, size-limited substituent group or lower substituent group) or unsubstituted $C_1$-$C_{20}$ alkylene, substituted (e.g. substituted with a substituent group, size-limited substituent group or lower substituent group) or unsubstituted 2 to 20 membered heteroalkylene, substituted (e.g. substituted with a substituent group, size-limited substituent group or lower substituent group) or unsubstituted $C_3$-$C_8$ cycloalkylene, substituted (e.g. substituted with a substituent group, size-limited substituent group or lower substituent group) or unsubstituted 3 to 8 membered heterocycloalkylene, substituted (e.g. substituted with a substituent group, size-limited substituent group or lower substituent group) or unsubstituted $C_6$-$C_{10}$ arylene, or substituted (e.g. substituted with a substituent group, size-limited substituent group or lower substituent group) or unsubstituted 5 to 10 membered heteroarylene. In embodiments, the linker is an unsubstituted $C_1$-$C_{20}$ alkylene, unsubstituted 2 to 20 membered heteroalkylene, unsubstituted $C_3$-$C_8$ cycloalkylene, unsubstituted 3 to 8 membered heterocycloalkylene, unsubstituted $C_6$-$C_{10}$ arylene, or unsubstituted 5 to 10 membered heteroarylene. In embodiments, the linker is an unsubstituted $C_1$-$C_{20}$ alkylene. In embodiments, the linker is a substituted (e.g. substituted with a substituent group, size-limited substituent group or lower substituent group) or unsubstituted $C_1$-$C_{40}$ alkylene, substituted (e.g. substituted with a substituent group, size-limited substituent group or lower substituent group) or unsubstituted 2 to 40 membered heteroalkylene, substituted (e.g. substituted with a substituent group, size-limited substituent group or lower substituent group) or unsubstituted $C_3$-$C_8$ cycloalkylene, substituted (e.g. substituted with a substituent group, size-limited substituent group or lower substituent group) or unsubstituted 3 to 8 membered heterocycloalkylene, substituted (e.g. substituted with a substituent group, size-limited substituent group or lower substituent group) or unsubstituted $C_6$-$C_{10}$ arylene, or substituted (e.g. substituted with a substituent group, size-limited substituent group or lower substituent group) or unsubstituted 5 to 10 membered heteroarylene. In embodiments, the linker is a substituted (e.g. substituted with a substituent group, size-limited substituent group or lower substituent group) or unsubstituted $C_1$-$C_{40}$ alkylene. In embodiments, the linker is a substituted (e.g. substituted with a substituent group, size-limited substituent group or lower substituent group) or unsubstituted 2 to 40 membered heteroalkylene. In embodiments, the linker is a substituted (e.g. substituted with a substituent group, size-limited substituent group or lower substituent group) 2 to 40 membered heteroalkylene. In embodiments, the linker includes alkyl phosphates (e.g., propyl phosphates). In embodiments, the linker has alkyl phosphates (e.g., propyl phosphates) bonded to the reminder of the compound by phosphates at both ends. In embodiments, the linker has 1-5 alkyl phosphates (e.g., propyl phosphates) bonded to the reminder of the compound by phosphates at both ends. In embodiments, the linker has 1-4 alkyl phosphates (e.g., propyl phosphates) bonded to the reminder of the compound by phosphates at both ends. In embodiments, the linker has 4 alkyl phosphates (e.g., propyl phosphates) bonded to the reminder of the compound by phosphates at both ends. A person having ordinary skill in the art will recognize that a linker having alkyl phosphates that is bonded to the remainder of the compound by phosphates on both ends will have one more phosphate than alkylene groups (e.g., a linker having 4 alkyl phosphates that is bonded to the reminder of the compound by phosphates at both ends will have five phosphates and four alkyl groups with alternating phosphate groups and alkyl groups).

Accordingly, a composition described herein may include an aptamer, comprising one of SEQ ID Nos 1 to 8, covalently conjugated at the 3' or 5' end to a hybridized linker, optionally via a polycarbon spacer (e.g., alkylene or heteroalkylene), complexed with an anticancer agent covalently conjugated at the end to a complementary hybridized linker, optionally via a polycarbon spacer (e.g., alkylene or heteroalkylene).

Figure 5A:
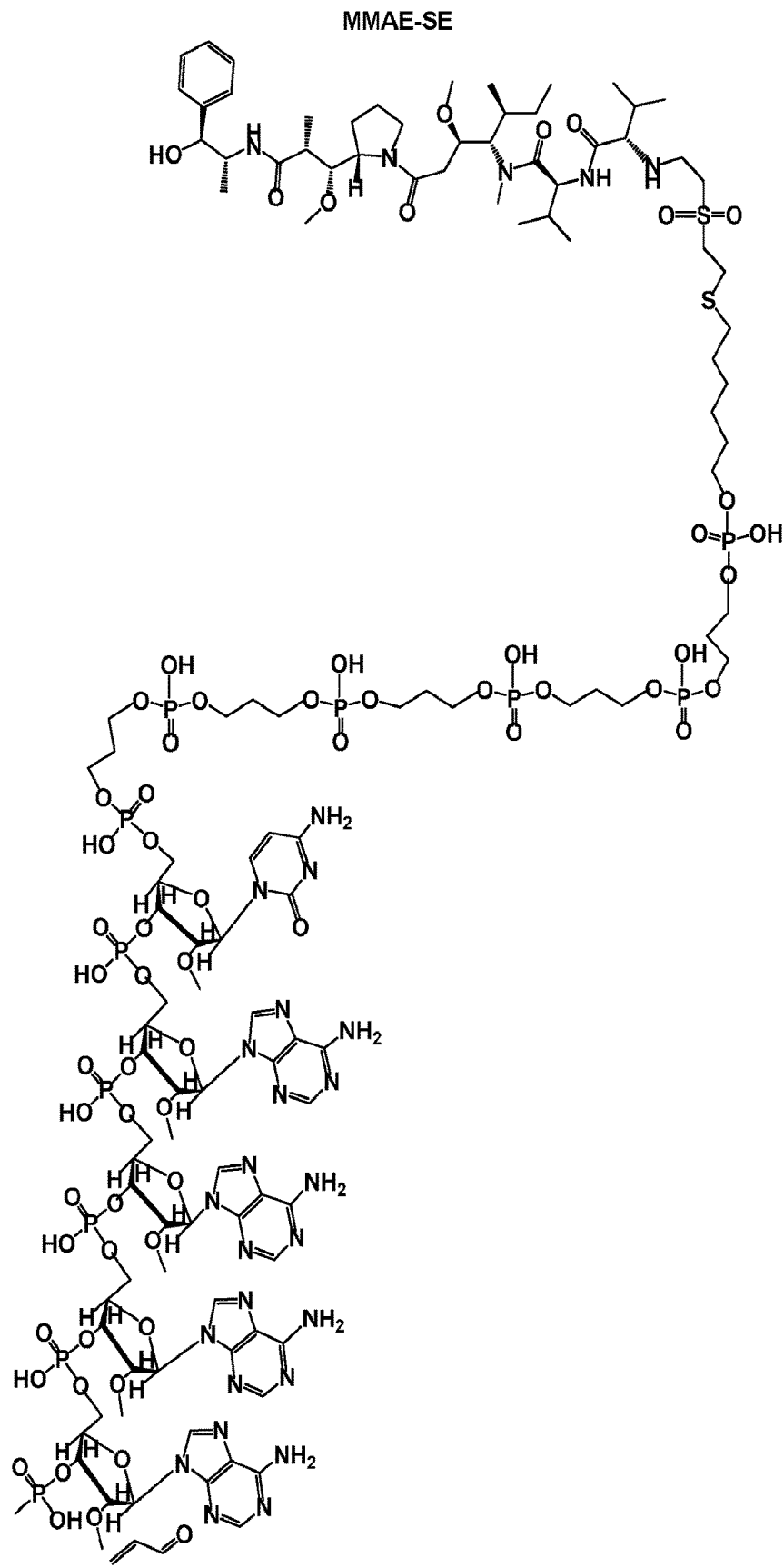
FIGS. 5A-5D. Aptamer drug conjugations (ApDCs) of MMAE and DM1.
Figure 5B:
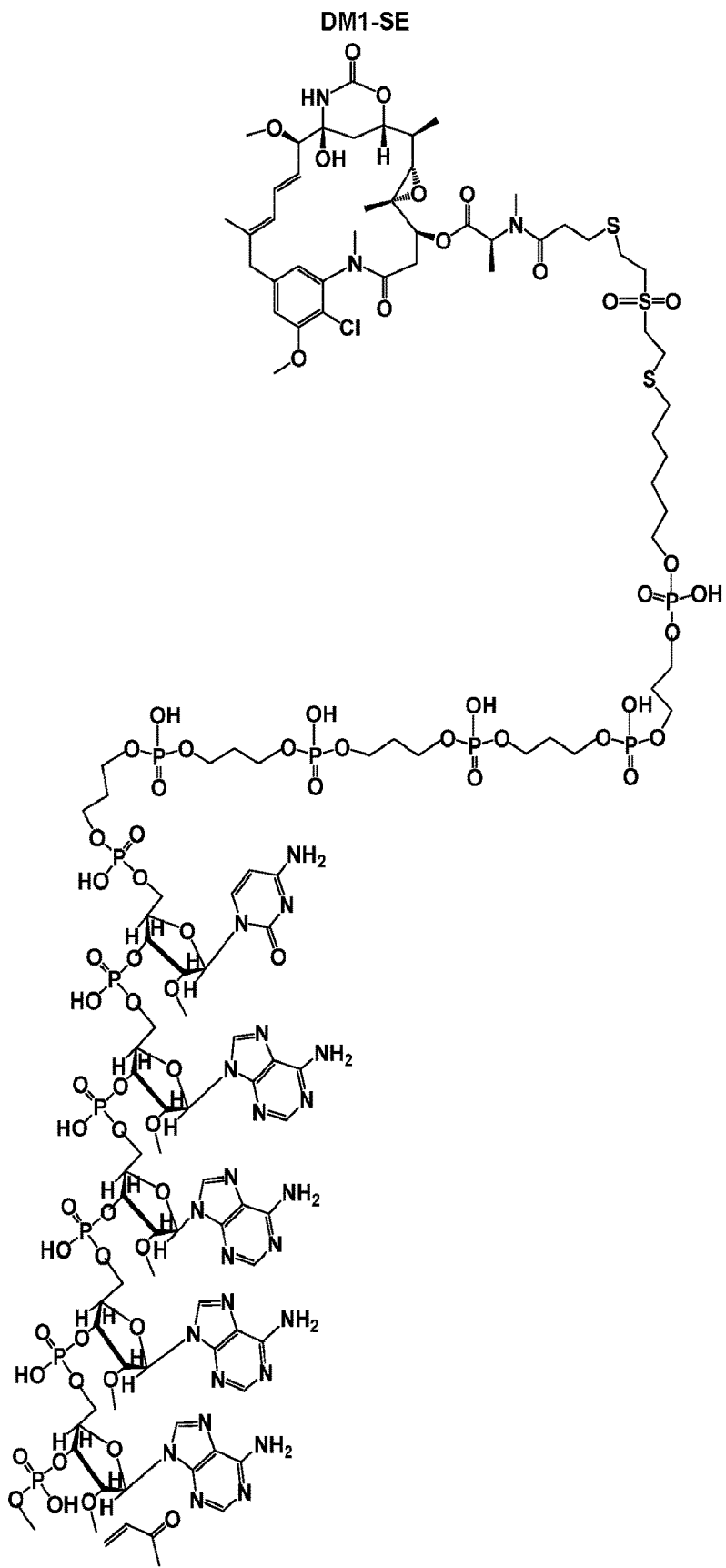
Figure 5C:
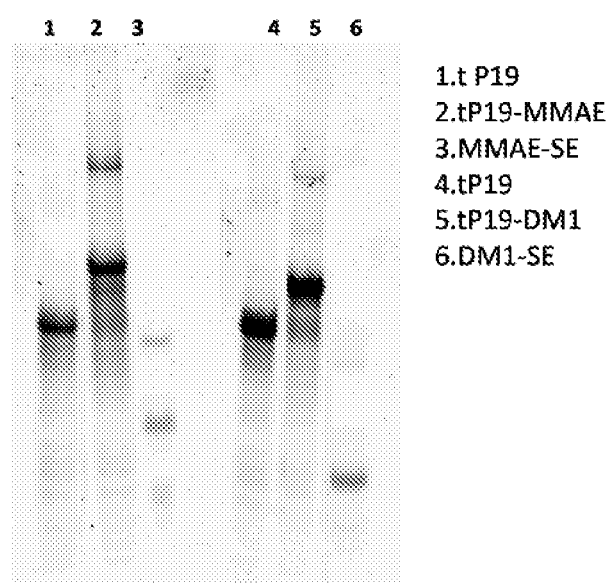
Figure 5D:
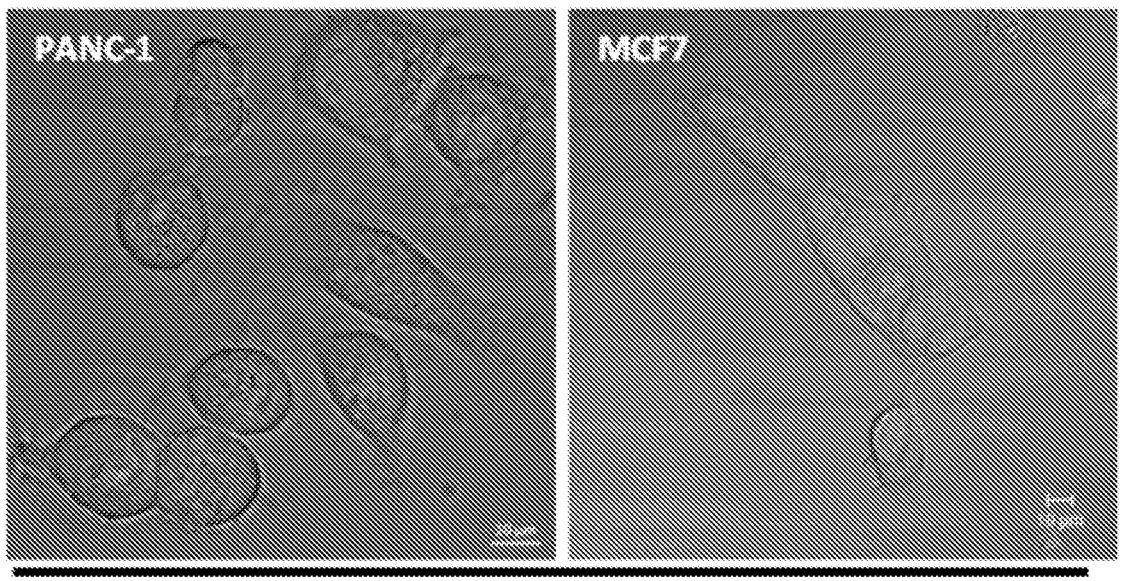
Figure 5D:
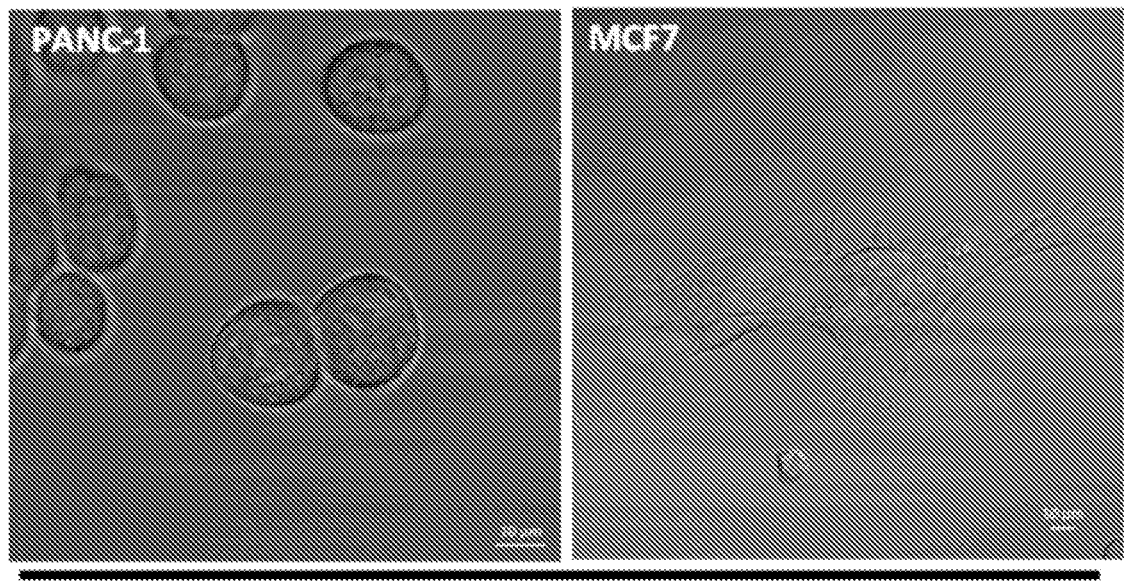
Figure 6:
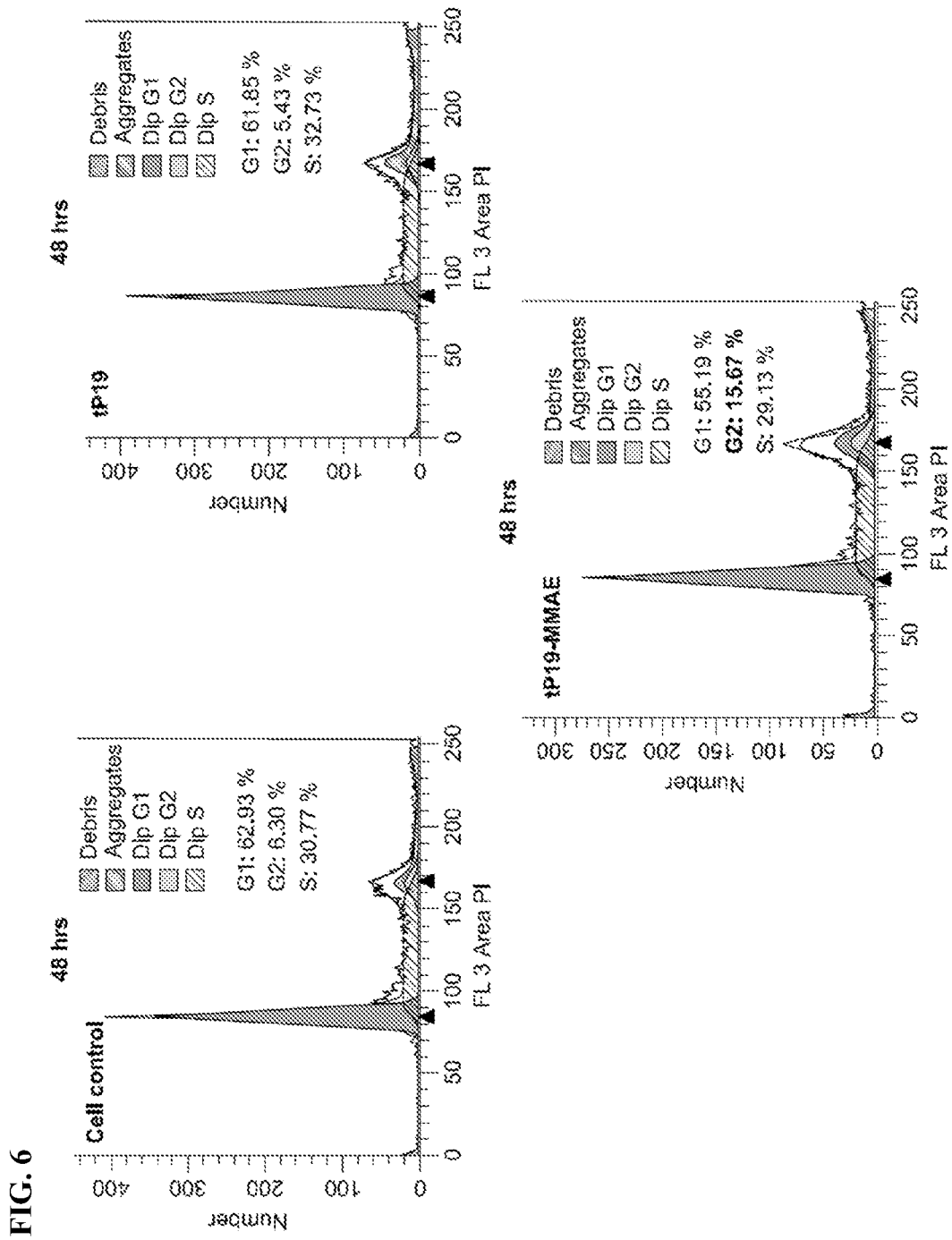
FIG. 6. DNA content histograms. PANC-1 cells treated with MMAE-tP19-ApDC were stained with PI and analyzed at 48 hrs and 72 hrs, as indicated. Fluorescence of the PI-stained cells was measured with flow cytometry and ModFit deconvolution software. The software programs indicate the percentage of cell with fractional DNA contents and cells in $G_1$, S, and $G_2$/M phases of the cycle.
Figure 6:
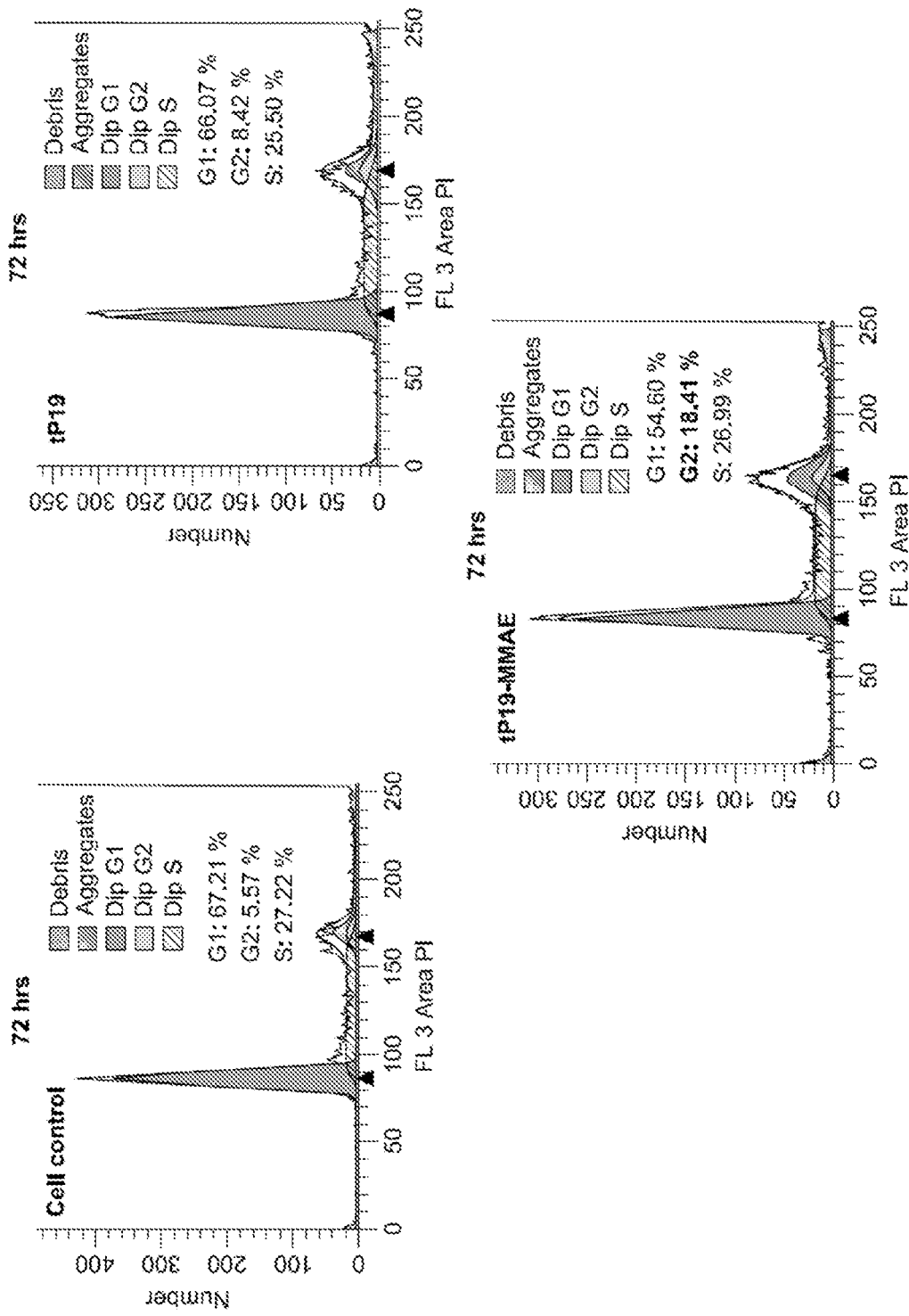
Figure 7A:
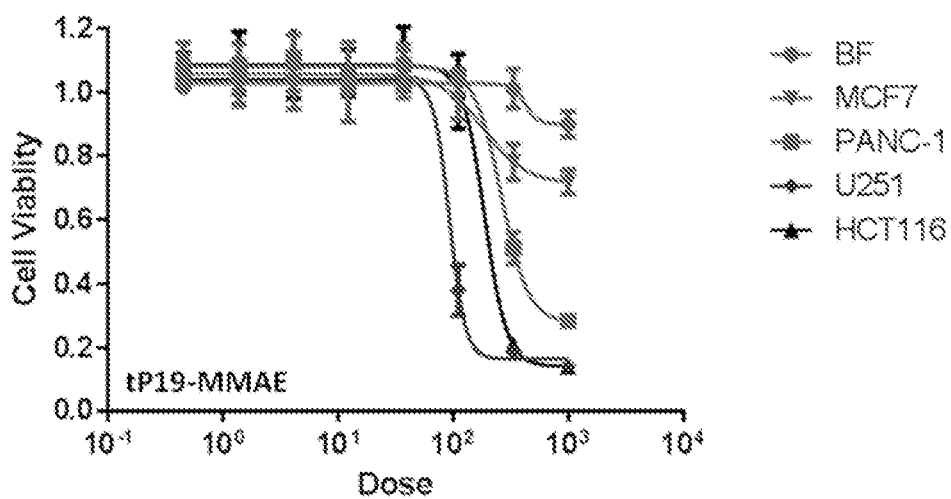
FIGS. 7A-7B. Cell proliferation assay of MMAE-tP19-ApDC and DM1-tP19-ApDC.
Figure 7B:
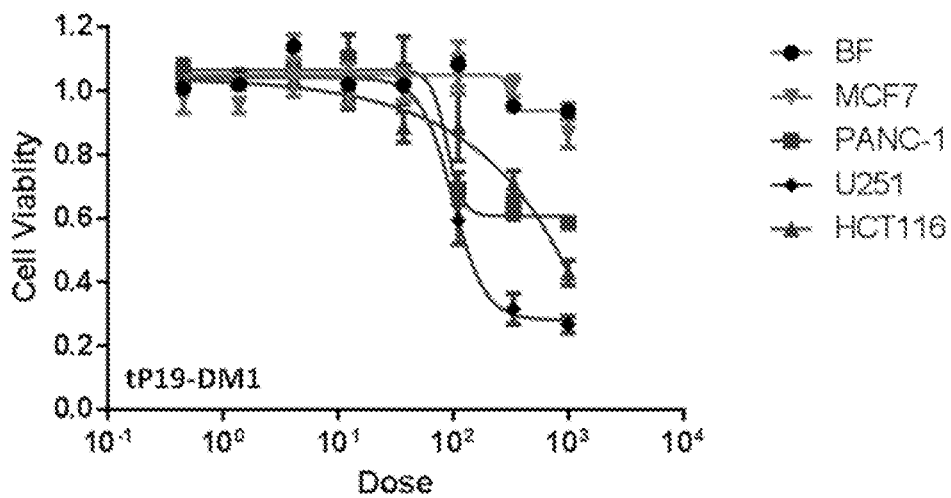
Figure 8:
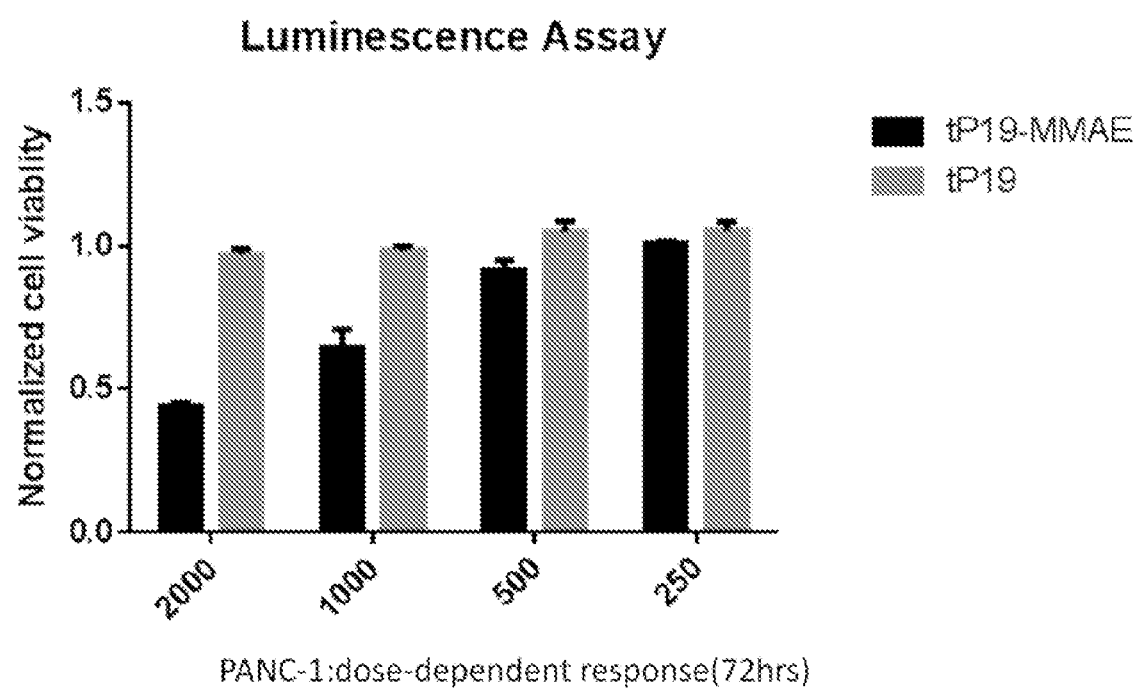
FIG. 8. Dose-dependent cytotoxicity of tP19-MMAE in pancreatic cancer cells. tP19-MMAE is more toxic than tP19 alone. Cell viability was measured in PANC-1 at 72 hr by luminescence assay. Dosing as indicated in graphs.
Figure 9:
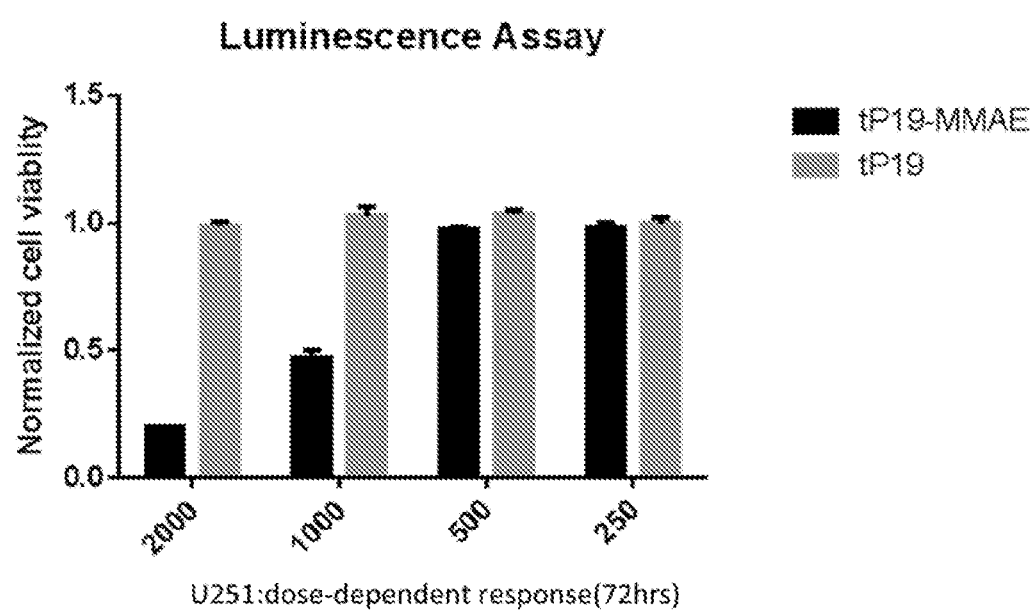
FIG. 9. Dose-dependent cytotoxicity of tP19-MMAE in glioblastoma. Figure depicts histograms of cell proliferation (cell viability) as a function of the indicated dose of agent. Cell viability was measured in U251 at 72 hr by luminescence assay. Dosing as indicated in graphs FIG. 10. MEDUSA combination strategies. Figure depicts that aptamers can be combined with multiple cytotoxic agents simultaneously for target delivery of chemotherapeutics.
Figure 10:
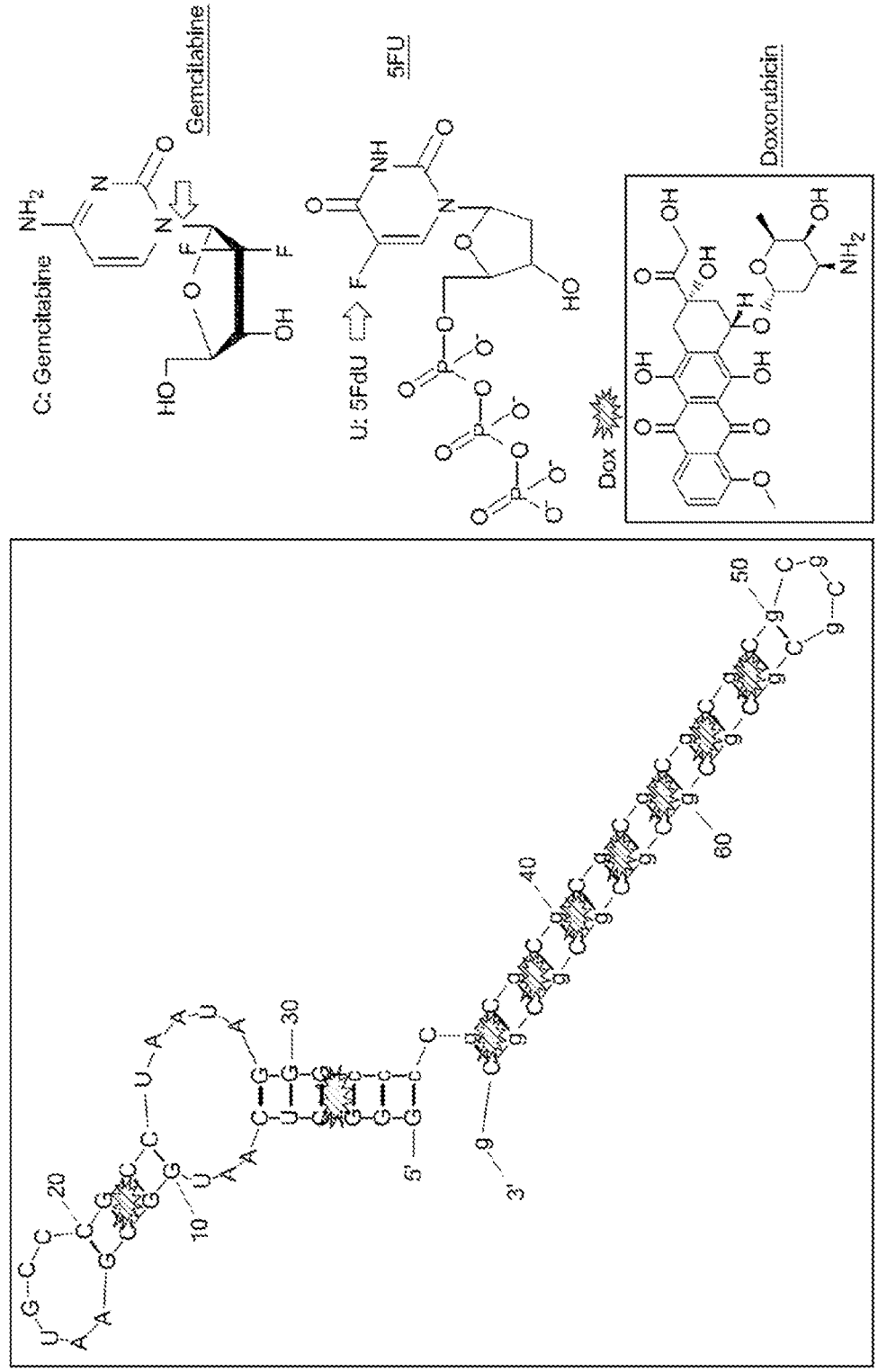

In embodiments, the small molecule is covalently bound to the aptamer directly. For example, the small molecule (e.g., MMAE or DM1) is directly bound to the aptamer via chemical group as illustrated in FIGS. 5A and 5B (the same chemical group that links the small molecule to the hybridization sequence in the figure).

In embodiments, the small molecule is non-covalently bound to the aptamer directly. For example, the small molecule (e.g., doxorubicin) is bound to the aptamer via intercalation. Intercalation, in biochemistry, is the insertion of molecules between the bases of DNA or RNA sequences. In embodiments, doxorubicin is bound to double stranded 5'-GC-3' or 5'-CG-3' sequence of the aptamer sequence. In embodiments, conjugation of doxorubicin to aptamer sequence may be done by incubating aptamer and doxorubicin in buffer, followed by removing unconjugated doxorubicin by cut-off membrane column.

In embodiments, the anticancer agent is a nucleotide analogue, a nucleoside analogue, a pyrimidine analogue or a purine analogue. In embodiments, the nucleotide analogue is gemcitabine monophosphate (dFdCMP) or 5-F-uridine monophosphate (5FdUMP). In embodiments, the nucleoside analogue is gemcitabine. In embodiments, the pyrimidine analogue is 5-FU.

In embodiments, the anticancer agent is present within the nucleic acid sequence of the aptamer.

In embodiments, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100) nucleotides of the aptamer nucleic acid sequence are replaced by one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) either same or different nucleotide analogues (e.g., dFdCMP or 5FdUMP).

In embodiments, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) nucleosides of the aptamer nucleic acid sequence are replaced by one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) either same or different nucleoside analogues (e.g., gemcitabine).

In embodiments, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) pyrimidines of the aptamer nucleic acid sequence are replaced by one or more either same or different pyrimidine analogues (e.g., 5-FU).

In embodiments, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) purines of the aptamer nucleic acid sequence are replaced by one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) either same or different purine analogues.

In embodiments, the anticancer agent is gemcitabine or gemcitabine analogue, where the gemcitabine or gemcitabine analogue is present within the nucleic acid sequence at one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100), or each, cytidine positions. For example, the one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) cytidine nucleotides of the aptamer nucleic acid sequence are replaced by dFdCMP.

In embodiments, the anticancer agent is 5-fluorouracil or 5-fluorouracil analogue, where the 5-fluorouracil or 5-fluorouracil analogue is present within the nucleic acid sequence at one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100), or each, uridine positions. For example, the one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100), or each, uridine nucleotides of the aptamer nucleic acid sequence are replaced by 5FdUMP.

In embodiments, the composition is bound to a cellular receptor. In embodiments, the cellular receptor is cell surface HSP70. In embodiments, the cells surface HSP70 is mHSP70 (mortalin). In embodiments, the cellular receptor is cell surface HSP90. In embodiments, the cellular receptor is cell surface vimentin. In embodiments, the cellular receptor is present on a cancer cell. In embodiments, the cancer cell is a cancer stem cell. In embodiments, the cancer cell is an undifferentiated cancer cell. In embodiments, the cancer cell is an undifferentiated metastatic cancer cell. In embodiments, the cancer cell is a pancreatic cancer cell, a glioblastoma cell, or a colon cancer cell.

Further to any embodiment of the composition disclosed herein, in embodiments the aptamer includes or has a nucleic acid sequence of one of SEQ ID Nos: 1 to 7. In embodiments, the aptamer includes a nucleic acid sequence having at least 80% sequence identity to one of SEQ ID NOS: 1 to 7. In embodiments, the aptamer includes a nucleic acid sequence of SEQ ID NO:8.

Where a nucleic acid sequence has at least 80% (80% or more) sequence identity to a given sequence, the nucleic acid sequence may have 80%, 85%, 90%, 91%, 92%, 93%, 94%, 95%, 96%, 97%, 98%, 99% or 100% sequence identity to that sequence. In embodiments, the nucleic acid sequence has at least 80% (80% or more) sequence identity to a nucleic acid that hybridizes to a given sequence. In embodiments, the aptamer includes a nucleic acid sequence having at least 80%, 85%, 90%, 91%, 92%, 93%, 94%, 95%, 96%, 97%, 98%, 99% or 100% sequence identity to SEQ ID NO: 1. In embodiments, the aptamer includes a nucleic acid sequence having at least 80%, 85%, 90%, 91%, 92%, 93%, 94%, 95%, 96%, 97%, 98%, 99% or 100% sequence identity to SEQ ID NO: 2. In embodiments, the aptamer includes a nucleic acid sequence having at least 80%, 85%, 90%, 91%, 92%, 93%, 94%, 95%, 96%, 97%, 98%, 99% or 100% sequence identity to SEQ ID NO: 3. In embodiments, the aptamer includes a nucleic acid sequence having at least 80%, 85%, 90%, 91%, 92%, 93%, 94%, 95%, 96%, 97%, 98%, 99% or 100% sequence identity to SEQ ID NO: 4. In embodiments, the aptamer includes a nucleic acid sequence having at least 80%, 85%, 90%, 91%, 92%, 93%, 94%, 95%, 96%, 97%, 98%, 99% or 100% sequence identity to SEQ ID NO: 5. In embodiments, the aptamer includes a nucleic acid sequence having at least 80%, 85%, 90%, 91%, 92%, 93%, 94%, 95%, 96%, 97%, 98%, 99% or 100% sequence identity to SEQ ID NO: 6. In embodiments, the aptamer includes a nucleic acid sequence having at least 80%, 85%, 90%, 91%, 92%, 93%, 94%, 95%, 96%, 97%, 98%, 99% or 100% sequence identity to SEQ ID NO: 7. In embodiments, the aptamer includes a nucleic acid sequence having at least 80%, 85%, 90%, 91%, 92%, 93%, 94%, 95%, 96%, 97%, 98%, 99% or 100% sequence identity to SEQ ID NO: 8.

In embodiments, the aptamer includes a nucleic acid sequence that is less than 100 nucleotides in length.

Where the nucleic sequence is less than 100 (99 or less) nucleotides in length the sequence is one of 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In embodiments, the nucleic acid sequence is less than 90 nucleotides in length. In embodiments, the nucleic acid sequence is less than 80 nucleotides in length. In embodiments, the nucleic acid sequence is less than 70 nucleotides in length. In embodiments, the nucleic acid sequence is less than 60 nucleotides in length. In embodiments, the nucleic acid sequence is less than 50 nucleotides in length. In embodiments, the nucleic acid sequence is less than 40 nucleotides in length.

In embodiments, the nucleic acid sequence is between 20 and 99 nucleotides in length. In embodiments, the nucleic acid sequence is between 25 and 99 nucleotides in length. In embodiments, the nucleic acid sequence is between 30 and 99 nucleotides in length. In embodiments, the nucleic acid sequence is between 35 and 99 nucleotides in length. In embodiments, the nucleic acid sequence is between 40 and 99 nucleotides in length. In embodiments, the nucleic acid sequence is between 45 and 99 nucleotides in length. In embodiments, the nucleic acid sequence is between 50 and 99 nucleotides in length. In embodiments, the nucleic acid sequence is between 55 and 99 nucleotides in length. In embodiments, the nucleic acid sequence is between 60 and 99 nucleotides in length. In embodiments, the nucleic acid sequence is between 65 and 99 nucleotides in length. In embodiments, the nucleic acid sequence is between 70 and 99 nucleotides in length. In embodiments, the nucleic acid sequence is between 75 and 99 nucleotides in length. In embodiments, the nucleic acid sequence is between 80 and 99 nucleotides in length. In embodiments, the nucleic acid sequence is between 85 and 99 nucleotides in length.

In embodiments, the aptamer includes or has a nucleic acid sequence of SEQ ID NO: 1, and the aptamer is bound to PBD, MMAE, DM1, oxaliplatin, irinotecan or doxorubicin.

In embodiments, the aptamer includes or has a nucleic acid sequence of SEQ ID NO:2, and the aptamer is bound to PBD, MMAE, DM1, oxaliplatin, irinotecan or doxorubicin.

In embodiments, the aptamer includes or has a nucleic acid sequence of SEQ ID NO:3, and the aptamer is bound to PBD, MMAE, DM1, oxaliplatin, irinotecan or doxorubicin.

In embodiments, the aptamer includes or has a nucleic acid sequence of SEQ ID NO:4, and the aptamer is bound to PBD, MMAE, DM1, oxaliplatin, irinotecan or doxorubicin.

In embodiments, the aptamer includes or has a nucleic acid sequence of SEQ ID NO:5, and the aptamer is bound to PBD, MMAE, DM1, oxaliplatin, irinotecan or doxorubicin.

In embodiments, the aptamer includes or has a nucleic acid sequence of SEQ ID NO:6, and the aptamer is bound to PBD, MMAE, DM1, oxaliplatin, irinotecan or doxorubicin.

In embodiments, the aptamer includes or has a nucleic acid sequence of SEQ ID NO:7, and the aptamer is bound to PBD, MMAE, DM1, oxaliplatin, irinotecan or doxorubicin.

In embodiments, the aptamer includes or has a nucleic acid sequence of SEQ ID NO:8, and the aptamer is bound to PBD, MMAE, DM1, oxaliplatin, irinotecan or doxorubicin.

In embodiments, the aptamer includes or has a nucleic acid sequence of SEQ ID NO: 1, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87) nucleotides of the nucleic acid sequence are replaced with a nucleotide analogue.

In embodiments, the aptamer includes or has a nucleic acid sequence of SEQ ID NO: 1, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87), or each, nucleotides of the nucleic acid sequence are replaced with dFdCMP or 5FdUMP.

In embodiments, the aptamer includes or has a nucleic acid sequence of SEQ ID NO: 1, where one or more, or each, cytidine nucleotides (e.g., at positions 7, 17, 19, 21, 26, 28, 35, 36, 37, 40, 41, 49, 52, 58, 59, 62, 63, 69, 76, 78, 80, 83, and 87) are replaced with a nucleotide analogue. In embodiments, the nucleotide analogue is dFdCMP.

In embodiments, the aptamer includes or has a nucleic acid sequence of SEQ ID NO: 1, where one or more (e.g., 1, 2, 3, 4, 5, 6, 7, 8, 9, 10, 11, 12, 13, or 14), or each, uridine nucleotides (e.g., at positions 13, 20, 24, 29, 33, 43, 51, 55, 56, 57, 61, 64, 65, and 77) are replaced with a nucleotide analogue. In embodiments, the nucleotide analogue is 5FdUMP.

In embodiments, the aptamer includes or has a nucleic acid sequence of SEQ ID NO: 1, where one or more (e.g., 1, 2, 3, 4, 5, 6, 7, 8, 9, 10, 11, 12, 13, 14, 15, 16, 17, 18, 19, 20, 21, 22 or 23), or each, nucleotides at positions 7, 17, 19, 21, 26, 28, 35, 36, 37, 40, 41, 49, 52, 58, 59, 62, 63, 69, 76, 78, 80, 83, and 87 of SEQ ID NO: 1 are replaced with dFdCMP.

In embodiments, the aptamer includes or has a nucleic acid sequence of SEQ ID NO: 1, where one or more (e.g., 1, 2, 3, 4, 5, 6, 7, 8, 9, 10, 11, 12, 13 or 14), or each, nucleotides at positions 13, 20, 24, 29, 33, 43, 51, 55, 56, 57, 61, 64, 65, and 77 of SEQ ID NO:1 are replaced with 5FdUMP.

In embodiments, the aptamer includes or has a nucleic acid sequence of SEQ ID NO: 1, where one or more (e.g., 1, 2, 3, 4, 5, 6, 7, 8, 9, 10, 11, 12, 13, 14, 15, 16, 17, 18, 19, 20, 21, 22 or 23), or each, nucleotides at positions 7, 17, 19, 21, 26, 28, 35, 36, 37, 40, 41, 49, 52, 58, 59, 62, 63, 69, 76, 78, 80, 83, and 87 of SEQ ID NO: 1 are replaced with dFdCMP; and one or more (e.g., 1, 2, 3, 4, 5, 6, 7, 8, 9, 10, 11, 12, 13 or 14), or each, nucleotides at positions 13, 20, 24, 29, 33, 43, 51, 55, 56, 57, 61, 64, 65, and 77 of SEQ ID NO:1 are replaced with 5FdUMP.

In embodiments, the aptamer includes or has a nucleic acid sequence of SEQ ID NO: 1, where the nucleotides at positions 7, 17, 19, 21, 26, 28, 35, 36, 37, 40, 41, 49, 52, 58, 59, 62, 63, 69, 76, 78, 80, 83, and 87 of SEQ ID NO: 1 are replaced with dFdCMP.

In embodiments, the aptamer includes or has a nucleic acid sequence of SEQ ID NO: 1, where nucleotides at positions 13, 20, 24, 29, 33, 43, 51, 55, 56, 57, 61, 64, 65, and 77 of SEQ ID NO:1 are replaced with 5FdUMP.

In embodiments, the aptamer includes or has a nucleic acid sequence of SEQ ID NO: 1, where the nucleotides at positions 7, 17, 19, 21, 26, 28, 35, 36, 37, 40, 41, 49, 52, 58, 59, 62, 63, 69, 76, 78, 80, 83, and 87 of SEQ ID NO: 1 are replaced with dFdCMP; and where nucleotides at positions 13, 20, 24, 29, 33, 43, 51, 55, 56, 57, 61, 64, 65, and 77 of SEQ ID NO:1 are replaced with 5FdUMP.

In embodiments, the aptamer includes or has a nucleic acid sequence of SEQ ID NO:2, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87), or each, nucleotides of the nucleic acid sequence are replaced with a nucleotide analogue.

In embodiments, the aptamer includes or has a nucleic acid sequence of SEQ ID NO:2, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87), or each, nucleotides of the nucleic acid sequence are replaced with dFdCMP or 5FdUMP.

In embodiments, the aptamer includes or has a nucleic acid sequence of SEQ ID NO:2, where one or more (e.g., 1, 2, 3, 4, 5, 6, 7, 8, 9, 10, 11, 12, 13, 14, 15, 16, 17, 18, or 19), or each, cytidine nucleotides (e.g., at positions 7, 17, 19, 21, 27, 33, 34, 35, 37, 38, 47, 55, 66, 69, 76, 78, 80, 83, and 87) are replaced with a nucleotide analogue. In embodiments, the nucleotide analogue is dFdCMP.

In embodiments, the aptamer includes or has a nucleic acid sequence of SEQ ID NO:2, where one or more (e.g., 1, 2, 3, 4, 5, 6, 7, 8, 9, 10, 11, 12, 13, 14, 15, or 16), or each, uridine nucleotides (e.g., at positions 13, 20, 24, 31, 39, 42, 49, 50, 52, 56, 57, 59, 60, 64, 65, and 77) are replaced with a nucleotide analogue. In embodiments, the nucleotide analogue is 5FdUMP.

In embodiments, the aptamer includes or has a nucleic acid sequence of SEQ ID NO:2, where one or more (e.g., 1, 2, 3, 4, 5, 6, 7, 8, 9, 10, 11, 12, 13, 14, 15, 16, 17, 18 or 19), or each, nucleotides at positions 7, 17, 19, 21, 27, 33, 34, 35, 37, 38, 47, 55, 66, 69, 76, 78, 80, 83, and 87 of SEQ ID NO:2 are replaced with dFdCMP.

In embodiments, the aptamer includes or has a nucleic acid sequence of SEQ ID NO:2, where one or more (e.g., 1, 2, 3, 4, 5, 6, 7, 8, 9, 10, 11, 12, 13, 14, 15 or 16), or each, nucleotides at positions 13, 20, 24, 31, 39, 42, 49, 50, 52, 56, 57, 59, 60, 64, 65, and 77 of SEQ ID NO:2 are replaced with 5FdUMP.

In embodiments, the aptamer includes or has a nucleic acid sequence of SEQ ID NO:2, where one or more (e.g., 1, 2, 3, 4, 5, 6, 7, 8, 9, 10, 11, 12, 13, 14, 15, 16, 17, 18 or 19), or each, nucleotides at positions 7, 17, 19, 21, 27, 33, 34, 35, 37, 38, 47, 55, 66, 69, 76, 78, 80, 83, and 87 of SEQ ID NO:2 are replaced with dFdCMP; and one or more (e.g., 1, 2, 3, 4, 5, 6, 7, 8, 9, 10, 11, 12, 13, 14, 15 or 16), or each, nucleotides at positions 13, 20, 24, 31, 39, 42, 49, 50, 52, 56, 57, 59, 60, 64, 65, and 77 of SEQ ID NO:2 are replaced with 5FdUMP.

In embodiments, the aptamer includes or has a nucleic acid sequence of SEQ ID NO:2, where the nucleotides at positions 7, 17, 19, 21, 27, 33, 34, 35, 37, 38, 47, 55, 66, 69, 76, 78, 80, 83, and 87 of SEQ ID NO:2 are replaced with dFdCMP.

In embodiments, the aptamer includes or has a nucleic acid sequence of SEQ ID NO:2, where nucleotides at positions 13, 20, 24, 31, 39, 42, 49, 50, 52, 56, 57, 59, 60, 64, 65, and 77 of SEQ ID NO:2 are replaced with 5FdUMP.

In embodiments, the aptamer includes or has a nucleic acid sequence of SEQ ID NO:2, where the nucleotides at positions 7, 17, 19, 21, 27, 33, 34, 35, 37, 38, 47, 55, 66, 69, 76, 78, 80, 83, and 87 of SEQ ID NO:2 are replaced with dFdCMP; and nucleotides at positions 13, 20, 24, 31, 39, 42, 49, 50, 52, 56, 57, 59, 60, 64, 65, and 77 of SEQ ID NO:2 are replaced with 5FdUMP.

In embodiments, the aptamer includes or has a nucleic acid sequence of SEQ ID NO:3, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, or 28), or each, nucleotides of the nucleic acid sequence are replaced with a nucleotide analogue.

In embodiments, the aptamer includes or has a nucleic acid sequence of SEQ ID NO:3, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, or 28), or each, nucleotides of the nucleic acid sequence are replaced with dFdCMP or 5FdUMP.

In embodiments, the aptamer includes or has a nucleic acid sequence of SEQ ID NO:3, where one or more (e.g., 1, 2, 3, 4, 5, 6, 7 or 8), or each, cytidine nucleotides (e.g., at positions 1, 3, 9, 15, 16, 17, 19, and 20) are replaced with a nucleotide analogue. In embodiments, the nucleotide analogue is dFdCMP.

In embodiments, the aptamer includes or has a nucleic acid sequence of SEQ ID NO:3, where one or more (e.g., 1, 2, 3, 4 or 5), or each, uridine nucleotides (e.g., at positions 2, 6, 13, 21, and 24) are replaced with a nucleotide analogue. In embodiments, the nucleotide analogue is 5FdUMP.

In embodiments, the aptamer includes or has a nucleic acid sequence of SEQ ID NO:3, where one or more (e.g., 1, 2, 3, 4, 5, 6, 7 or 8), or each, nucleotides at positions 1, 3, 9, 15, 16, 17, 19, and 20 of SEQ ID NO:3 are replaced with dFdCMP.

In embodiments, the aptamer includes or has a nucleic acid sequence of SEQ ID NO:3, where one or more (e.g., 1, 2, 3, 4 or 5), or each, nucleotides at positions 2, 6, 13, 21, and 24 of SEQ ID NO:3 are replaced with 5FdUMP.

In embodiments, the aptamer includes or has a nucleic acid sequence of SEQ ID NO:3, where one or more (e.g., 1, 2, 3, 4, 5, 6, 7 or 8), or each, nucleotides at positions 1, 3, 9, 15, 16, 17, 19, and 20 of SEQ ID NO:3 are replaced with dFdCMP; and one or more, or each, (e.g., 1, 2, 3, 4 or 5) nucleotides at positions 2, 6, 13, 21, and 24 of SEQ ID NO:3 are replaced with 5FdUMP.

In embodiments, the aptamer includes or has a nucleic acid sequence of SEQ ID NO:3, where nucleotides at positions 1, 3, 9, 15, 16, 17, 19, and 20 of SEQ ID NO:3 are replaced with dFdCMP.

In embodiments, the aptamer includes or has a nucleic acid sequence of SEQ ID NO:3, where nucleotides at positions 2, 6, 13, 21, and 24 of SEQ ID NO:3 are replaced with 5FdUMP.

In embodiments, the aptamer includes or has a nucleic acid sequence of SEQ ID NO:3, where nucleotides at positions 1, 3, 9, 15, 16, 17, 19, and 20 of SEQ ID NO:3 are replaced with dFdCMP; and nucleotides at positions 2, 6, 13, 21, and 24 of SEQ ID NO:3 are replaced with 5FdUMP.

In embodiments, the aptamer includes or has a nucleic acid sequence of SEQ ID NO:4, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87), or each, nucleotides of the nucleic acid sequence are replaced with a nucleotide analogue.

In embodiments, the aptamer includes or has a nucleic acid sequence of SEQ ID NO:4, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87), or each, nucleotides of the nucleic acid sequence are replaced with dFdCMP or 5FdUMP.

In embodiments, the aptamer includes or has a nucleic acid sequence of SEQ ID NO:4, where one or more (e.g., 1, 2, 3, 4, 5, 6, 7, 8, 9, 10, 11, 12, 13, 14, 15, 16, 17, 18, 19 or 20), or each, cytidine nucleotides (e.g., at positions 7, 17, 19, 21, 29, 32, 33, 34, 37, 38, 47, 62, 63, 66, 69, 76, 78, 80, 83, and 87) are replaced with a nucleotide analogue. In embodiments, the nucleotide analogue is dFdCMP.

In embodiments, the aptamer includes or has a nucleic acid sequence of SEQ ID NO:4, where one or more (e.g., 1, 2, 3, 4, 5, 6, 7, 8, 9, 10, 11, 12, 13, 14, 15 or 16), or each, uridine nucleotides (e.g., at positions 13, 20, 26, 27, 40, 41, 42, 45, 46, 52, 55, 57, 60, 64, 65, 77) are replaced with a nucleotide analogue. In embodiments, the nucleotide analogue is 5FdUMP.

In embodiments, the aptamer includes or has a nucleic acid sequence of SEQ ID NO:4, where one or more (e.g., 1, 2, 3, 4, 5, 6, 7, 8, 9, 10, 11, 12, 13, 14, 15, 16, 17, 18, 19 or 20), or each, nucleotides at positions 7, 17, 19, 21, 29, 32, 33, 34, 37, 38, 47, 62, 63, 66, 69, 76, 78, 80, 83, and 87 of SEQ ID NO:4 are replaced with dFdCMP.

In embodiments, the aptamer includes or has a nucleic acid sequence of SEQ ID NO:4, where one or more (e.g., 1, 2, 3, 4, 5, 6, 7, 8, 9, 10, 11, 12, 13, 14, 15 or 16), or each, nucleotides at positions 13, 20, 26, 27, 40, 41, 42, 45, 46, 52, 55, 57, 60, 64, 65, 77 of SEQ ID NO:4 are replaced with 5FdUMP.

In embodiments, the aptamer includes or has a nucleic acid sequence of SEQ ID NO:4, where one or more (e.g., 1, 2, 3, 4, 5, 6, 7, 8, 9, 10, 11, 12, 13, 14, 15, 16, 17, 18, 19 or 20), or each, nucleotides at positions 7, 17, 19, 21, 29, 32, 33, 34, 37, 38, 47, 62, 63, 66, 69, 76, 78, 80, 83, and 87 of SEQ ID NO:4 are replaced with dFdCMP; and one or more (e.g., 1, 2, 3, 4, 5, 6, 7, 8, 9, 10, 11, 12, 13, 14, 15 or 16), or each, nucleotides at positions 13, 20, 26, 27, 40, 41, 42, 45, 46, 52, 55, 57, 60, 64, 65, 77 of SEQ ID NO:4 are replaced with 5FdUMP.

In embodiments, the aptamer includes or has a nucleic acid sequence of SEQ ID NO:4, where nucleotides at positions 7, 17, 19, 21, 29, 32, 33, 34, 37, 38, 47, 62, 63, 66, 69, 76, 78, 80, 83, and 87 of SEQ ID NO:4 are replaced with dFdCMP.

In embodiments, the aptamer includes or has a nucleic acid sequence of SEQ ID NO:4, where nucleotides at positions 13, 20, 26, 27, 40, 41, 42, 45, 46, 52, 55, 57, 60, 64, 65, 77 of SEQ ID NO:4 are replaced with 5FdUMP.

In embodiments, the aptamer includes or has a nucleic acid sequence of SEQ ID NO:4, where nucleotides at positions 7, 17, 19, 21, 29, 32, 33, 34, 37, 38, 47, 62, 63, 66, 69, 76, 78, 80, 83, and 87 of SEQ ID NO:4 are replaced with dFdCMP; and nucleotides at positions 13, 20, 26, 27, 40, 41, 42, 45, 46, 52, 55, 57, 60, 64, 65, 77 of SEQ ID NO:4 are replaced with 5FdUMP.

In embodiments, the aptamer includes or has a nucleic acid sequence of SEQ ID NO:5, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, or 71), or each, nucleotides of the nucleic acid sequence are replaced with a nucleotide analogue.

In embodiments, the aptamer includes or has a nucleic acid sequence of SEQ ID NO:5, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, or 71), or each, nucleotides of the nucleic acid sequence are replaced with dFdCMP or 5FdUMP.

In embodiments, the aptamer includes or has a nucleic acid sequence of SEQ ID NO:5, where one or more (e.g., 1, 2, 3, 4, 5, 6, 7, 8, 9, 10, 11, 12, 13, 14, 15 or 16), or each, cytidine nucleotides (e.g., at positions 7, 17, 19, 21, 24, 32, 39, 45, 46, 50, 53, 60, 62, 64, 67, and 71) are replaced with a nucleotide analogue. In embodiments, the nucleotide analogue is dFdCMP.

In embodiments, the aptamer includes or has a nucleic acid sequence of SEQ ID NO:5, where one or more (e.g., 1, 2, 3, 4, 5, 6, 7, 8 or 9), or each, uridine nucleotides (e.g., at positions 13, 20, 27, 34, 35, 41, 48, 49, 50, and 61) are replaced with a nucleotide analogue. In embodiments, the nucleotide analogue is 5FdUMP.

In embodiments, the aptamer includes or has a nucleic acid sequence of SEQ ID NO:5, where one or more (e.g., 1, 2, 3, 4, 5, 6, 7, 8, 9, 10, 11, 12, 13, 14, 15 or 16), or each, nucleotides at positions 7, 17, 19, 21, 24, 32, 39, 45, 46, 50, 53, 60, 62, 64, 67, and 71 of SEQ ID NO:5 are replaced with dFdCMP.

In embodiments, the aptamer includes or has a nucleic acid sequence of SEQ ID NO:5, where one or more (e.g., 1, 2, 3, 4, 5, 6, 7, 8 or 9), or each, nucleotides at positions 13, 20, 27, 34, 35, 41, 48, 49, 50, and 61 of SEQ ID NO:5 are replaced with 5FdUMP.

In embodiments, the aptamer includes or has a nucleic acid sequence of SEQ ID NO:5, where one or more (e.g., 1, 2, 3, 4, 5, 6, 7, 8, 9, 10, 11, 12, 13, 14, 15 or 16), or each, nucleotides at positions 7, 17, 19, 21, 24, 32, 39, 45, 46, 50, 53, 60, 62, 64, 67, and 71 of SEQ ID NO:5 are replaced with dFdCMP; and one or more (e.g., 1, 2, 3, 4, 5, 6, 7, 8 or 9), or each, nucleotides at positions 13, 20, 27, 34, 35, 41, 48, 49, 50, and 61 of SEQ ID NO:5 are replaced with 5FdUMP.

In embodiments, the aptamer includes or has a nucleic acid sequence of SEQ ID NO:5, where nucleotides at positions 7, 17, 19, 21, 24, 32, 39, 45, 46, 50, 53, 60, 62, 64, 67, and 71 of SEQ ID NO:5 are replaced with dFdCMP.

In embodiments, the aptamer includes or has a nucleic acid sequence of SEQ ID NO:5, where nucleotides at positions 13, 20, 27, 34, 35, 41, 48, 49, 50, and 61 of SEQ ID NO:5 are replaced with 5FdUMP.

In embodiments, the aptamer includes or has a nucleic acid sequence of SEQ ID NO:5, where nucleotides at positions 7, 17, 19, 21, 24, 32, 39, 45, 46, 50, 53, 60, 62, 64, 67, and 71 of SEQ ID NO:5 are replaced with dFdCMP; and nucleotides at positions 13, 20, 27, 34, 35, 41, 48, 49, 50, and 61 of SEQ ID NO:5 are replaced with 5FdUMP.

In embodiments, the aptamer includes or has a nucleic acid sequence of SEQ ID NO:6, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87), or each, nucleotides of the nucleic acid sequence are replaced with a nucleotide analogue.

In embodiments, the aptamer includes or has a nucleic acid sequence of SEQ ID NO:6, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87), or each, nucleotides of the nucleic acid sequence are replaced with dFdCMP or 5FdUMP.

In embodiments, the aptamer includes or has a nucleic acid sequence of SEQ ID NO:6, where one or more (e.g., 1, 2, 3, 4, 5, 6, 7, 8, 9, 10, 11, 12, 13, 14, 15, 16, 17, 18, 19 or 20), or each, cytidine nucleotides (e.g., at positions 7, 17, 19, 21, 26, 27, 38, 39, 40, 43, 48, 55, 63, 66, 69, 76, 78, 80, 83, and 87) are replaced with a nucleotide analogue. In embodiments, the nucleotide analogue is dFdCMP.

In embodiments, the aptamer includes or has a nucleic acid sequence of SEQ ID NO:6, where one or more (e.g., 1, 2, 3, 4, 5, 6, 7, 8, 9, 10, 11, 12, 13, 14, 15 or 16), or each, uridine nucleotides (e.g., at positions 13, 20, 29, 31, 32, 36, 44, 49, 50, 51, 56, 57, 58, 64, 65, and 77) are replaced with a nucleotide analogue. In embodiments, the nucleotide analogue is 5FdUMP.

In embodiments, the aptamer includes or has a nucleic acid sequence of SEQ ID NO:6, where one or more (e.g., 1, 2, 3, 4, 5, 6, 7, 8, 9, 10, 11, 12, 13, 14, 15, 16, 17, 18, 19 or 20), or each, nucleotides at positions 7, 17, 19, 21, 26, 27, 38, 39, 40, 43, 48, 55, 63, 66, 69, 76, 78, 80, 83, and 87 of SEQ ID NO:6 are replaced with dFdCMP.

In embodiments, the aptamer includes or has a nucleic acid sequence of SEQ ID NO:6, where one or more (e.g., 1, 2, 3, 4, 5, 6, 7, 8, 9, 10, 11, 12, 13, 14, 15 or 16), or each, nucleotides at positions 13, 20, 29, 31, 32, 36, 44, 49, 50, 51, 56, 57, 58, 64, 65, and 77 of SEQ ID NO:6 are replaced with 5FdUMP.

In embodiments, the aptamer includes or has a nucleic acid sequence of SEQ ID NO:6, where one or more, or each, (e.g., 1, 2, 3, 4, 5, 6, 7, 8, 9, 10, 11, 12, 13, 14, 15, 16, 17, 18, 19 or 20) nucleotides at positions 7, 17, 19, 21, 26, 27, 38, 39, 40, 43, 48, 55, 63, 66, 69, 76, 78, 80, 83, and 87 of SEQ ID NO:6 are replaced with dFdCMP; and one or more, or each, (e.g., 1, 2, 3, 4, 5, 6, 7, 8, 9, 10, 11, 12, 13, 14, 15 or 16) nucleotides at positions 13, 20, 29, 31, 32, 36, 44, 49, 50, 51, 56, 57, 58, 64, 65, and 77 of SEQ ID NO:6 are replaced with 5FdUMP.

In embodiments, the aptamer includes or has a nucleic acid sequence of SEQ ID NO:6, where nucleotides at positions 7, 17, 19, 21, 26, 27, 38, 39, 40, 43, 48, 55, 63, 66, 69, 76, 78, 80, 83, and 87 of SEQ ID NO:6 are replaced with dFdCMP.

In embodiments, the aptamer includes or has a nucleic acid sequence of SEQ ID NO:6, where nucleotides at positions 13, 20, 29, 31, 32, 36, 44, 49, 50, 51, 56, 57, 58, 64, 65, and 77 of SEQ ID NO:6 are replaced with 5FdUMP.

In embodiments, the aptamer includes or has a nucleic acid sequence of SEQ ID NO:6, where nucleotides at positions 7, 17, 19, 21, 26, 27, 38, 39, 40, 43, 48, 55, 63, 66, 69, 76, 78, 80, 83, and 87 of SEQ ID NO:6 are replaced with dFdCMP; and nucleotides at positions 13, 20, 29, 31, 32, 36, 44, 49, 50, 51, 56, 57, 58, 64, 65, and 77 of SEQ ID NO:6 are replaced with 5FdUMP.

In embodiments, the aptamer includes or has a nucleic acid sequence of SEQ ID NO:7, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87), or each, nucleotides of the nucleic acid sequence are replaced with a nucleotide analogue.

In embodiments, the aptamer includes or has a nucleic acid sequence of SEQ ID NO:7, where one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, or 87), or each, nucleotides of the nucleic acid sequence are replaced with dFdCMP or 5FdUMP.

In embodiments, the aptamer includes or has a nucleic acid sequence of SEQ ID NO:7, where one or more (e.g., 1, 2, 3, 4, 5, 6, 7, 8, 9, 10, 11, 12, 13, 14, 15, 16, 17, 18 or 19), or each, cytidine nucleotides (e.g., at positions 7, 17, 21, 31, 32, 33, 45, 49, 51, 54, 55, 63, 66, 69, 76, 78, 80, 83, and 87) are replaced with a nucleotide analogue. In embodiments, the nucleotide analogue is dFdCMP.

In embodiments, the aptamer includes or has a nucleic acid sequence of SEQ ID NO:7, where one or more (e.g., 1, 2, 3, 4, 5, 6, 7, 8, 9, 10, 11, 12, 13, 14, 15, 16, 17 or 18), or each, uridine nucleotides (e.g., at positions 13, 20, 25, 28, 29, 35, 36, 40, 41, 43, 46, 47, 52, 53, 56, 64, 65, and 77) are replaced with a nucleotide analogue. In embodiments, the nucleotide analogue is 5FdUMP.

In embodiments, the aptamer includes or has a nucleic acid sequence of SEQ ID NO:7, where one or more (e.g., 1, 2, 3, 4, 5, 6, 7, 8, 9, 10, 11, 12, 13, 14, 15, 16, 17, 18 or 19), or each, nucleotides at positions 7, 17, 21, 31, 32, 33, 45, 49, 51, 54, 55, 63, 66, 69, 76, 78, 80, 83, and 87 of SEQ ID NO:7 are replaced with dFdCMP.

In embodiments, the aptamer includes or has a nucleic acid sequence of SEQ ID NO:7, where one or more (e.g., 1, 2, 3, 4, 5, 6, 7, 8, 9, 10, 11, 12, 13, 14, 15, 16, 17 or 18), or each, nucleotides at positions 13, 20, 25, 28, 29, 35, 36, 40, 41, 43, 46, 47, 52, 53, 56, 64, 65, and 77 of SEQ ID NO:7 are replaced with 5FdUMP.

In embodiments, the aptamer includes or has a nucleic acid sequence of SEQ ID NO:7, where one or more (e.g., 1, 2, 3, 4, 5, 6, 7, 8, 9, 10, 11, 12, 13, 14, 15, 16, 17, 18 or 19), or each, nucleotides at positions 7, 17, 21, 31, 32, 33, 45, 49, 51, 54, 55, 63, 66, 69, 76, 78, 80, 83, and 87 of SEQ ID NO:7 are replaced with dFdCMP; and one or more (e.g., 1, 2, 3, 4, 5, 6, 7, 8, 9, 10, 11, 12, 13, 14, 15, 16, 17 or 18), or each, nucleotides at positions 13, 20, 25, 28, 29, 35, 36, 40, 41, 43, 46, 47, 52, 53, 56, 64, 65, and 77 of SEQ ID NO:7 are replaced with 5FdUMP.

In embodiments, the aptamer includes or has a nucleic acid sequence of SEQ ID NO:7, where nucleotides at positions 7, 17, 21, 31, 32, 33, 45, 49, 51, 54, 55, 63, 66, 69, 76, 78, 80, 83, and 87 of SEQ ID NO:7 are replaced with dFdCMP.

In embodiments, the aptamer includes or has a nucleic acid sequence of SEQ ID NO:7, where nucleotides at positions 1, 3, 20, 25, 28, 29, 35, 36, 40, 41, 43, 46, 47, 52, 53, 56, 64, 65, and 77 of SEQ ID NO:7 are replaced with 5FdUMP.

In embodiments, the aptamer includes or has a nucleic acid sequence of SEQ ID NO:7, where nucleotides at positions 7, 17, 21, 31, 32, 33, 45, 49, 51, 54, 55, 63, 66, 69, 76, 78, 80, 83, and 87 of SEQ ID NO:7 are replaced with dFdCMP; and nucleotides at positions 13, 20, 25, 28, 29, 35, 36, 40, 41, 43, 46, 47, 52, 53, 56, 64, 65, and 77 of SEQ ID NO:7 are replaced with 5FdUMP.

In embodiments, the aptamer includes a nucleic acid sequence of SEQ ID NO:8, where one or more, or each, nucleotides of the nucleic acid sequence are replaced with a nucleotide analogue.

In embodiments, the aptamer includes a nucleic acid sequence of SEQ ID NO:8, where one or more, or each, nucleotides of the nucleic acid sequence are replaced with dFdCMP or 5FdUMP.

In embodiments, the aptamer includes a nucleic acid sequence of SEQ ID NO:8, where one or more, or each, cytidine nucleotides (e.g., at positions 6, 7, and 8) are replaced with a nucleotide analogue. In embodiments, the nucleotide analogue is dFdCMP.

In embodiments, the aptamer includes a nucleic acid sequence of SEQ ID NO:8, where the uridine nucleotide (e.g., at position 4) is replaced with a nucleotide analogue. In embodiments, the nucleotide analogue is 5FdUMP.

In embodiments, the aptamer includes a nucleic acid sequence of SEQ ID NO:8, where one or more, or each, (e.g., 1, 2 or 3) nucleotides at positions 6, 7, and 8 of SEQ ID NO:8 are replaced with dFdCMP.

In embodiments, the aptamer includes a nucleic acid sequence of SEQ ID NO:8, where the nucleotide at position 4 of SEQ ID NO:8 is replaced with 5FdUMP.

In embodiments, the aptamer includes a nucleic acid sequence of SEQ ID NO:8, where one or more, or each, (e.g., 1, 2 or 3) nucleotides at positions 6, 7, and 8 of SEQ ID NO:8 are replaced with dFdCMP; and the nucleotide at position 4 of SEQ ID NO:8 is replaced with 5FdUMP.

In embodiments, the aptamer includes a nucleic acid sequence of SEQ ID NO:8, where the nucleotides at positions 6, 7, and 8 of SEQ ID NO:8 are replaced with dFdCMP.

In embodiments, the aptamer includes a nucleic acid sequence of SEQ ID NO:8, where the nucleotides at positions 6, 7, and 8 of SEQ ID NO:8 are replaced with dFdCMP; and the nucleotide at position 4 of SEQ ID NO: 8 is replaced with 5FdUMP.

In embodiments, the aptamer includes a nucleic acid sequence of any one of SEQ ID NOs: 1-8, where one or more, or each, nucleotides of the nucleic acid sequence are replaced with a nucleotide analogue (for example, dFdCMP or 5FdUMP) and the aptamer is bound to at least one small molecule, e.g., PBD, MMAE, DM1, oxaliplatin, irinotecan or doxorubicin.

In embodiments, the aptamer includes a nucleic acid sequence of any one of SEQ ID NOs: 1-8, where one or more, or each, cytidine nucleotides of the nucleic acid sequence are replaced dFdCMP and the aptamer is bound to at least one small molecule, e.g., PBD, MMAE, DM1, oxaliplatin, irinotecan or doxorubicin.

In embodiments, the aptamer includes a nucleic acid sequence of any one of SEQ ID NOs: 1-8, where one or more, or each, uridine nucleotides of the nucleic acid sequence are replaced with 5FdUMP and the aptamer is bound to at least one small molecule, e.g., PBD, MMAE, DM1, oxaliplatin, irinotecan or doxorubicin.

In embodiments, the aptamer includes a nucleic acid sequence of any one of SEQ ID NOs: 1-8, where one or more, or each, cytidine nucleotides of the nucleic acid sequence are replaced dFdCMP, one or more, or each, uridine nucleotides of the nucleic acid sequence are replaced with 5FdUMP, and the aptamer is bound to at least one small molecule, e.g., PBD, MMAE, DM1, oxaliplatin, irinotecan or doxorubicin.

Pharmaceutical Formulations

Pharmaceutical compositions of the compounds (e.g., nucleic acid compounds) provided herein may include compositions having an anticancer agent contained in a therapeutically effective amount, i.e., in an amount effective to achieve its intended purpose. The actual amount effective for a particular application will depend, inter alia, on the condition being treated, tested, detected, or diagnosed. When administered in methods to treat a disease, such compositions will contain an amount of active ingredient effective to achieve the desired result, e.g., modulating the activity of a target molecule, and/or reducing, eliminating, or slowing the progression of disease symptoms. Determination of a therapeutically effective amount of a therapeutic moiety provided herein is well within the capabilities of those skilled in the art, especially in light of the detailed disclosure herein. When administered in methods to diagnose or detect a disease, such compositions will contain an amount of an imaging moiety described herein effective to achieve the desired result, e.g., detecting the absence or presence of a target molecule, cell, or tumor in a subject. Determination of a detectable amount of an imaging moiety provided herein is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compositions described herein including embodiments thereof. Adjustment and manipulation of established dosages (e.g., frequency and duration) are well within the ability of those skilled in the art.

For any composition (e.g., the nucleic acid compounds provided, compositions of an anticancer agent and the nucleic acid compound provided) described herein, the therapeutically effective amount can be initially determined from cell culture assays. Target concentrations will be those concentrations of active compound(s) that are capable of achieving the methods described herein, as measured using the methods described herein or known in the art. As is well known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

In another aspect, there is provided a pharmaceutical formulation including a composition including an aptamer and an anticancer agent as disclosed herein, and embodiments thereof, and a pharmaceutically acceptable excipient.

"Pharmaceutically acceptable excipient" and "pharmaceutically acceptable carrier" refer to a substance that aids the administration of an active agent to and absorption by a subject and can be included in the compositions described herein without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylase or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compositions described herein. One of skill in the art will recognize that other pharmaceutical excipients are useful.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

Methods

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma). For example certain methods herein treat cancer by decreasing or reducing or preventing the occurrence, growth, metastasis, or progression of cancer; or treat cancer by decreasing a symptom of cancer. Symptoms of cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma) would be known or may be determined by a person of ordinary skill in the art.

An "effective amount" is an amount sufficient to accomplish a stated purpose (e.g. achieve the effect for which it is administered, treat a disease, reduce enzyme activity, reduce one or more symptoms of a disease or condition, reduce viral replication in a cell). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999);

Pickar, *Dosage Calculations* (1999); and *Remington: The Science and Practice of Pharmacy,* 20th Edition, 2003, Gennaro, Ed., Lippincott, Williams & Wilkins).

"Patient" or "subject in need thereof" refers to a living organism suffering from or prone to a disease or condition that can be treated by using the methods provided herein. The term does not necessarily indicate that the subject has been diagnosed with a particular disease, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal).

Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compositions described herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions described herein can be delivered by transdermally, by a topical route, formulated as applicator sticks, solutions, suspensions, emulsions, gels, creams, ointments, pastes, jellies, paints, powders, and aerosols.

In another aspect, there is provided a method of treating cancer. The method includes administering to a subject in need thereof an effective amount of a composition as disclosed and embodiments thereof.

In another aspect, there is provided a composition including an aptamer and an anticancer agent as disclosed herein for use in a method of treating cancer. The method includes administering to a subject in need thereof an effective amount of a composition as disclosed and embodiments thereof.

In another aspect, there is provided the use of a composition including an aptamer and an anticancer agent as disclosed herein in the manufacture of a medicament or pharmaceutical composition for use in a method of treating cancer. The method includes administering to a subject in need thereof an effective amount of a composition as disclosed and embodiments thereof.

In embodiments, the cancer overexpresses HSP70 or HSP90 or vimentin. In embodiments, the cancer overexpresses HSP70 or mHSP70. In embodiments, the cancer overexpresses HSP90. In embodiments, the cancer overexpresses vimentin.

In embodiments, the cancer is an undifferentiated cancer. An "undifferentiated cancer" refers to a cancer in which the cells are very immature and "primitive" and do not look like cells in the tissue from it arose. These tumors may have abnormal looking cells and may lack normal tissue structures. As a general observation in the field, an undifferentiated cancer is more malignant than a cancer of that type which is well differentiated. In embodiments, the cancer is an undifferentiated metastatic cancer.

In embodiments, the cancer is pancreatic cancer, colon cancer or glioblastoma. In embodiments, the cancer is pancreatic cancer. In embodiments, the cancer is colon cancer. In embodiments, the cancer is glioblastoma.

Informal Sequence Listing

```
P1:
                                           (SEQ ID NO: 1)
GGGAGACAAGAAUAAACGCUCAAUGCGCUGAAUGCCCAGCCGUG

AAAGCGUCGAUUUCCAUCCUUCGACAGGAGGCUCACAACAGGC

P19:
                                           (SEQ ID NO: 2)
GGGAGACAAGAAUAAACGCUCAAUGGCGAAUGCCCGCCUAAUAG

GGCGUUAUGACUUGUUGAGUUCGACAGGAGGCUCACAACAGGC tP19:
                                           (SEQ ID NO: 3)
CUCAAUGGCGAAUGCCCGCCUAAUAGGG

P15:
                                           (SEQ ID NO: 4)
GGGAGACAAGAAUAAACGCUCAAAGUUGCGGCCCAACCGUUUAA

UUCAGAAUAGUGUGAUGCCUUCGACAGGAGGCUCACAACAGGC

P6:
                                           (SEQ ID NO: 5)
GGGAGACAAGAAUAAACGCUCAACAAUGGAGCGUUAAACGUGAG

CCAUUCGACAGGAGGCUCACAACAGGC

P7:
                                           (SEQ ID NO: 6)
GGGAGACAAGAAUAAACGCUCAAGGCCAUGUUGAAUGCCCAACU

AAGCUUUGAGCUfUUGGAGCUUCGACAGGAGGCUCACAACAGGC

P11:
                                           (SEQ ID NO: 7)
GGGAGACAAGAAUAAACGCUCAAAUGAUUGCCCAUUCGGUUAUG

CUUGCGCUUCCUAAAGAGCUUCGACAGGAGGCUCACAACAGGC

Consensus:
                                           (SEQ ID NO: 8)
GA[A/U]UGCCC
```

P1 (SEQ ID NO:1) conjugated to hybridization sequence via polycarbon linker:

```
                                           (SEQ ID NO: 9)
GGGAGAfCAAGAAfUAAAfCGfCfUfCAAfUGfCGfCfUGAAfU

GfCfCfCAGfCfCGfUGAAAGfCGfUfCGAfUfUfUfCfCAfUf

CfCfUfUfCGAfCAGGAGGfCfUfCAfCAAfCAGGfCooooooo mAmGfUfUfUfUfUfUmAfCmAfUfUfUfUmG
```

P19 (SEQ ID NO:2) conjugated to hybridization sequence via polycarbon linker:

(SEQ ID NO: 10)
GGGAGAfCAAGAAfUAAAfCGfCfUfCAAfUGGfCGAAfUGfCf

CfCGfCfCfUAAfUfAGGGfCGfUfUAfUGAfCfUfUGfUfUGA

GfUfUfCGAfCAGGAGGfCfUfCAfCAAfCAGGfCooooooomA mGfUfUfUfUfUfUmAfCmAfUfUfUfUmG tP19 (truncated P19; pancreatic cancer aptamer) conjugated to hybridization sequence via polycarbon linker:

(SEQ ID NO: 11)
fCfUfCAAfUGGfCGAAfUGfCfCfCGfCfCfUAAfUAGGGooo ooooomAmGfUfUfUfUfUfUmAfCmAfUfUfUfUmG

P15 (SEQ ID NO:4) conjugated to hybridization sequence via polycarbon linker:

(SEQ ID NO: 12)
GGGAGAfCAAGAAfUAAAfCGfCfUfCAAAGfUfUGfCGGfCfC fCAAfCfCGfUfUfUAAfUfUfCAGAAfUAGfUGfUGAfUGfCf

CfUfUfCGAfCAGGAGGfCfUfCAfCAAfCAGGfCooooooomA mGfUfUfUfUfUfUmAfCmAfUfUfUfUmG

P6 (SEQ ID NO:5) conjugated to hybridization sequence via polycarbon linker:

(SEQ ID NO: 13)
GGGAGAfCAAGAAfUAAAfCGfCfUfCAAfCAAfUGGfAGfCGf

UfUAAAfCGfUGAGfCfCAfUfUfCGAfCAGGAGGfCfUfCAfC

AAfCAGGfCooooooomAmGfUfUfUfUfUfUmAfCmAfUfUfU fUmG

P7 (SEQ ID NO:6) conjugated to hybridization sequence via polycarbon linker:

(SEQ ID NO: 14)
GGGAGAfCAAGAAfUAAAfCGfCfUfCAAGGfCfCAfUGfUfUG

AAfUGfCfCfCAAfCfUAAGfCfUfUfUGAGfCfUfUfUGGAGf

CfUfUfCGAfCAGGAGGfCfUfCAfCAAfCAGGfCooooooomA mGfUfUfUfUfUfUmAfCmAfUfUfUfUmG

P11 (SEQ ID NO:7) conjugated to hybridization sequence via polycarbon linker:

(SEQ ID NO: 15)
GGGAGAfCAAGAAfUAAAfCGfCfUfCAAAfUGAfUfUGfCfCf

CAfUfUfCGGfUfUAfUGfCfUfUGfCGfCfUfUfCfCfUAAAG

AGfCfUfUfCfGAfCAGGAGGfCfUfCAfCAAfCAGGfCooooo oomAmGfUfUfUfUfUmAfCmAfUfUfUfUmG

Bold: hybridization sequence. fU and fC: 2'F modified pyrimidines. mA and mG: 2'O methylated purines. o: C3 carbon linker (—(CH$_2$)$_n$—PO$_4$—).

P19 (SEQ ID NO:2) and P1 (SEQ ID NO:1) are mHSP70 binding aptamers, each capable of internalizing upon binding of mHSP70 at the cell surface. They are described in WO2013/154735.

tP19 (SEQ ID NO:3) is an mHSP70 binding aptamer capable of internalising upon binding of mHSP70 at the cell surface, and described in WO2013/154735. tP19 is a truncated form of aptamer P19 which also binds mHSP70, also described in WO2013/154735. WO2013/154735 is specifically incorporated herein by reference in its entirety. tP19 is also described in U.S. provisional patent application No. 62/141,156, specifically incorporated herein by reference in its entirety.

P15 (SEQ ID NO:4) is a vimentin binding aptamer capable of internalizing upon binding vimentin at the cell surface.

P6 (SEQ ID NP:5), P7 (SEQ ID NO:6) and P11 (SEQ ID NO:7) are HSP90 binding aptamers capable of internalizing upon binding HSP90 at the cell surface.

EMBODIMENTS

Embodiments contemplated herein include embodiments P1 to p40 following.

Embodiment P1

A composition comprising an aptamer and an anticancer agent, wherein said aptamer is bound to said anticancer agent.

Embodiment P2

The composition of embodiment P1, wherein said anticancer agent is a small molecule, a nucleotide analogue, a nucleic acid, or a peptide.

Embodiment P3

The composition of embodiment P2, wherein said anticancer agent is a small molecule.

Embodiment P4

The composition of embodiment P3, wherein said small molecule is PBD, MMAE, DM1, oxaliplatin, irinotecan or doxorubicin.

Embodiment P5

The composition of embodiment P3, wherein said small molecule is bound to said aptamer via a linker.

Embodiment P6

The composition of embodiment P5, wherein said linker comprises a first nucleic acid hybridized to a second nucleic acid, wherein said first nucleic acid is covalently bound to said anticancer agent and said second nucleic acid is covalently bound to said aptamer.

Embodiment P7

The composition of embodiment P3, wherein said small molecule is covalently bound to said aptamer.

Embodiment P8

The composition of embodiment P3, wherein said small molecule is non-covalently bound to said aptamer.

Embodiment P9

The composition of embodiment P2, wherein said anti-cancer agent is a nucleotide analogue, a nucleoside analogue, a pyrimidine analogue or a purine analogue.

Embodiment P10

The composition of embodiment P9, wherein said anti-cancer agent is gemcitabine, 5-flurouracil or a metabolite thereof.

Embodiment P11

The composition of embodiment P9, wherein said anti-cancer agent is gemcitabine monophosphate (dFdCMP) or 5-F-uridine monophosphate (5FdUMP).

Embodiment P12

The composition of embodiment P9, wherein said anti-cancer agent is present within the nucleic acid sequence of said aptamer.

Embodiment P13

The composition of embodiment P12, wherein said anti-cancer agent is gemcitabine or gemcitabine analogue, wherein said gemcitabine or gemcitabine analogue is present within the nucleic acid sequence at one or more cytidine positions.

Embodiment P14

The composition of embodiment P12, wherein said anti-cancer agent is 5-fluorouracil or 5-fluorouracil analogue, wherein said 5-fluorouracil or 5-fluorouracil analogue is present within the nucleic acid sequence at one or more uridine positions.

Embodiment P15

The composition of embodiment P1, wherein said composition is bound to a cellular receptor.

Embodiment P16

The composition of embodiment P15, wherein said cellular receptor is cell surface HSP70.

Embodiment P17

The composition of embodiment P16, wherein said HSP70 is mHSP70 (mortalin).

Embodiment P18

The composition of embodiment P15, wherein said cellular receptor is cell surface HSP90.

Embodiment P19

The composition of embodiment P15, wherein said cellular receptor is cell surface vimentin.

Embodiment P20

The composition of embodiment P15, wherein said cellular receptor is present on a cancer cell.

Embodiment P21

The composition of embodiment P20, wherein said cancer cell is a cancer stem cell.

Embodiment P22

The composition of embodiment P20, wherein said cancer cell is an undifferentiated cancer cell.

Embodiment P23

The composition of embodiment P22, wherein said cancer cell is an undifferentiated metastatic cancer cell.

Embodiment P24

The composition of embodiment P23, wherein said cancer cell is a pancreatic cancer cell, a glioblastoma cell, a colon cancer cell.

Embodiment P25

The composition of any one of embodiments P1 to P24, wherein said aptamer comprises a nucleic acid sequence of one of SEQ ID Nos: 1 to 7.

Embodiment P26

The composition of any one of embodiments P1 to P24, wherein said aptamer comprises a nucleic acid sequence having at least 80% sequence identity to one of SEQ ID Nos: 1 to 7.

Embodiment P27

The composition of any one of embodiments P1 to P24, wherein said aptamer comprises a nucleic acid sequence of SEQ ID NO: 8.

Embodiment 28

The composition of embodiment P1, wherein said aptamer comprises a nucleic acid sequence of SEQ ID NO:3, and said aptamer is bound to PBD, MMAE, DM1, oxaliplatin, irinotecan or doxorubicin.

Embodiment P29

The composition of embodiment P1, wherein said aptamer comprises a nucleic acid sequence of SEQ ID NO: 1, wherein one or more nucleotides of said nucleic acid sequence are replaced with dFdCMP or 5FdUMP.

Embodiment P30

The composition of embodiment P1, wherein said aptamer comprises a nucleic acid sequence of SEQ ID NO:2, wherein one or more nucleotides of said nucleic acid sequence are replaced with dFdCMP or 5FdUMP.

Embodiment P31

The composition of embodiment P1, wherein said aptamer comprises a nucleic acid sequence of SEQ ID NO:3, wherein one or more nucleotides of said nucleic acid sequence are replaced with dFdCMP or 5FdUMP.

Embodiment P32

The composition of embodiment P1, wherein said aptamer comprises a nucleic acid sequence of SEQ ID NO:4, wherein one or more nucleotides of said nucleic acid sequence are replaced with dFdCMP or 5FdUMP.

Embodiment P33

The composition of embodiment P1, wherein said aptamer comprises a nucleic acid sequence of SEQ ID NO:5, wherein one or more nucleotides of said nucleic acid sequence are replaced with dFdCMP or 5FdUMP.

Embodiment P34

The composition of embodiment P1, wherein said aptamer comprises a nucleic acid sequence of SEQ ID NO:6, wherein one or more nucleotides of said nucleic acid sequence are replaced with dFdCMP or 5FdUMP.

Embodiment P35

The composition of embodiment P1, wherein said aptamer comprises a nucleic acid sequence of SEQ ID NO:7, wherein one or more nucleotides of said nucleic acid sequence are replaced with dFdCMP or 5FdUMP.

Embodiment P36

A pharmaceutical formulation comprising the composition of any one of embodiments P1 to P35 and a pharmaceutically acceptable excipient.

Embodiment P37

A method of treating cancer, the method comprising administering to a subject in need thereof an effective amount of the composition of any one of embodiments P1 to P35.

Embodiment P38

The method of embodiment P37, wherein said cancer overexpresses HSP70 or HSP90 or vimentin.

Embodiment P39

The method of embodiment P37, wherein said cancer is an undifferentiated metastatic cancer.

Embodiment P40

The method of embodiment P37, wherein said cancer is pancreatic cancer, colon cancer or glioblastoma.

EXAMPLES

Example 1—Aptamer Drug Conjugates (ApDCs) of Active Metabolites of Gemcitabine and 5-FU Inhibit Cell Growth Through DNA Damage in Pancreatic Adenonocarcinoma (PDAC)

Abstract. Gemcitabine and 5-Fluorouracil (5-FU) are nucleoside analogues used to treat cancer as anti-neoplastic drugs. Cytotoxic effects for these agent have been principally ascribed to mis-incorporation of fluoronucleotides into DNA and RNA during synthesis and the inhibition of thymidylate synthase (TS) by dFdCMP and FdUMP (one of the gemcitabine and 5-FU active metabolites), which leads to nucleotide pool imbalance. Moreover, both agents are nonspecifically absorbed into non-targeting cells. To reduce the non-specific uptakes and increase the specificity of drugs, we conjugated intrinsically the active metabolites of gemcitabine and 5-FU to an RNA aptamer to afford an aptamer drug conjugates (ApDCs). This study demonstrated that ApDCs with dFdCMP and FdUMP can induce DNA double-strand breaks (DSBs) in the nucleus, cell cycle arrest and apoptosis, consequently inhibiting cell proliferation in PANC-1 and gemcitabine resistance ASPC-1 cells without harming normal cells.

Introduction

Gemcitabine (2'-difluoro modified pyrimidine analogue of dFdC) is an approved standard of chemotherapy in pancreatic cancer [1]. However, the majority of pancreatic cancer patients do not respond to it. Without wishing to be bound by any theory, it is believed that the lack of response is due to poor uptake of drug that is caused by the lack of gemcitabine transporter (human equilibrative nucleoside transporter 1, hENT1) [2,3]. Indeed, low expression of dCK. a gemcitabine uptaker, human equivalent nucleoside transporter 1 (hENT1), is reduced in expression suggesting that chemoresistance is due to poor of uptake [2,3]. In order to take effects as a chemoagents in cancer cells, gemcitabine prodrug (dFdC) is phosphorylated to monophosphate gemcitabine (dFdCMP) by deoxycytidine kinase (dCK) [4]. In gemcitabine resistant pancreatic cancer cell line, a loss of dCK expression was also observed [4]. It has been shown that phosphoramidate prodrug (dFdCMP) is 4-fold more effective then dFdC bypassing dCK deficiency [5].

5-Fluorouracil (5-FU) is a prodrug used to treat various malignant cancers. 5-FU is a modified pyrimidine analogue in place of hydrogen at the carbon-5 position of the pyrimidine ring. Similar to the action of gemcitabine, 5-FU also requires uptake and conversion to its active forms before exerting its cytotoxic effects. As anti-metabolites, the most known action mechanism is inhibition of DNA synthesis [6]. Because of fluorine's high electronegativity, it often binds to other molecules [7], thereby preventing DNA chain elongation. Their effects have also been principally ascribed to misincorporation of fluoronucleotides into DNA, RNA and inhibition of thymidylate synthase (TS) [8-10].

For delivering chemotherapeutic agents in cancer cells specifically, small structured single-stranded RNAs known as aptamers, recognizing targets specifically, are powerful tools. Due to their structure specificity against targets, RNA aptamers recognize cancer cells and are internalized, thereby delivering active metabolites, dFdCMP and FdUMP, into cancer cells specifically. Therefore, regardless of low uptake and low metabolism, RNA aptamers can deliver dFdCMP to cancer cells specifically and induce anti-metabolites effects on cancer cells only.

Materials and Methods

Chemicals.

Gemcitabine triphosphate (dFdCTP) was purchased from Sierra Bioresearch. 5-F-2'-UTP triphosphate (5FdUTP) was purchased from TriLink. DuraScribe T7 transcription kit (Epicentre) was used to incorporate dFdCTP and 5FdUTP into aptamers. Micro Bio-spin P30 (Bio-rad) was used to remove unincorporated dFdCTP and 5FdUTP. Primary and secondary antibodies for rH2AX were purchased from Cell signaling.

Cell Line and Culture.

The following cell lines were purchased from the American Type Culture Collection (ATCC) PANC-1 (CRL-1469), AsPC-1 (CRL-1682), HCT116 (CCL-247), MCF7 (HTB-22), and BJ (CRL-2522). U251 was purchased from sigma. The cells were cultured according to the cell bank's instructions.

Live-Cell Confocal Imaging.

For the aptamer internalization studies, $1\times10^5$ cells were seeded in 35 mm glass-bottom dishes (MatTek, Ashland, Mass., USA) and grown in medium for 24 hrs. The RNAs were labeled with Cy3 using the Cy3 Silencer siRNA labeling kit (Ambion, Tex., USA.). Cy3-labeled RNAs were added to the cells at 200 nM and incubated for 2 hour. The images were taken using a Zeiss LSM 510 Meta Inverted 2 photon confocal microscope system using a C-Apo 40x/1.2NA water immersion objective.

Cell Cycle Analysis.

For cell cycle evaluation, $5\times10^5$ cells were treated with P19, P19-5FdUMP-ApDC and -dFdCMP-ApDC at 1 µM for 48 and 72 hrs. After treatments, cells were harvested and fixed in 70% ethanol for overnight. The samples were washed with PBS. After centrifuge, the cells were resuspended in 500 µl Propidium Iodide (PI)/Triton X-100 staining solution (to 10 ml of 0.1% (v/v) Triton X-100, 2 mg DNAse-free RNAse A and 0.40 ml of 500 µg/ml PI) for 37° C. for 15 minutes. The cells were analyzed with flow cytometry. The data was analyzed by ModFit software.

rH2AX Evaluation.

In order to investigate whether 5FdUMP and dFdCMP induced DSBs in nucleus, the evaluation of rH2AX, a biomarker of DSBs (double strand breaks), was performed by IFA and flow analysis. For immunoassay, $5\times10^4$ of PANC-1 cells were seeded in four chamber slider one day before. P19, P19-5FdUMP and -dFdCMP at 500 nM was incubated in cells for 48 hrs. The cells were fixed in 3% paraformaldehyde solution and permeabilized in 0.1% Triton X-100. Cells were stained with antibodies of rH2AX. The dots in nuclear were counted by Image Pro software. For flow analysis, $5\times10^5$ of PANC-1 cells were treated with P19, P19-5FdUMP and -dFdCMP at 1 uM for 48 hrs. After treatment, cells were harvested with trypsin and fixed in 70% ethanol. Cells were washed with cold PBS and incubated with primary mouse antibodies against rH2AX (1:2000) for 2 hours. The secondary antibodies conjugated with Alexa-488 (1:5000) were incubated for 1 hour. The fluorescence was measured by flow cytometry.

Cell Proliferation Assay.

For the cell viability assay, $5\times10^3$ cells per well of PANC-1 and ASPC-1 were seeded onto 96 well plates one day before. P19, P19-5FdUMP and -dFdCMP at 1 µM were incubated for 72 hrs. After 72 hrs, the inhibition of cell proliferation was measured by MTT assay.

Statistical Analysis.

Statistically significant differences were determined by Students t-test using Graph Pad Prism software (GraphPad Software, La Jolla, Calif., USA).

Results

Cytotoxicity of P19-dFdCMP and P19-5FdUMP in Pancreatic Cancer Cell Line

Figure 1C:
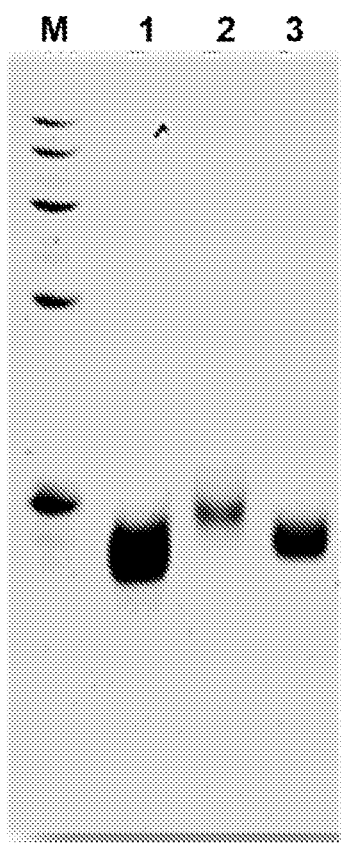
Figure 1D:
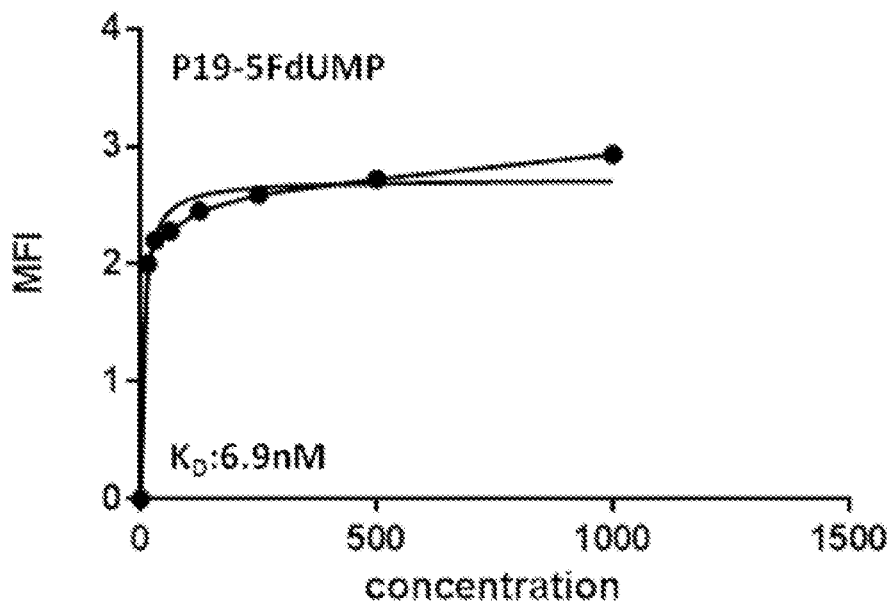
Figure 1D:
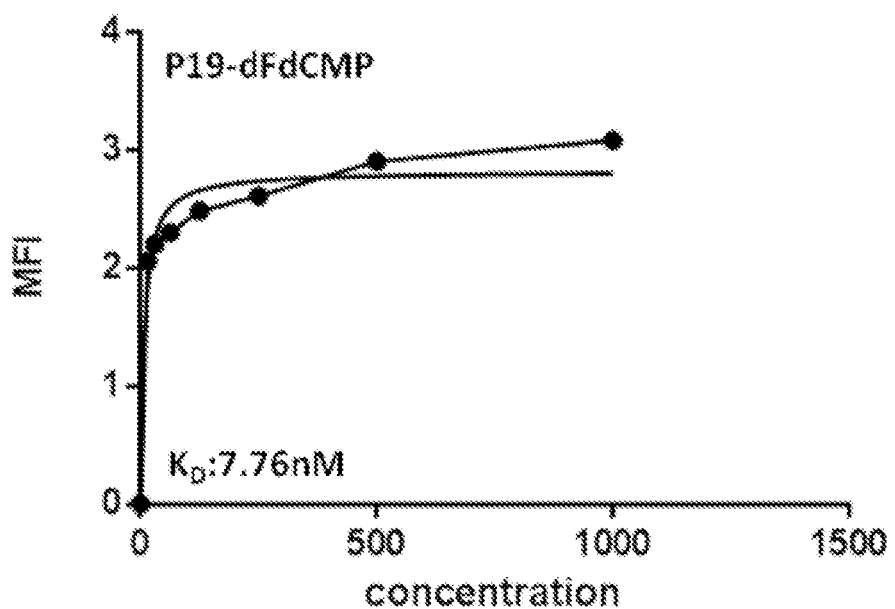
Figure 2A:
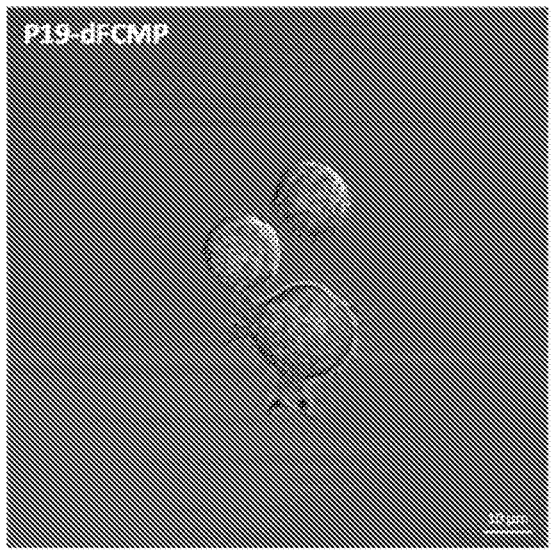
FIGS. 2A-2D. Cell proliferation assay of dFdC-P19-ApDC and 5FdU-P19-ApDC.
Figure 2B:
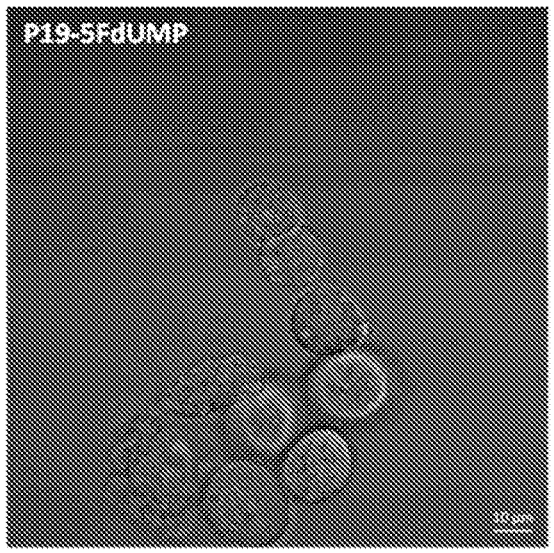

The chemical structural of gemcitabine triphosphate (dFdCTP) and 5-F-2'-UTP triphosphate (5FdUTP) to make ApDC were shown in FIGS. 1A and 1B. Active metabolites dFdCMP and 5FdUMP were intrinsically incorporated into P19 RNA aptamer enzymatically. 2'F'-pyrimidine-ribonucleic acid uracil and cytosine were substituted with dFdCMP or 5FdUMP in aptamer sequence, respectively. The molecular weights of P19-dFdCMP-ApDC and P19-5FdUMP-ApDC were slightly increased (FIG. 1C). The measured binding affinity for P19-dFdCMP-ApDC and P19-5FdUMP-ApDC was 7.8 nM and 6.9 nM, respectively (FIG. 1D). P19-dFdCMP and P19-5FdUMP was internalized into PANC-1 cells without losing functionality (FIGS. 2A-2B).

Figure 2C:
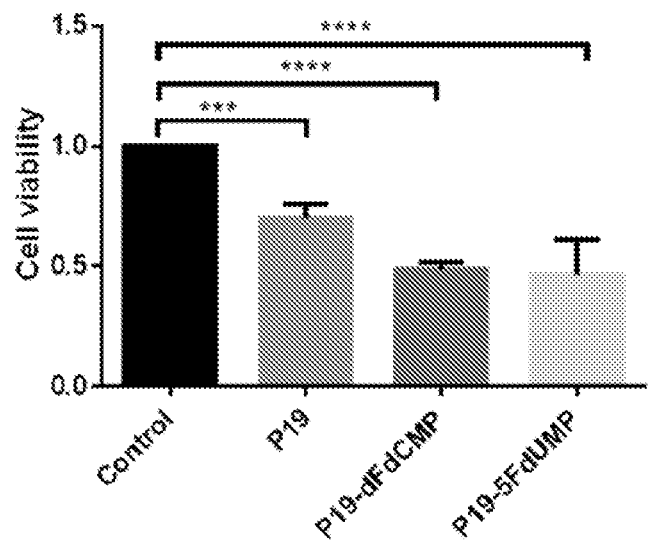
Figure 2D:
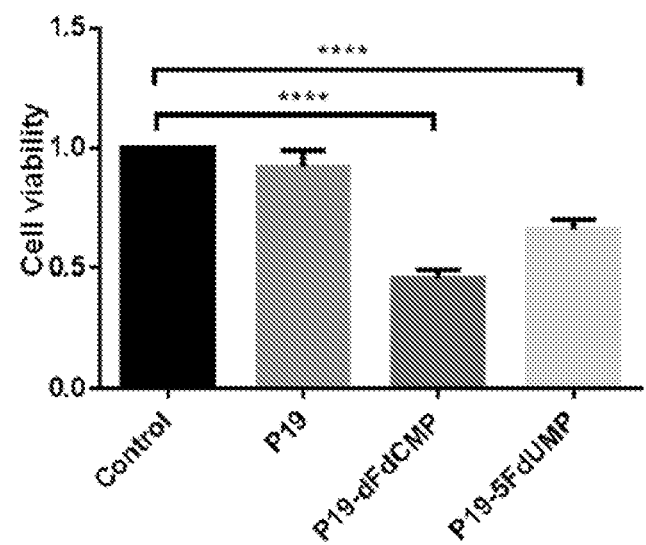

The cell viability of both P19-dFdCMP and P19-5FdUMP was assessed by MTT assay. FIGS. 2C and 2D depict that P19-dFdCMP and P19-5FdUMP inhibited cell proliferation at 72 hrs significantly, even in gemcitabine resistance cell AsPC-1. There was no significant difference in cytotoxicity of P19-dFdCMP observed in PANC-1 and AsPC-1. But, P19-5FdUMP showed more potency in PANC-1 cells than AsPC-1.

DNA Double-Strand Breaks (DSBs).

Figure 3A:
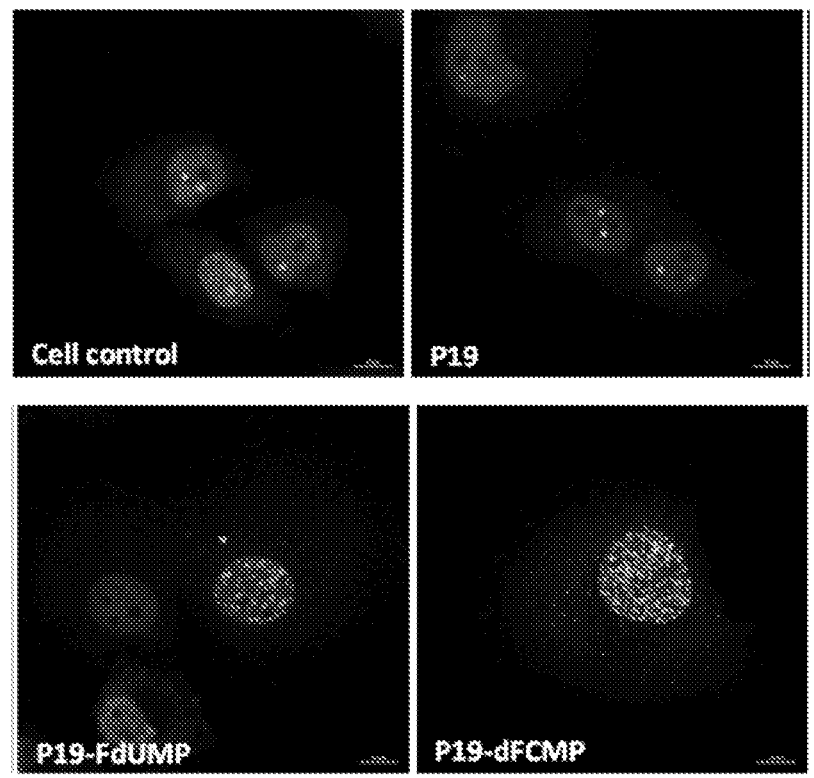
FIGS. 3A-3B. rH2AX of DSBs.
Figure 3B:
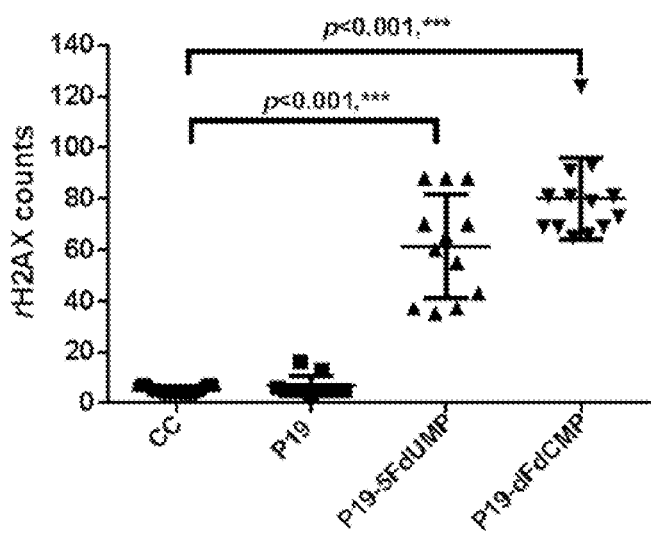
Figure 4A:
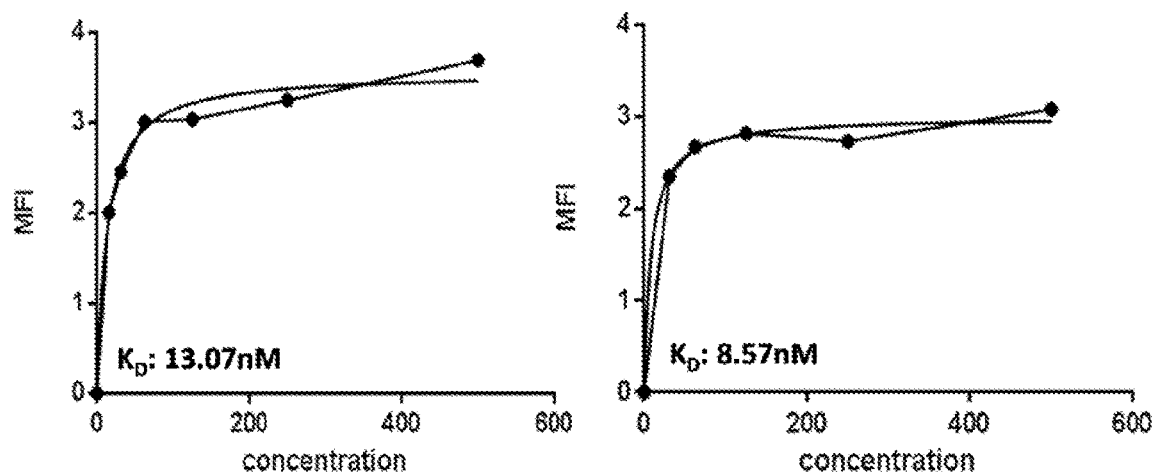
FIGS. 4A-4C. Binding affinity and cell internalization of truncated P19 (tP19).
Figure 4B:
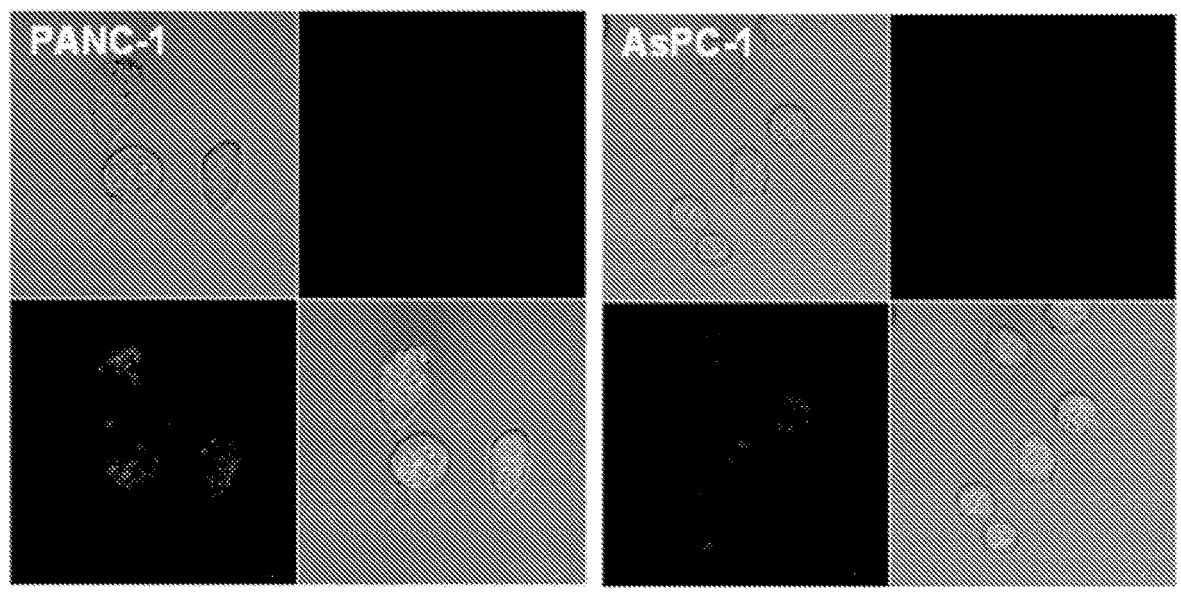
Figure 4C:
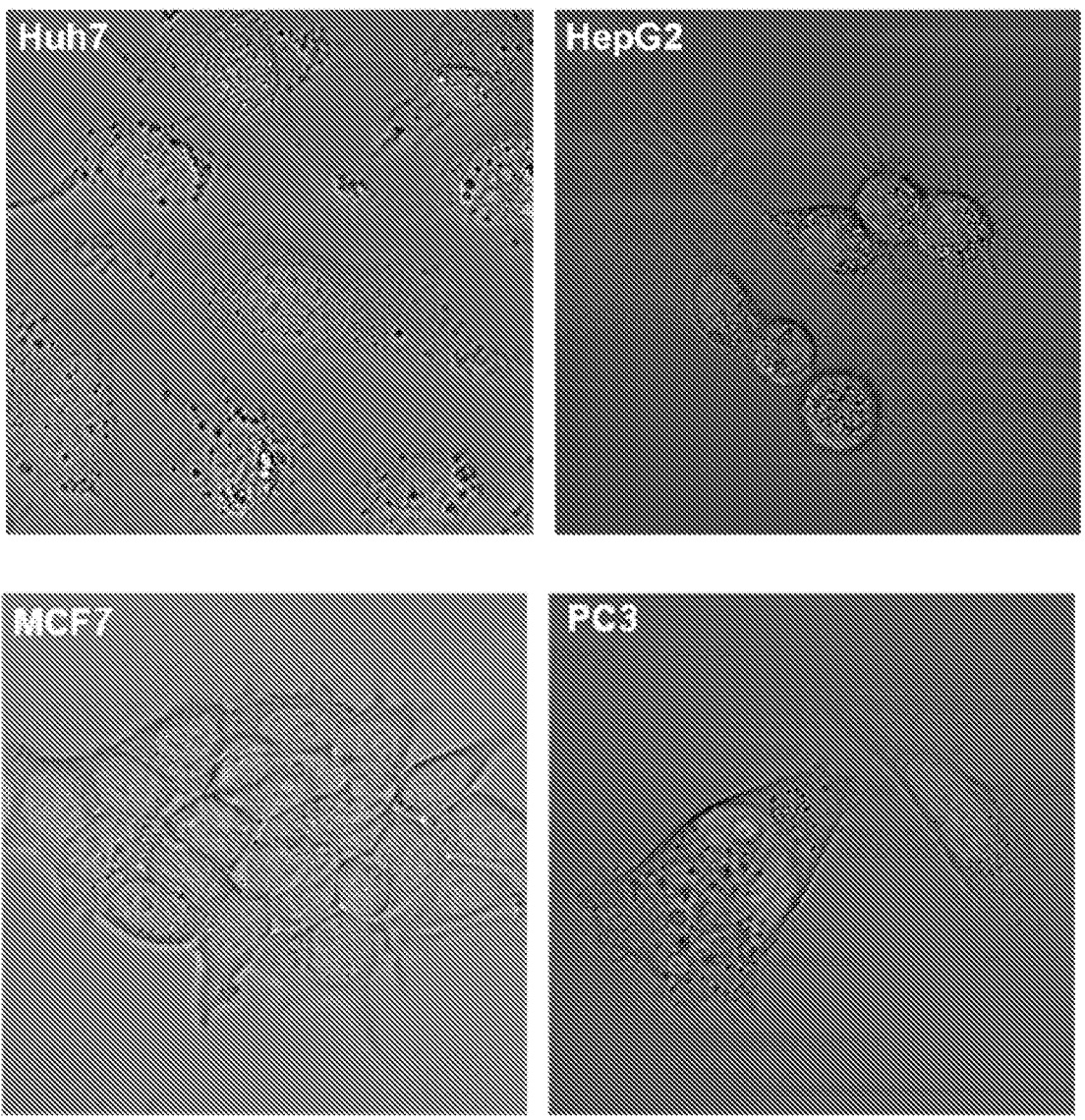

To characterize the DNA damage generated by P19-dFdCMP and P19-5FdUM, the appearance of the phosphorylated form of the histone H2AX (rH2AX) Ser 139, a specific biomarker of DNA double-strand breaks (DSBs) [11], was measured by immune assay and flow cytometry. Our data clearly indicate that P19-dFdCMP and P19-5FdUMP induce strong incidents of rH2AX significantly in nuclear, comparing cell control and P19 only (FIGS. 3A-3B). When quantify the incidents of rH2AX, P19-dFdCMP induced rH2AX of sixteen times more than control, P19-5FdUMP induced twelve times more than control (FIG. 3B).

REFERENCES (EXAMPLE 1)

[1] Burris H A, 3rd, Moore M J, Andersen J, Green M R, Rothenberg M L, et al. (1997) Improvements in survival and clinical benefit with gemcitabine as first-line therapy for patients with advanced pancreas cancer: a randomized trial. J Clin Oncol 15: 2403-2413; [2] Farrell J J, Elsaleh H, Garcia M, Lai R, Ammar A, et al. (2009) Human equilibrative nucleoside transporter 1 levels predict response to gemcitabine in patients with pancreatic cancer. Gastroenterology 136: 187-195; [3] Giovannetti E, Del Tacca M, Mey V, Funel N, Nannizzi S, et al. (2006) Transcription analysis of human equilibrative nucleoside transporter-1 predicts survival in pancreas cancer patients treated with gemcitabine. Cancer Res 66: 3928-3935; [4] Ohhashi S, Ohuchida K, Mizumoto K, Fujita H, Egami T, et al. (2008) Downregulation of deoxycytidine kinase enhances acquired resistance to gemcitabine in pancreatic cancer. Anticancer Res 28: 2205-2212; [5] Wu W, Sigmond J, Peters G J, Borch R F (2007) Synthesis and biological activity of a gemcitabine phosphoramidate prodrug. J Med Chem 50: 3743-3746; [6] Huang P, Chubb S, Hertel L W, Grindey G B, Plunkett W (1991) Action of 2',2'-difluorodeoxycytidine on DNA synthesis. Cancer Res 51: 6110-6117; [7] L. Pauling (1945) The Nature of the Chemical Bond: Comell University Press, Ithaca; [8] Matuo R, Sousa F G, Escargueil A E, Grivicich I, Garcia-Santos D, et al. (2009) 5-Fluorouracil and its active metabolite FdUMP cause DNA damage in human SW620 colon adenocarcinoma cell line. J Appl Toxicol 29: 308-316;

[9] Ruiz van Haperen V W, Veerman G, Vermorken J B, Peters G J (1993) 2',2'-Difluoro-deoxycytidine (gemcitabine) incorporation into RNA and DNA of tumour cell lines. Biochem Pharmacol 46: 762-766; [10] Pourquier P, Gioffre C, Kohlhagen G, Urasaki Y, Goldwasser F, et al. (2002) Gemcitabine (2',2'-difluoro-2'-deoxycytidine), an antimetabolite that poisons topoisomerase I. *Clin Cancer Res* 8: 2499-2504; [11] Soares D G, Escargueil A E, Poindessous V, Sarasin A, de Gramont A, et al. (2007) Replication and homologous recombination repair regulate DNA double-strand break formation by the antitumor alkylator ecteinascidin 743. Proc Natl Acad Sci USA 104: 13062-13067.

Example 2—Aptamer Drug Conjugates (ApDCs) of MMAE and DM1 Inhibit Cell Growth Through Cell Cycle Arrest in Pancreatic Adenonocarcinoma (PDAC Abstract. Monomethyl auristatin E (MMAE) and drug maytansinoids 1 (DM1) are highly potent antimitotic drugs that bind to microtubules. However, because of high toxicity, both MMAE and DM1 are not used alone as drug themselves. Antibody-drug conjugates (ADCs) have been designed to deliver highly toxic cytotoxic agents into cells. Nonetheless, immunogenicity of antibody based delivery of drugs is still challenging. In this study, we investigated the antitumor effect of MMAE and DM1 delivery by low immunogenic aptamer-drug conjugates (ApDCs), which is highly cancer specific. MMAE or DM1 was conjugated to 5' end of sticky sequence (MMAE-SE and DM1-SE). MMAE-SE or DM1-SE was annealed with P19 with sticky sequence for the ApDCs. The cytotoxic effects of MMAE-tP19-ApDC and DM1-tP19-ApDC against pancreatic cancer and other type of cancers were investigated. MMAE-tP19-ApDC induced cell cycle arrest, increasing G2/M significantly, consequently inhibited cell proliferation in vitro. Surprisingly, the cytotoxicity of MMAE-tP19-ApDC and DM1-tP19-ApDC in normal cells, BJ, and negative cell line, MCF7, was limited. Our results indicate that our approach decreases cytotoxicity in non-targeting cells drastically and minimizes the side effects.

Materials and Methods
Cell Lines.

The following cell lines were purchased from the American Type Culture Collection (ATCC), PANC-1 (CRL-1469), AsPC-1 (CRL-1682), MCF7 (HTB-22), HCT116 (CCL-247), and BJ (CRL-2522). U251-MG was purchased in Sigma. The cells were cultured according to the cell bank's instructions.

Flow Cytometry-Based Binding Assays.

Aptamer binding and uptake was also assessed by flow cytometry. For the assay, the PANC-1 cells were detached using Accutase (sigma), washed with PBS and suspended in binding buffer. Next, Cy3-labeled aptamers were added and incubated with PANC-1 cells for 30 minutes at 37° C. Cells were washed with binding buffer and immediately analyzed by Fortessa flow cytometry (BD). For the exclusion of dead cells, 4'6'-diamidino-2-phenylindole (DAPI) (1 µg/ml) was used. Each flow-cytometry assay was performed in triplicate. The data were analyzed with FlowJo software.

Dissociation Constants.

To determine the apparent dissociation constant ($K_D$) of aptamers to PANC-1 cells, the mean fluorescence intensity (MFI) was calculated for each concentration and for the unselected library controls. The values for the controls were considered to be background fluorescence and were subtracted from the values for the aptamers, as previously described by Sefah et al.[34] The dissociation constants were calculated using a one-site binding model. The non-linear curve regression was performed using Graph Pad Prism (GraphPad Software, La Jolla, Calif., USA).

MMAE and DM1 Conjugation with 'Sticky Bridges.'

The same concentration of tP19-SE, MMAE-SE or DM1-SE was folded in binding buffer (phosphate-buffered saline solution [DPBS] without $Ca^{2+}$ and $Mg^{2+}$, 5 mM $MgCl_2$) at 95° C. for 5 minutes and slowly cooled down and incubated at 37° C. for 20 minutes more to make the conjugate using 'sticky sequence' technology. The sequences are provided following, where bold letters denote sticky sequences to anneal tP19 to MMAE1 and DM1; "o" denotes C3 carbon linker; fC and fU denotes 2'fluoro pyrimidines; and mA and mG denote 2'O methyl purines.

tP19 (truncated P19 with sticky sequence):

(SEQ ID NO: 11)
fCfUfCAAfUGGfCGAAfUGfCfCfCGfCfCfUAAfUAGGGooo oooomAmGfUfUfUfUfUfUmAfCmAfUfUfUfUmG MMAE with sticky sequence:

(SEQ ID NO: 16)
MMAEooooofCmAmAmAmAfUmGfUmAmAmAmAmAfCfU

DM1 with sticky sequence:

(SEQ ID NO: 17)
DM1ooooofCmAmAmAmAfUmGfUmAmAmAmAmAfCfU

Live-Cell Confocal Imaging.

For the aptamer internalization studies, $1 \times 10^5$ cells were seeded in 35 mm glass-bottom dishes (MatTek, Ashland, Mass., USA) and grown in medium for 24 hrs. The RNAs were labeled with Cy3 using the Cy3 Silencer siRNA labeling kit (Ambion, Tex., USA.). Cy3-labeled RNAs were added to the cells at 200 nM or 500 nM and incubated for 2 hour. The images were taken using a Zeiss LSM 510 Meta Inverted 2 photon confocal microscope system using a C-Apo 40x/1.2NA water immersion objective.

Cell Proliferation Assay.

$5 \times 10^3$ cells/well of PANC-1 (pancreatic cancer cells), MCF7 (breast cancer cell), U251-MG (glioblastoma), HCT116 (colon cancer cells) and BJ (normal fibroblast cells) were seeded in 96 well plates one day before. tP19-MMAE at various concentration (from 1 uM to 0.45 uM, 3 folds dilution) were incubated for 4 hours. After 4 hours incubation, cells were washed and added with new media. After 48 hrs and 72 hrs, the inhibition of cell proliferation was measured by MTT assay. tP19-MMAE inhibited cell growth significantly in PANC-1, U251 and HCT116, minimizing the effect in normal cells.

Cell Cycle Analysis.

For cell cycle evaluation, $5 \times 10^5$ cells were treated with tP19, tP19-MMAE and -DM1 at 500 nM for 48 and 72 hrs. After treatments, cells were harvested and fixed in 70% ethanol for overnight. The samples were washed with PBS. After centrifuge, the cells were resuspended in 500 µl Propidium Iodide (PI)/Triton X-100 staining solution (to 10 ml of 0.1% (v/v) Triton X-100, 2 mg DNase-free RNase A and 0.40 ml of 500 µg/ml PI) for 37° C. for 15 minutes. The cells were analyzed with flow cytometry. The data was analyzed by ModFit software.

Statistical Analysis.

Statistically significant differences were determined by Students t-test and ANOVA using Graph Pad Prism software (GraphPad Software, La Jolla, Calif., USA).

Results

Truncated tP19 (tP19) Keep the Binging Affinity to Target Cells as the Full Length of P19.

To increase the binding affinity of P19 to target cells, P19 was truncated to minimize the length of P19. For the truncated P19 (tP19) that is 28 bps in length, the measured binding affinity was 8.57 nM, which is slightly increased (FIG. 4A, right), comparing with full length P19 (FIG. 4A, left). The tP19 was internalized into PANC-1 and AsPC-1 cells (FIG. 4B), but not in non-pancreatic cancer cell lines (FIG. 4C). Consequently, tP19 retains the binding affinity of P19.

The tP19 Conjugates with MMAE and DM1 Via Sticky Sequence.

For the targeted delivery of chemotoxins, MMAE (MMAE1-SE) and DM1 (DM1-SE) were covalently attached to the 5' end of sticky sequence (FIG. 5A). After chemical conjugation, the compound was purified with HPLC. tP19 with sticky sequence (tP19-SE) was chemically synthesized and purified. The tP19-SE and MMAE-SE or DM1- were annealed in the folding buffers for the ApDCs (FIG. 5B). The MMAE-tP19-ApDC labeled with Cy3 was internalized into PANC- (FIG. 5C, left) but not in MCF7 cells (FIG. 5C, right).

The tP19-MMAE Induced the Cell Cycle Arrest.

Because MMAE is an antimitotic drug that binds to microtubules, the cycle arrest effects of MMAE-tP19-ApDC was measured. At 48 and 72 hours, MMAE-tP19-ApDC drastically increased G2/M phase in PANC-1 cells (FIG. 6).

The tP19-MMAE1 and -DM1 Inhibit Cell Proliferation.

To determine the cytotoxicity of MMAE-tP19-ApDC and DM1-tP19-ApDC, MTT assays were performed. MMAE-tP19-ApDC and DM1-tP19-ApDC significantly inhibited cell proliferation (FIGS. 7A-7B, FIGS. 8 and 9). MMAE-tP19-ApDC and DM1-tP19-ApDC showed no cytotoxicity in normal fibroblast BJ cells. MMAE-tP19-ApDC showed more potent cytotoxicity than DM1-tP19-ApDC. Both MMAE-tP19-ApDC and DM1-tP19-ApDC showed the cross-activity in undifferentiated and invasive cancer cells, U251 and HCT116 cells.

What is claimed is:

1. A composition comprising an aptamer consisting of a nucleic acid sequence of SEQ ID NO: 3, and an anticancer agent, wherein said aptamer is bound to said anticancer agent, wherein said anticancer agent is a nucleotide analogue, a nucleoside analogue, a pyrimidine analogue or a purine analogue and wherein one or more nucleotides within said aptamer are replaced by said anticancer agent thereby incorporating said anticancer agent into said aptamer sequence.

2. The composition of claim 1, wherein:
   (a) said anticancer agent is gemcitabine, 5-flurouracil or a metabolite thereof;
   (b) said anticancer agent is gemcitabine monophosphate (dFdCMP) or 5-F-uridine monophosphate (5FdUMP); or
   (c) said anticancer agent is present within the nucleic acid sequence of said aptamer.

3. The composition of claim 2, wherein said anticancer agent is present within the nucleic acid sequence of said aptamer, and further wherein:
   (a) said anticancer agent is gemcitabine or gemcitabine analogue, wherein said gemcitabine or gemcitabine analogue is present within the nucleic acid sequence at one or more cytidine positions; or
   (b) said anticancer agent is 5-fluorouracil or 5-fluorouracil analogue, wherein said 5-fluorouracil or 5-fluorouracil analogue is present within the nucleic acid sequence at one or more uridine positions.

4. The composition of claim 1, wherein the aptamer consisting of a nucleic acid sequence of SEQ ID NO:3 forms a complex with a cellular receptor.

5. The composition of claim 4, wherein:
   (a) said cellular receptor is cell surface HSP70;
   (b) said cellular receptor is cell surface mHSP70;
   (c) said cellular receptor is cell surface HSP90;
   (d) said cellular receptor is cell surface vimentin; or
   (e) said cellular receptor is present on a cancer cell.

6. The composition of claim 5, wherein:
   (a) said cancer cell is a cancer stem cell;
   (b) said cancer cell is an undifferentiated cancer cell;
   (c) said cancer cell is an undifferentiated metastatic cancer cell; or
   (d) said cancer cell is a pancreatic cancer cell, a glioblastoma cell, a colon cancer cell.

7. The composition of claim 1, wherein said aptamer consists of:
   (a) a nucleic acid sequence of SEQ ID NO:3, and said aptamer is bound to PBD, MMAE, DM1, oxaliplatin, irinotecan or doxorubicin; or
   (b) a nucleic acid sequence of SEQ ID NO:3, wherein one or more nucleotides of said nucleic acid sequence are replaced with dFdCMP or 5FdUMP.

8. A pharmaceutical formulation comprising the composition of claim 1 and a pharmaceutically acceptable excipient.

9. A method of treating cancer, the method comprising administering to a subject in need thereof an effective amount of the composition of claim 1.

10. The method of claim 9, wherein said cancer overexpresses HSP70 or HSP90 or vimentin.

11. The method of claim 9, wherein said cancer is an undifferentiated metastatic cancer.

12. The method of claim 9, wherein said cancer is pancreatic cancer, colon cancer or glioblastoma.

* * * * *

SEQUENCE LISTING

```
<160> NUMBER OF SEQ ID NOS: 19

<210> SEQ ID NO 1
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 1
gggagacaag aauaaacgcu caaugcgcug aaugcccagc cgugaaagcg ucgauuucca     60
uccuucgaca ggaggcucac aacaggc                                         87

<210> SEQ ID NO 2
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 2
gggagacaag aauaaacgcu caauggcgaa ugcccgccua auagggcguu augacuuguu     60
gaguucgaca ggaggcucac aacaggc                                         87

<210> SEQ ID NO 3
<211> LENGTH: 28
<212> TYPE: RNA
<213> ORGANISM: Artificial Sequence
<220> FEATURE:
<223> OTHER INFORMATION: Synthetic polynucleotide

<400> SEQUENCE: 3
cucaauggcg aaugcccgcc uaauaggg                                        28

<210> SEQ ID NO 4
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 4
```

```
gggagacaag aauaaacgcu caaaguugcg gcccaaccgu uuaauucaga auagugugau    60
gccuucgaca ggaggcucac aacaggc                                       87

<210> SEQ ID NO 5
<211> LENGTH: 71
<212> TYPE: RNA
<213> ORGANISM: Artificial Sequence
<220> FEATURE:
<223> OTHER INFORMATION: Synthetic polynucleotide

<400> SEQUENCE: 5
gggagacaag aauaaacgcu caacaaugga gcguuaaacg ugagccauuc gacaggaggc    60
ucacaacagg c                                                        71

<210> SEQ ID NO 6
<211> LENGTH: 87
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (57)..(57)
<223> OTHER INFORMATION: Residue modified with 2'-fluoro

<400> SEQUENCE: 6
gggagacaag aauaaacgcu caaggccaug uugaaugccc aacuaagcuu ugagcuuugg    60
agcuucgaca ggaggcucac aacaggc                                       87

<210> SEQ ID NO 7
<211> LENGTH: 87
<212> TYPE: RNA
<213> ORGANISM: Artificial Sequence
<220> FEATURE:
<223> OTHER INFORMATION: Synthetic polynucleotide

<400> SEQUENCE: 7
gggagacaag aauaaacgcu caaaugauug cccauucggu uaugcuugcg cuuccuaaag    60
agcuucgaca ggaggcucac aacaggc                                       87

<210> SEQ ID NO 8
<211> LENGTH: 8
<212> TYPE: RNA
<213> ORGANISM: Artificial Sequence
<220> FEATURE:
<223> OTHER INFORMATION: Synthetic polynucleotide

<400> SEQUENCE: 8 gawugccc                                                             8

<210> SEQ ID NO 9
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
```

```
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (24)..(24)
<223> OTHER INFORMATION: Residue modified with 2'-fluoro
<220> FEATURE:
<221> NAME/KEY: misc_feature
<222> LOCATION: (26)..(26)
<223> OTHER INFORMATION: Residue modified with 2'-fluoro
<220> FEATURE:
<221> NAME/KEY: misc_feature
<222> LOCATION: (28)..(29)
<223> OTHER INFORMATION: Residue modified with 2'-fluoro
<220> FEATURE:
<221> NAME/KEY: misc_feature
<222> LOCATION: (33)..(33)
<223> OTHER INFORMATION: Residue modified with 2'-fluoro
<220> FEATURE:
<221> NAME/KEY: misc_feature
<222> LOCATION: (35)..(37)
<223> OTHER INFORMATION: Residue modified with 2'-fluoro
<220> FEATURE:
<221> NAME/KEY: misc_feature
<222> LOCATION: (40)..(41)
<223> OTHER INFORMATION: Residue modified with 2'-fluoro
<220> FEATURE:
<221> NAME/KEY: misc_feature
<222> LOCATION: (43)..(43)
<223> OTHER INFORMATION: Residue modified with 2'-fluoro
<220> FEATURE:
<221> NAME/KEY: misc_feature
<222> LOCATION: (49)..(49)
<223> OTHER INFORMATION: Residue modified with 2'-fluoro
<220> FEATURE:
<221> NAME/KEY: misc_feature
<222> LOCATION: (51)..(52)
<223> OTHER INFORMATION: Residue modified with 2'-fluoro
<220> FEATURE:
<221> NAME/KEY: misc_feature
<222> LOCATION: (55)..(59)
<223> OTHER INFORMATION: Residue modified with 2'-fluoro
<220> FEATURE:
<221> NAME/KEY: misc_feature
<222> LOCATION: (61)..(66)
<223> OTHER INFORMATION: Residue modified with 2'-fluoro
<220> FEATURE:
<221> NAME/KEY: misc_feature
<222> LOCATION: (69)..(69)
<223> OTHER INFORMATION: Residue modified with 2'-fluoro
<220> FEATURE:
<221> NAME/KEY: misc_feature
<222> LOCATION: (76)..(78)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-fluoro
<220> FEATURE:
<221> NAME/KEY: misc_feature
<222> LOCATION: (83)..(83)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified at 3'-position with C3 carbon
      spacers linked to residue at 3'-position
<220> FEATURE:
<221> NAME/KEY: misc_feature
<222> LOCATION: (88)..(88)
```

<223> OTHER INFORMATION: Residue modified at 5'-position with C3 carbon
      spacers linked to residue at 5'-position
<220> FEATURE:
<221> NAME/KEY: misc_feature
<222> LOCATION: (88)..(88)
<223> OTHER INFORMATION: Residue modified with 2'-O-methyl
<220> FEATURE:
<221> NAME/KEY: misc_feature
<222> LOCATION: (89)..(89)
<223> OTHER INFORMATION: Residue modified with 2'-O-methyl
<220> FEATURE:
<221> NAME/KEY: misc_feature
<222> LOCATION: (90)..(95)
<223> OTHER INFORMATION: Residue modified with 2'-fluoro
<220> FEATURE:
<221> NAME/KEY: misc_feature
<222> LOCATION: (96)..(96)
<223> OTHER INFORMATION: Residue modified with 2'-O-methyl
<220> FEATURE:
<221> NAME/KEY: misc_feature
<222> LOCATION: (97)..(97)
<223> OTHER INFORMATION: Residue modified with 2'-fluoro
<220> FEATURE:
<221> NAME/KEY: misc_feature
<222> LOCATION: (98)..(98)
<223> OTHER INFORMATION: Residue modified with 2'-O-methyl
<220> FEATURE:
<221> NAME/KEY: misc_feature
<222> LOCATION: (99)..(102)
<223> OTHER INFORMATION: Residue modified with 2'-fluoro
<220> FEATURE:
<221> NAME/KEY: misc_feature
<222> LOCATION: (103)..(103)
<223> OTHER INFORMATION: Residue modified with 2'-O-methyl

<400> SEQUENCE: 9
gggagacaag aauaaacgcu caaugcgcug aaugcccagc cgugaaagcg ucgauuucca    60
uccuucgaca ggaggcucac aacaggcagu uuuuuacauu uug                    103

<210> SEQ ID NO 10
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (24)..(24)
<223> OTHER INFORMATION: Residue modified with 2'-fluoro
<220> FEATURE:
<221> NAME/KEY: misc_feature
<222> LOCATION: (27)..(27)
<223> OTHER INFORMATION: Residue modified with 2'-fluoro
<220> FEATURE:
<221> NAME/KEY: misc_feature
<222> LOCATION: (31)..(31)
<223> OTHER INFORMATION: Residue modified with 2'-fluoro
<220> FEATURE:
<221> NAME/KEY: misc_feature
<222> LOCATION: (33)..(35)

```
<223> OTHER INFORMATION: Residue modified with 2'-fluoro
<220> FEATURE:
<221> NAME/KEY: misc_feature
<222> LOCATION: (37)..(39)
<223> OTHER INFORMATION: Residue modified with 2'-fluoro
<220> FEATURE:
<221> NAME/KEY: misc_feature
<222> LOCATION: (42)..(43)
<223> OTHER INFORMATION: Residue modified with 2'-fluoro
<220> FEATURE:
<221> NAME/KEY: misc_feature
<222> LOCATION: (47)..(47)
<223> OTHER INFORMATION: Residue modified with 2'-fluoro
<220> FEATURE:
<221> NAME/KEY: misc_feature
<222> LOCATION: (49)..(50)
<223> OTHER INFORMATION: Residue modified with 2'-fluoro
<220> FEATURE:
<221> NAME/KEY: misc_feature
<222> LOCATION: (52)..(52)
<223> OTHER INFORMATION: Residue modified with 2'-fluoro
<220> FEATURE:
<221> NAME/KEY: misc_feature
<222> LOCATION: (55)..(57)
<223> OTHER INFORMATION: Residue modified with 2'-fluoro
<220> FEATURE:
<221> NAME/KEY: misc_feature
<222> LOCATION: (59)..(60)
<223> OTHER INFORMATION: Residue modified with 2'-fluoro
<220> FEATURE:
<221> NAME/KEY: misc_feature
<222> LOCATION: (64)..(66)
<223> OTHER INFORMATION: Residue modified with 2'-fluoro
<220> FEATURE:
<221> NAME/KEY: misc_feature
<222> LOCATION: (69)..(69)
<223> OTHER INFORMATION: Residue modified with 2'-fluoro
<220> FEATURE:
<221> NAME/KEY: misc_feature
<222> LOCATION: (76)..(78)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-fluoro
<220> FEATURE:
<221> NAME/KEY: misc_feature
<222> LOCATION: (83)..(83)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified at 3'-position with C3 carbon
    spacers linked to residue at 3'-position
<220> FEATURE:
<221> NAME/KEY: misc_feature
<222> LOCATION: (88)..(88)
<223> OTHER INFORMATION: Residue modified at 5'-position with C3 carbon
    spacers linked to residue at 5'-position
<220> FEATURE:
<221> NAME/KEY: misc_feature
<222> LOCATION: (88)..(88)
<223> OTHER INFORMATION: Residue modified with 2'-O-methyl
<220> FEATURE:
<221> NAME/KEY: misc_feature
<222> LOCATION: (89)..(89)
<223> OTHER INFORMATION: Residue modified with 2'-O-methyl
<220> FEATURE:
<221> NAME/KEY: misc_feature
<222> LOCATION: (89)..(95)
<223> OTHER INFORMATION: Residue modified with 2'-fluoro
<220> FEATURE:
<221> NAME/KEY: misc_feature
<222> LOCATION: (96)..(96)
<223> OTHER INFORMATION: Residue modified with 2'-O-methyl
```

```
<220> FEATURE:
<221> NAME/KEY: misc_feature
<222> LOCATION: (97)..(97)
<223> OTHER INFORMATION: Residue modified with 2'-fluoro
<220> FEATURE:
<221> NAME/KEY: misc_feature
<222> LOCATION: (98)..(98)
<223> OTHER INFORMATION: Residue modified with 2'-O-methyl
<220> FEATURE:
<221> NAME/KEY: misc_feature
<222> LOCATION: (99)..(102)
<223> OTHER INFORMATION: Residue modified with 2'-fluoro
<220> FEATURE:
<221> NAME/KEY: misc_feature
<222> LOCATION: (103)..(103)
<223> OTHER INFORMATION: Residue modified with 2'-O-methyl

<400> SEQUENCE: 10
gggagacaag aauaaacgcu caauggcgaa ugcccgccua auagggcguu augacuuguu      60
gaguucgaca ggaggcucac aacaggcagu uuuuuacauu uug                      103

<210> SEQ ID NO 11
<211> LENGTH: 44
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(3)
<223> OTHER INFORMATION: Residue modified with 2'-fluoro
<220> FEATURE:
<221> NAME/KEY: misc_feature
<222> LOCATION: (6)..(6)
<223> OTHER INFORMATION: Residue modified with 2'-fluoro
<220> FEATURE:
<221> NAME/KEY: misc_feature
<222> LOCATION: (9)..(9)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (15)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (24)..(24)
<223> OTHER INFORMATION: Residue modified with 2'-fluoro
<220> FEATURE:
<221> NAME/KEY: misc_feature
<222> LOCATION: (28)..(28)
<223> OTHER INFORMATION: Residue modified at 3'-position with C3 carbon
      spacers linked to residue at 3'-position
<220> FEATURE:
<221> NAME/KEY: misc_feature
<222> LOCATION: (29)..(29)
<223> OTHER INFORMATION: Residue modified at 5'-position with C3 carbon
      spacers linked to residue at 5'-position
<220> FEATURE:
<221> NAME/KEY: misc_feature
<222> LOCATION: (29)..(29)
<223> OTHER INFORMATION: Residue modified with 2'-O-methyl
<220> FEATURE:
<221> NAME/KEY: misc_feature
<222> LOCATION: (30)..(30)
<223> OTHER INFORMATION: Residue modified with 2'-O-methyl
<220> FEATURE:
<221> NAME/KEY: misc_feature
<222> LOCATION: (31)..(36)
```

```
<223> OTHER INFORMATION: Residue modified with 2'-fluoro
<220> FEATURE:
<221> NAME/KEY: misc_feature
<222> LOCATION: (37)..(37)
<223> OTHER INFORMATION: Residue modified with 2'-O-methyl
<220> FEATURE:
<221> NAME/KEY: misc_feature
<222> LOCATION: (38)..(38)
<223> OTHER INFORMATION: Residue modified with 2'-fluoro
<220> FEATURE:
<221> NAME/KEY: misc_feature
<222> LOCATION: (39)..(39)
<223> OTHER INFORMATION: Residue modified with 2'-O-methyl
<220> FEATURE:
<221> NAME/KEY: misc_feature
<222> LOCATION: (40)..(43)
<223> OTHER INFORMATION: Residue modified with 2'-fluoro
<220> FEATURE:
<221> NAME/KEY: misc_feature
<222> LOCATION: (44)..(44)
<223> OTHER INFORMATION: Residue modified with 2'-O-methyl

<400> SEQUENCE: 11
cucaauggcg aaugcccgcc uaauagggag uuuuuuacau uuug          44

<210> SEQ ID NO 12
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (26)..(27)
<223> OTHER INFORMATION: Residue modified with 2'-fluoro
<220> FEATURE:
<221> NAME/KEY: misc_feature
<222> LOCATION: (29)..(29)
<223> OTHER INFORMATION: Residue modified with 2'-fluoro
<220> FEATURE:
<221> NAME/KEY: misc_feature
<222> LOCATION: (32)..(34)
<223> OTHER INFORMATION: Residue modified with 2'-fluoro
<220> FEATURE:
<221> NAME/KEY: misc_feature
<222> LOCATION: (37)..(38)
<223> OTHER INFORMATION: Residue modified with 2'-fluoro
<220> FEATURE:
<221> NAME/KEY: misc_feature
<222> LOCATION: (40)..(42)
<223> OTHER INFORMATION: Residue modified with 2'-fluoro
<220> FEATURE:
<221> NAME/KEY: misc_feature
<222> LOCATION: (45)..(47)
<223> OTHER INFORMATION: Residue modified with 2'-fluoro
<220> FEATURE:
<221> NAME/KEY: misc_feature
<222> LOCATION: (52)..(52)
<223> OTHER INFORMATION: Residue modified with 2'-fluoro
<220> FEATURE:
<221> NAME/KEY: misc_feature
```

```
<222> LOCATION: (55)..(55)
<223> OTHER INFORMATION: Residue modified with 2'-fluoro
<220> FEATURE:
<221> NAME/KEY: misc_feature
<222> LOCATION: (57)..(57)
<223> OTHER INFORMATION: Residue modified with 2'-fluoro
<220> FEATURE:
<221> NAME/KEY: misc_feature
<222> LOCATION: (60)..(60)
<223> OTHER INFORMATION: Residue modified with 2'-fluoro
<220> FEATURE:
<221> NAME/KEY: misc_feature
<222> LOCATION: (62)..(66)
<223> OTHER INFORMATION: Residue modified with 2'-fluoro
<220> FEATURE:
<221> NAME/KEY: misc_feature
<222> LOCATION: (69)..(69)
<223> OTHER INFORMATION: Residue modified with 2'-fluoro
<220> FEATURE:
<221> NAME/KEY: misc_feature
<222> LOCATION: (76)..(78)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-fluoro
<220> FEATURE:
<221> NAME/KEY: misc_feature
<222> LOCATION: (83)..(83)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified at 3'-position with C3 carbon
      spacers linked to residue at 3'-position
<220> FEATURE:
<221> NAME/KEY: misc_feature
<222> LOCATION: (88)..(88)
<223> OTHER INFORMATION: Residue modified at 5'-position with C3 carbon
      spacers linked to residue at 5'-position
<220> FEATURE:
<221> NAME/KEY: misc_feature
<222> LOCATION: (88)..(88)
<223> OTHER INFORMATION: Residue modified with 2'-O-methyl
<220> FEATURE:
<221> NAME/KEY: misc_feature
<222> LOCATION: (89)..(89)
<223> OTHER INFORMATION: Residue modified with 2'-O-methyl
<220> FEATURE:
<221> NAME/KEY: misc_feature
<222> LOCATION: (90)..(95)
<223> OTHER INFORMATION: Residue modified with 2'-fluoro
<220> FEATURE:
<221> NAME/KEY: misc_feature
<222> LOCATION: (96)..(96)
<223> OTHER INFORMATION: Residue modified with 2'-O-methyl
<220> FEATURE:
<221> NAME/KEY: misc_feature
<222> LOCATION: (97)..(97)
<223> OTHER INFORMATION: Residue modified with 2'-fluoro
<220> FEATURE:
<221> NAME/KEY: misc_feature
<222> LOCATION: (98)..(98)
<223> OTHER INFORMATION: Residue modified with 2'-O-methyl
<220> FEATURE:
<221> NAME/KEY: misc_feature
<222> LOCATION: (99)..(102)
<223> OTHER INFORMATION: Residue modified with 2'-fluoro
<220> FEATURE:
<221> NAME/KEY: misc_feature
<222> LOCATION: (103)..(103)
<223> OTHER INFORMATION: Residue modified with 2'-O-methyl

<400> SEQUENCE: 12
```
gggagacaag aauaaacgcu caaaguugcg gcccaaccgu uuaauucaga auagugugau    60
gccuucgaca ggaggcucac aacaggcagu uuuuuacauu uug                    103

```
<210> SEQ ID NO 13
<211> LENGTH: 87
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (24)..(24)
<223> OTHER INFORMATION: Residue modified with 2'-fluoro
<220> FEATURE:
<221> NAME/KEY: misc_feature
<222> LOCATION: (27)..(27)
<223> OTHER INFORMATION: Residue modified with 2'-fluoro
<220> FEATURE:
<221> NAME/KEY: misc_feature
<222> LOCATION: (30)..(30)
<223> OTHER INFORMATION: Residue modified with 2'-fluoro
<220> FEATURE:
<221> NAME/KEY: misc_feature
<222> LOCATION: (32)..(32)
<223> OTHER INFORMATION: Residue modified with 2'-fluoro
<220> FEATURE:
<221> NAME/KEY: misc_feature
<222> LOCATION: (34)..(35)
<223> OTHER INFORMATION: Residue modified with 2'-fluoro
<220> FEATURE:
<221> NAME/KEY: misc_feature
<222> LOCATION: (39)..(39)
<223> OTHER INFORMATION: Residue modified with 2'-fluoro
<220> FEATURE:
<221> NAME/KEY: misc_feature
<222> LOCATION: (41)..(41)
<223> OTHER INFORMATION: Residue modified with 2'-fluoro
<220> FEATURE:
<221> NAME/KEY: misc_feature
<222> LOCATION: (45)..(46)
<223> OTHER INFORMATION: Residue modified with 2'-fluoro
<220> FEATURE:
<221> NAME/KEY: misc_feature
<222> LOCATION: (48)..(50)
<223> OTHER INFORMATION: Residue modified with 2'-fluoro
<220> FEATURE:
<221> NAME/KEY: misc_feature
<222> LOCATION: (53)..(53)
<223> OTHER INFORMATION: Residue modified with 2'-fluoro
<220> FEATURE:
<221> NAME/KEY: misc_feature
<222> LOCATION: (60)..(62)
<223> OTHER INFORMATION: Residue modified with 2'-fluoro
<220> FEATURE:
<221> NAME/KEY: misc_feature
<222> LOCATION: (64)..(64)
<223> OTHER INFORMATION: Residue modified with 2'-fluoro
<220> FEATURE:
<221> NAME/KEY: misc_feature
<222> LOCATION: (67)..(67)
<223> OTHER INFORMATION: Residue modified with 2'-fluoro
```

```
<220> FEATURE:
<221> NAME/KEY: misc_feature
<222> LOCATION: (71)..(71)
<223> OTHER INFORMATION: Residue modified with 2'-fluoro
<220> FEATURE:
<221> NAME/KEY: misc_feature
<222> LOCATION: (71)..(71)
<223> OTHER INFORMATION: Residue modified at 3'-position with C3 carbon
      spacers linked to residue at 3'-position
<220> FEATURE:
<221> NAME/KEY: misc_feature
<222> LOCATION: (72)..(72)
<223> OTHER INFORMATION: Residue modified at 5'-position with C3 carbon
      spacers linked to residue at 5'-position
<220> FEATURE:
<221> NAME/KEY: misc_feature
<222> LOCATION: (72)..(72)
<223> OTHER INFORMATION: Residue modified with 2'-O-methyl
<220> FEATURE:
<221> NAME/KEY: misc_feature
<222> LOCATION: (73)..(73)
<223> OTHER INFORMATION: Residue modified with 2'-O-methyl
<220> FEATURE:
<221> NAME/KEY: misc_feature
<222> LOCATION: (74)..(79)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-O-methyl
<220> FEATURE:
<221> NAME/KEY: misc_feature
<222> LOCATION: (81)..(81)
<223> OTHER INFORMATION: Residue modified with 2'-fluoro
<220> FEATURE:
<221> NAME/KEY: misc_feature
<222> LOCATION: (82)..(82)
<223> OTHER INFORMATION: Residue modified with 2'-O-methyl
<220> FEATURE:
<221> NAME/KEY: misc_feature
<222> LOCATION: (83)..(86)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-O-methyl

<400> SEQUENCE: 13
gggagacaag aauaaacgcu caacaaugga gcguuaaacg ugagccauuc gacaggaggc    60
ucacaacagg caguuuuuua cauuuug                                       87

<210> SEQ ID NO 14
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (26)..(27)
```

```
<223> OTHER INFORMATION: Residue modified with 2'-fluoro
<220> FEATURE:
<221> NAME/KEY: misc_feature
<222> LOCATION: (29)..(29)
<223> OTHER INFORMATION: Residue modified with 2'-fluoro
<220> FEATURE:
<221> NAME/KEY: misc_feature
<222> LOCATION: (31)..(32)
<223> OTHER INFORMATION: Residue modified with 2'-fluoro
<220> FEATURE:
<221> NAME/KEY: misc_feature
<222> LOCATION: (36)..(36)
<223> OTHER INFORMATION: Residue modified with 2'-fluoro
<220> FEATURE:
<221> NAME/KEY: misc_feature
<222> LOCATION: (38)..(40)
<223> OTHER INFORMATION: Residue modified with 2'-fluoro
<220> FEATURE:
<221> NAME/KEY: misc_feature
<222> LOCATION: (43)..(44)
<223> OTHER INFORMATION: Residue modified with 2'-fluoro
<220> FEATURE:
<221> NAME/KEY: misc_feature
<222> LOCATION: (48)..(51)
<223> OTHER INFORMATION: Residue modified with 2'-fluoro
<220> FEATURE:
<221> NAME/KEY: misc_feature
<222> LOCATION: (55)..(58)
<223> OTHER INFORMATION: Residue modified with 2'-fluoro
<220> FEATURE:
<221> NAME/KEY: misc_feature
<222> LOCATION: (63)..(66)
<223> OTHER INFORMATION: Residue modified with 2'-fluoro
<220> FEATURE:
<221> NAME/KEY: misc_feature
<222> LOCATION: (69)..(69)
<223> OTHER INFORMATION: Residue modified with 2'-fluoro
<220> FEATURE:
<221> NAME/KEY: misc_feature
<222> LOCATION: (76)..(78)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-fluoro
<220> FEATURE:
<221> NAME/KEY: misc_feature
<222> LOCATION: (83)..(83)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified at 3'-position with C3 carbon
      spacers linked to residue at 3'-position
<220> FEATURE:
<221> NAME/KEY: misc_feature
<222> LOCATION: (88)..(88)
<223> OTHER INFORMATION: Residue modified at 5'-position with C3 carbon
      spacers linked to residue at 5'-position
<220> FEATURE:
<221> NAME/KEY: misc_feature
<222> LOCATION: (88)..(88)
<223> OTHER INFORMATION: Residue modified with 2'-O-methyl
<220> FEATURE:
<221> NAME/KEY: misc_feature
<222> LOCATION: (89)..(89)
<223> OTHER INFORMATION: Residue modified with 2'-O-methyl
<220> FEATURE:
<221> NAME/KEY: misc_feature
<222> LOCATION: (90)..(95)
<223> OTHER INFORMATION: Residue modified with 2'-fluoro
<220> FEATURE:
<221> NAME/KEY: misc_feature
<222> LOCATION: (96)..(96)
<223> OTHER INFORMATION: Residue modified with 2'-O-methyl
```

<220> FEATURE:
<221> NAME/KEY: misc_feature
<222> LOCATION: (97)..(97)
<223> OTHER INFORMATION: Residue modified with 2'-fluoro
<220> FEATURE:
<221> NAME/KEY: misc_feature
<222> LOCATION: (98)..(98)
<223> OTHER INFORMATION: Residue modified with 2'-O-methyl
<220> FEATURE:
<221> NAME/KEY: misc_feature
<222> LOCATION: (99)..(102)
<223> OTHER INFORMATION: Residue modified with 2'-fluoro
<220> FEATURE:
<221> NAME/KEY: misc_feature
<222> LOCATION: (103)..(103)
<223> OTHER INFORMATION: Residue modified with 2'-O-methyl

<400> SEQUENCE: 14
gggagacaag aauaaacgcu caaggccaug uugaaugccc aacuaagcuu ugagcuuugg    60
agcuucgaca ggaggcucac aacaggcagu uuuuuacauu uug                    103

<210> SEQ ID NO 15
<211> LENGTH: 103
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified with 2'-fluoro
<220> FEATURE:
<221> NAME/KEY: misc_feature
<222> LOCATION: (13)..(13)
<223> OTHER INFORMATION: Residue modified with 2'-fluoro
<220> FEATURE:
<221> NAME/KEY: misc_feature
<222> LOCATION: (17)..(17)
<223> OTHER INFORMATION: Residue modified with 2'-fluoro
<220> FEATURE:
<221> NAME/KEY: misc_feature
<222> LOCATION: (19)..(21)
<223> OTHER INFORMATION: Residue modified with 2'-fluoro
<220> FEATURE:
<221> NAME/KEY: misc_feature
<222> LOCATION: (25)..(25)
<223> OTHER INFORMATION: Residue modified with 2'-fluoro
<220> FEATURE:
<221> NAME/KEY: misc_feature
<222> LOCATION: (28)..(29)
<223> OTHER INFORMATION: Residue modified with 2'-fluoro
<220> FEATURE:
<221> NAME/KEY: misc_feature
<222> LOCATION: (31)..(33)
<223> OTHER INFORMATION: Residue modified with 2'-fluoro
<220> FEATURE:
<221> NAME/KEY: misc_feature
<222> LOCATION: (35)..(37)
<223> OTHER INFORMATION: Residue modified with 2'-fluoro
<220> FEATURE:
<221> NAME/KEY: misc_feature
<222> LOCATION: (40)..(41)
<223> OTHER INFORMATION: Residue modified with 2'-fluoro
<220> FEATURE:
<221> NAME/KEY: misc_feature
<222> LOCATION: (43)..(43)
<223> OTHER INFORMATION: Residue modified with 2'-fluoro
<220> FEATURE:
<221> NAME/KEY: misc_feature
<222> LOCATION: (45)..(47)
<223> OTHER INFORMATION: Residue modified with 2'-fluoro
<220> FEATURE:
<221> NAME/KEY: misc_feature
<222> LOCATION: (49)..(49)
<223> OTHER INFORMATION: Residue modified with 2'-fluoro
<220> FEATURE:

```
<221> NAME/KEY: misc_feature
<222> LOCATION: (51)..(56)
<223> OTHER INFORMATION: Residue modified with 2'-fluoro
<220> FEATURE:
<221> NAME/KEY: misc_feature
<222> LOCATION: (63)..(67)
<223> OTHER INFORMATION: Residue modified with 2'-fluoro
<220> FEATURE:
<221> NAME/KEY: misc_feature
<222> LOCATION: (69)..(69)
<223> OTHER INFORMATION: Residue modified with 2'-fluoro
<220> FEATURE:
<221> NAME/KEY: misc_feature
<222> LOCATION: (76)..(78)
<223> OTHER INFORMATION: Residue modified with 2'-fluoro
<220> FEATURE:
<221> NAME/KEY: misc_feature
<222> LOCATION: (80)..(80)
<223> OTHER INFORMATION: Residue modified with 2'-fluoro
<220> FEATURE:
<221> NAME/KEY: misc_feature
<222> LOCATION: (83)..(83)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified with 2'-fluoro
<220> FEATURE:
<221> NAME/KEY: misc_feature
<222> LOCATION: (87)..(87)
<223> OTHER INFORMATION: Residue modified at 3'-position with C3 carbon
      spacers linked to residue at 3'-position
<220> FEATURE:
<221> NAME/KEY: misc_feature
<222> LOCATION: (88)..(88)
<223> OTHER INFORMATION: Residue modified at 5'-position with C3 carbon
      spacers linked to residue at 5'-position
<220> FEATURE:
<221> NAME/KEY: misc_feature
<222> LOCATION: (88)..(88)
<223> OTHER INFORMATION: Residue modified with 2'-O-methyl
<220> FEATURE:
<221> NAME/KEY: misc_feature
<222> LOCATION: (89)..(89)
<223> OTHER INFORMATION: Residue modified with 2'-O-methyl
<220> FEATURE:
<221> NAME/KEY: misc_feature
<222> LOCATION: (90)..(95)
<223> OTHER INFORMATION: Residue modified with 2'-fluoro
<220> FEATURE:
<221> NAME/KEY: misc_feature
<222> LOCATION: (96)..(96)
<223> OTHER INFORMATION: Residue modified with 2'-O-methyl
<220> FEATURE:
<221> NAME/KEY: misc_feature
<222> LOCATION: (97)..(97)
<223> OTHER INFORMATION: Residue modified with 2'-fluoro
<220> FEATURE:
<221> NAME/KEY: misc_feature
<222> LOCATION: (98)..(98)
<223> OTHER INFORMATION: Residue modified with 2'-O-methyl
<220> FEATURE:
<221> NAME/KEY: misc_feature
<222> LOCATION: (99)..(102)
<223> OTHER INFORMATION: Residue modified with 2'-fluoro
<220> FEATURE:
<221> NAME/KEY: misc_feature
<222> LOCATION: (103)..(103)
<223> OTHER INFORMATION: Residue modified with 2'-O-methyl

<400> SEQUENCE: 15
gggagacaag aauaaacgcu caaaugauug cccauucggu uaugcuugcg cuuccuaaag    60
agcuucgaca ggaggcucac aacaggcagu uuuuuacauu uug                    103

<210> SEQ ID NO 16
<211> LENGTH: 16
```

```
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue modified with MMAE
<220> FEATURE:
<221> NAME/KEY: misc_feature
<222> LOCATION: (1)..(1)
<223> OTHER INFORMATION: Residue modified at 5'-position with C3 carbon
      spacers linked to residue at 5'-position
<220> FEATURE:
<221> NAME/KEY: misc_feature
<222> LOCATION: (1)..(1)
<223> OTHER INFORMATION: Residue modified with 2'-fluoro
<220> FEATURE:
<221> NAME/KEY: misc_feature
<222> LOCATION: (2)..(5)
<223> OTHER INFORMATION: Residue modified with 2'-O-methyl
<220> FEATURE:
<221> NAME/KEY: misc_feature
<222> LOCATION: (6)..(6)
<223> OTHER INFORMATION: Residue modified with 2'-fluoro
<220> FEATURE:
<221> NAME/KEY: misc_feature
<222> LOCATION: (7)..(7)
<223> OTHER INFORMATION: Residue modified with 2'-O-methyl
<220> FEATURE:
<221> NAME/KEY: misc_feature
<222> LOCATION: (8)..(8)
<223> OTHER INFORMATION: Residue modified with 2'-fluoro
<220> FEATURE:
<221> NAME/KEY: misc_feature
<222> LOCATION: (9)..(14)
<223> OTHER INFORMATION: Residue modified with 2'-O-methyl
<220> FEATURE:
<221> NAME/KEY: misc_feature
<222> LOCATION: (15)..(16)
<223> OTHER INFORMATION: Residue modified with 2'-fluoro

<400> SEQUENCE: 16
caaaauguaa aaaacu                                                        16

<210> SEQ ID NO 17
<211> LENGTH: 16
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: Residue modified with DM1
<220> FEATURE:
<221> NAME/KEY: misc_feature
<222> LOCATION: (1)..(1)
<223> OTHER INFORMATION: Residue modified at 5'-position with C3 carbon
      spacers linked to residue at 5'-position
<220> FEATURE:
<221> NAME/KEY: misc_feature
<222> LOCATION: (1)..(1)
<223> OTHER INFORMATION: Residue modified with 2'-fluoro
<220> FEATURE:
<221> NAME/KEY: misc_feature
<222> LOCATION: (2)..(5)
<223> OTHER INFORMATION: Residue modified with 2'-O-methyl
<220> FEATURE:
<221> NAME/KEY: misc_feature
<222> LOCATION: (6)..(6)
<223> OTHER INFORMATION: Residue modified with 2'-fluoro
<220> FEATURE:
<221> NAME/KEY: misc_feature
<222> LOCATION: (7)..(7)
<223> OTHER INFORMATION: Residue modified with 2'-O-methyl
<220> FEATURE:
```

```
<221> NAME/KEY: misc_feature
<222> LOCATION: (8)..(8)
<223> OTHER INFORMATION: Residue modified with 2'-fluoro
<220> FEATURE:
<221> NAME/KEY: misc_feature
<222> LOCATION: (9)..(14)
<223> OTHER INFORMATION: Residue modified with 2'-O-methyl
<220> FEATURE:
<221> NAME/KEY: misc_feature
<222> LOCATION: (15)..(16)
<223> OTHER INFORMATION: Residue modified with 2'-fluoro

<400> SEQUENCE: 17
caaaauguaa aaaacu                                                     16

<210> SEQ ID NO 18
<211> LENGTH: 87
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: Residue modified to dFdCMP
<220> FEATURE:
<221> NAME/KEY: misc_feature
<222> LOCATION: (17)..(17)
<223> OTHER INFORMATION: Residue modified to dFdCMP
<220> FEATURE:
<221> NAME/KEY: misc_feature
<222> LOCATION: (19)..(19)
<223> OTHER INFORMATION: Residue modified to dFdCMP
<220> FEATURE:
<221> NAME/KEY: misc_feature
<222> LOCATION: (21)..(21)
<223> OTHER INFORMATION: Residue modified to dFdCMP
<220> FEATURE:
<221> NAME/KEY: misc_feature
<222> LOCATION: (27)..(27)
<223> OTHER INFORMATION: Residue modified to dFdCMP
<220> FEATURE:
<221> NAME/KEY: misc_feature
<222> LOCATION: (33)..(35)
<223> OTHER INFORMATION: Residue modified to dFdCMP
<220> FEATURE:
<221> NAME/KEY: misc_feature
<222> LOCATION: (37)..(38)
<223> OTHER INFORMATION: Residue modified to dFdCMP
<220> FEATURE:
<221> NAME/KEY: misc_feature
<222> LOCATION: (47)..(47)
<223> OTHER INFORMATION: Residue modified to dFdCMP
<220> FEATURE:
<221> NAME/KEY: misc_feature
<222> LOCATION: (55)..(55)
<223> OTHER INFORMATION: Residue modified to dFdCMP
<220> FEATURE:
<221> NAME/KEY: misc_feature
<222> LOCATION: (66)..(66)
<223> OTHER INFORMATION: Residue modified to dFdCMP
<220> FEATURE:
<221> NAME/KEY: misc_feature
<222> LOCATION: (69)..(69)
<223> OTHER INFORMATION: Residue modified to dFdCMP
<220> FEATURE:
<221> NAME/KEY: misc_feature
<222> LOCATION: (76)..(76)
<223> OTHER INFORMATION: Residue modified to dFdCMP
<220> FEATURE:
<221> NAME/KEY: misc_feature
<222> LOCATION: (78)..(78)
<223> OTHER INFORMATION: Residue modified to dFdCMP
<220> FEATURE:
<221> NAME/KEY: misc_feature
<222> LOCATION: (80)..(80)
<223> OTHER INFORMATION: Residue modified to dFdCMP
```

```
<220> FEATURE:
<221> NAME/KEY: misc_feature
<222> LOCATION: (83)..(83)
<223> OTHER INFORMATION: Residue modified to dFdCMP
<220> FEATURE:
<221> NAME/KEY: misc_feature
<222> LOCATION: (87)..(87)
<223> OTHER INFORMATION: Residue modified to dFdCMP

<400> SEQUENCE: 18
gggagacaag aauaaacgcu caauggcgaa ugcccgccua auagggcguu augacuuguu    60
gaguucgaca ggaggcucac aacaggc                                       87

<210> SEQ ID NO 19
<211> LENGTH: 87
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (13)..(13)
<223> OTHER INFORMATION: Residue modified to 5FdUMP
<220> FEATURE:
<221> NAME/KEY: misc_feature
<222> LOCATION: (20)..(20)
<223> OTHER INFORMATION: Residue modified to 5FdUMP
<220> FEATURE:
<221> NAME/KEY: misc_feature
<222> LOCATION: (24)..(24)
<223> OTHER INFORMATION: Residue modified to 5FdUMP
<220> FEATURE:
<221> NAME/KEY: misc_feature
<222> LOCATION: (31)..(31)
<223> OTHER INFORMATION: Residue modified to 5FdUMP
<220> FEATURE:
<221> NAME/KEY: misc_feature
<222> LOCATION: (39)..(39)
<223> OTHER INFORMATION: Residue modified to 5FdUMP
<220> FEATURE:
<221> NAME/KEY: misc_feature
<222> LOCATION: (42)..(42)
<223> OTHER INFORMATION: Residue modified to 5FdUMP
<220> FEATURE:
<221> NAME/KEY: misc_feature
<222> LOCATION: (49)..(50)
<223> OTHER INFORMATION: Residue modified to 5FdUMP
<220> FEATURE:
<221> NAME/KEY: misc_feature
<222> LOCATION: (52)..(52)
<223> OTHER INFORMATION: Residue modified to 5FdUMP
<220> FEATURE:
<221> NAME/KEY: misc_feature
<222> LOCATION: (56)..(57)
<223> OTHER INFORMATION: Residue modified to 5FdUMP
<220> FEATURE:
<221> NAME/KEY: misc_feature
<222> LOCATION: (59)..(60)
<223> OTHER INFORMATION: Residue modified to 5FdUMP
<220> FEATURE:
<221> NAME/KEY: misc_feature
<222> LOCATION: (64)..(65)
<223> OTHER INFORMATION: Residue modified to 5FdUMP
<220> FEATURE:
<221> NAME/KEY: misc_feature
<222> LOCATION: (77)..(77)
<223> OTHER INFORMATION: Residue modified to 5FdUMP

<400> SEQUENCE: 19
gggagacaag aauaaacgcu caauggcgaa ugcccgccua auagggcguu augacuuguu    60
gaguucgaca ggaggcucac aacaggc                                       87
```